US010441601B2

(12) United States Patent
Zakharenko

(10) Patent No.: US 10,441,601 B2
(45) Date of Patent: Oct. 15, 2019

(54) METHOD FOR TREATING SCHIZOPHRENIA

(71) Applicant: St. Jude Children's Research Hospital, Inc., Memphis, TN (US)

(72) Inventor: Stanislav S. Zakharenko, Collierville, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 0 days.

(21) Appl. No.: 15/740,687

(22) PCT Filed: Jun. 30, 2016

(86) PCT No.: PCT/US2016/040414
§ 371 (c)(1),
(2) Date: Dec. 28, 2017

(87) PCT Pub. No.: WO2017/004381
PCT Pub. Date: Jan. 5, 2017

(65) Prior Publication Data
US 2018/0318331 A1 Nov. 8, 2018

Related U.S. Application Data

(60) Provisional application No. 62/186,890, filed on Jun. 30, 2015.

(51) Int. Cl.
| | |
|---|---|
| *C12N 15/11* | (2006.01) |
| *A61K 31/713* | (2006.01) |
| *C12N 15/113* | (2010.01) |
| *C12Q 1/6883* | (2018.01) |
| *A61K 9/00* | (2006.01) |
| *C12N 15/861* | (2006.01) |
| *C12Q 1/6841* | (2018.01) |

(52) U.S. Cl.
CPC .......... *A61K 31/713* (2013.01); *A61K 9/0043* (2013.01); *C12N 15/113* (2013.01); *C12Q 1/6883* (2013.01); *C12N 15/861* (2013.01); *C12N 2310/141* (2013.01); *C12Q 1/6841* (2013.01); *C12Q 2600/106* (2013.01); *C12Q 2600/178* (2013.01); *G01N 2800/302* (2013.01)

(58) Field of Classification Search
None
See application file for complete search history.

(56) References Cited

U.S. PATENT DOCUMENTS

| | | |
|---|---|---|
| 2003/0215868 A1 | 11/2003 | Seeman et al. |
| 2014/0100282 A1 | 4/2014 | Wong |
| 2014/0235697 A1 | 8/2014 | Weiner et al. |
| 2015/0005365 A1 | 1/2015 | Zakharenko et al. |

FOREIGN PATENT DOCUMENTS

WO 2011/029903 A1 3/2011

OTHER PUBLICATIONS

Moreau et al, Altered MicroRNA Expression Profiles in Postmortem Brain Samples from Individuals with Schizophrenia and Bipolar Disorder, Biol Psychiatry, 2011, 69: 188-193 (Year: 2011).*
Abi-Dargham, A. et al., "Increased baseline occupancy of D2 receptors by dopamine in schizophrenia" Proc Natl Acad Sci. (2000) vol. 97, pp. 8104-8109.
Almeida, O.P. et al., "Psychotic states arising in late life (late paraphrenia) Psychopathology and Nosology" British Journal of Psychiatry (1995) vol. 166, pp. 205-214.
Ambros, V., "The functions of animal microRNAs" Nature (2004) vol. 431, pp. 350-355.
Andreasen, N.C. et al., "Schizophrenia and cognitive dysmetria: a positron-emission tomography study of dysfunctional prefrontal-thalamic-cerebellar circuitry" Proc. Natl. Acad. Sci. (1996) vol. 93, pp. 9985-9990.
Arora, V. et al., "c-Myc Antisense Limits Rat Liver Regeneration and Indicates Role for c-Myc in Regulating Cytochrome P-450 3A Activity" The Journal of Pharmacology and Experimental Therapeutics (2000) vol. 202, No. 3, pp. 921-928.
Baek, D. et al., "The Impact of MicroRNAs on Protein Output" Nature (2008) vol. 455, No. 7209, pp. 64-71.
Bartel, D.P., "MicroRNAs: Genomics, Biogenesis, Mechanism, and Function" Cell (2004) vol. 116, pp. 291-297.
Bassett, A.S. et al., "Chromosomal abnormalities and schizophrenia" Am. J. Med. Genet., (2000) vol. 97, pp. 45-51.
Bassett, A.S. et al., "Clinical features of 78 adults with 22q11 Deletion Syndrome". Am. J Med. Genet. (2005) vol. 138A, pp. 307-313.
Bassett, Anne S. et al., "Practical guidelines for managing patients with 22q11.2 deletion syndrome". J. Pediatr. (2011) vol. 159, pp. 332-339.
Bauer, S.M. et al., "Culture and the prevalence of hallucinations in schizophrenia". Comprehensive Psychiatry (2011) vol. 52, pp. 319-325.
Behrendt, R.P., "Hallucinations: synchronisation of thalamocortical gamma oscillations underconstrained by sensory input" Consciousness and Cognition (2003) vol. 12, pp. 413-451.
Boyden, E.S. et al., "Millisecond-timescale, genetically targeted optical control of neural activity" Nat. Neurosci. (2005) vol. 8, No. 9, pp. 1263-1268.
Braff, D.L. et al., "Human studies of prepulse inhibition of startle: normal subjects, patient groups, and pharmacological studies" Psychopharmacology (2001) vol. 156, pp. 234-258.
Breslow, R. et al., "An Artificial Cytochrome P450 that Hydroxylates Unactivated Carbons with Regio- and Stereoselectivity and Useful Catalytic Turnovers" Proc. Natl. Acad. Sci. (1997) vol. 94, pp. 11156-11158.
Carlsson, A., "The current status of the dopamine hypothesis of schizophrenia" Neuropsychopharmacology (1988) vol. 1, No. 3, pp. 179-186.

(Continued)

*Primary Examiner* — Ekaterina Poliakova-Georgantas
(74) *Attorney, Agent, or Firm* — Troutman Saunders LLP

(57) ABSTRACT

The invention is directed to a method for treating the 22q11 deletion syndrome (22q11 DS) and schizophrenia (SCZ) by replenishment of decreased levels of miR-338-3p in thalamic neurons.

11 Claims, 44 Drawing Sheets

Specification includes a Sequence Listing.

(56) References Cited

OTHER PUBLICATIONS

Chen, Y. et al., "Reproducibility of Quantitative RT-PCR Array in MiRNA Expression Profiling and Comparison with Microarray Analysis" BMC Genomics (2009) vol. 10, No. 407, pp. 1-10.

Cheng, W. et al., "Voxel-based, brain-wide association study of aberrant functional connectivity in schizophrenia implicates thalamocortical circuitry" Schizophrenia (2015) vol. 15016, pp. 1-8.

Chow, E.W.C. et al., "Neurocognitive profile in 22q11 deletion syndrome and schizophrenia," Schizophr Research (2006) vol. 87, pp. 270-278.

Christensen, M. et al., "Recombinant Adeno-Associated Virus-Mediated microRNA Delivery into the Postnatal Mouse Brain Reveals a Role for miR-134 in Dendritogenesis in Vivo" Front Neural Circuits (2010) vol. 3, Article 16, pp. 1-10.

Chun, S. et al. "Specific disruption of thalamic inputs to the auditory cortex in schizophrenia models" Science (2014) vol. 344, pp. 1178-1182.

Chun, S. et al., "Thalamocortical long-term potentiation becomes gated after the early critical period in the auditory cortex" J. Neurosci. (2013) vol. 33, No. 17, pp. 7345-7357.

Clinton, S.M. et al., "Thalamic dysfunction in schizophrenia: neurochemical, neuropathological, and in vivo imaging abnormalities" Schizophr. Res. (2004) vol. 69, pp. 237-253.

Conn, P. J. et al., "Schizophrenia: moving beyond monoamine antagonists" Mol. Interv. (2008) vol. 8, pp. 99-107.

Costain, G. et al. "Prenatal genetic testing with chromosomal microarray analysis identifies major risk variants for schizophrenia and other later-onset disorders" Am. J. Psychiatry (2013) vol. 170, pp. 1498.

Cronenwett, W. et al., "Thalamic pathology in schizophrenia" Curr. Top. Behav. Neurosci, (2010) vol. 4, pp. 509-528.

Denzler, R. et al., "Assessing the ceRNA hypothesis with quantitative measurements of miRNA and target abundance" Molecular Cell (2014) vol. 54, pp. 766-776.

Dierks, T. et al., "Activation of Heschl's gyrus during auditory hallucinations" Neuron (1999) vol. 22, pp. 615-621.

Donzé, O. et al., "RNA Interference in Mammalian Cells Using SiRNAs Synthesized with T7 RNA Polymerase" Nucleic Acids Research (2002) vol. 30, No. 10 e46, pp. 1-4.

Dweep, H. et al., "MiRWalk—database: prediction of possible miRNA binding sites by "walking" the genes of three genomes" J Biomed Informatics (2011) vol. 44, pp. 839-847.

Earls, L. R. et al., "A Synaptic Function Approach to Investigating Complex Psychiatric Diseases" The Neuroscientist (2013) vol. 20, No. 3, pp. 257-271.

Earls, L. R. et al., "Age-dependent microRNA control of synaptic plasticity in 22q11 deletion syndrome and schizophrenia" The Journal of Neuroscience (2012) vol. 32, pp. 14132-14144.

Emptage, N. J. et al., "Optical quantal analysis reveals a presynaptic component of LTP at hippocampal Schaffer-associational synapses" Neuron (2003) vol. 38, pp. 797-804.

Ettinger, U. et al., "Magnetic Resonance Imaging of the Thalamus and Adhesio Interthalamica in Twins with Schizophrenia" Archives of General Psychiatry (2007) vol. 64, pp. 401-409.

Feinstein, C. et al., "Psychiatric disorders and behavioral problems in children with velocardiofacial syndrome: usefulness as phenotypic indicators of schizophrenia risk" Biol. Psychiatry (2002) vol. 51, pp. 312-318.

Fenelon, K. et al., "The pattern of cortical dysfunction in a mouse model of a schizophrenia-related microdeletion" J. Neurosci. (2013) vol. 33, pp. 14825-14839.

Ford, J.M. et al., "Tuning in to the voices: a multisite fMRI study of auditory hallucinations" Schizophrenia Bulletin (2009) vol. 35, No. 1, pp. 58-66.

Fung, W. L. et al., "Elevated prevalence of generalized anxiety disorder in adults with 22q11.2 deletion syndrome" Am. J. Psychiatry (2010) vol. 167, p. 998.

Gabizon, A. et al., "Liposome Formulations with Prolonged Circulation Time in Blood and Enhanced Uptake by Tumors" Proc. Natl. Acad. Sci. (1988) vol. 85, pp. 6949-6953.

García-Arieta, A. et al., "Spray-Dried Powders as Nasal Absorption Enhancers of Cyanocobalamin" Biol. Pharm. Bull. (2001) vol. 24, No. 12, pp. 1411-1416.

Gorman, C.M. et al., "The Rous Sarcoma Virus Long Terminal Repease is a Strong Promoter When Introduced into a Variety of Eukaryotic Cells by DNA-Mediated Transfection" Proceedings of the National Academy of Sciences of the United States of America (1982) vol. 79, pp. 6777-6781.

Gothelf, D. et al., "Clinical characteristics of schizophrenia associated with velo-cardio-facial syndrome". Schizophrenia Research (1999) vol. 35, pp. 105-112.

Green, T. et al., "Psychiatric disorders and intellectual functioning throughout development in velocardiofacial (22q11 .2 deletion) syndrome" J. Am. Acad. Child Adolesc. Psychiatry (2009) vol. 48, pp. 1060-1068.

Griffiths-Jones, S. et al., "miRBase: microRNA sequences, targets and gene nomenclature" Nucleic Acids Research (2006) vol. 34, pp. D140-D144 (2006). Database issue: doi:10.1093/nar/gkj112.

Hoffman, Ralph E. et al., "Time course of regional brain activity accompanying auditory verbal hallucinations in schizophrenia" Br. J. Psychiatry (2011) vol. 198, pp. 277-283.

Horga, G. et al., "Deficits in predictive coding underlie hallucinations in schizophrenia" J Neuroscience (2014) vol. 34, pp. 8072-8082.

Hubl, D. A. et al., "Competition for neuronal resources: how hallucinations make themselves heard" Br. J. Psychiatry (2007) vol. 190, pp. 57-62. Doi:10.1192/bjp.bp.106.022954.

Insel, T.R., "Rethinking schizophrenia" Nature (2010) vol. 468, pp. 187-193.

International Preliminary Report on Patentability issued by the International Searching Authority in International Application No. PCT/US2015/040414, dated Jan. 17, 2017.

Jang, S.K. et al., "Initiation of Protein Synthesis by Internal Entry of Ribosomes into the 5' Nontranslated Region of Encephalomyocarditis Virus RNA in Vivo" Journal of Virology (1989) vol. 63, No. 4, pp. 1651-1660.

Sommer, I. E. et al., "Auditory verbal hallucinations predominantly activate the right inferior frontal area" Brain (2008) vol. 131, pp. 3169-3177.

Srikantan, S, et al., "Paradoxical microRNAs: individual gene repressors, global translation enhancers" Cell Cycle (2011) vol. 10, pp. 751-759.

Stark, K. L. et al., "Altered brain microRNA biogenesis contributes to phenotypic deficits in a 22q11-deletion mouse model" Nat Genetics (2008) vol. 40, pp. 751-760.

Swerdlow, N. R. et al., "Realistic expectations of prepulse inhibition in translational models for schizophrenia research" Psychopharmacology (2008) vol. 199, pp. 331-388.

Thaker, G. K. et al., "Advances in schizophrenia" Nat Med (2001) vol. 7, pp. 667-671.

Van Rooij, E. et al., "Development of MicroRNA Therapeutics is Coming of Age" EMBO Molecular Medicine (2014) vol. 6, pp. 851-864.

Vorstman, J. A. et al., "Expression of autism spectrum and schizophrenia in patients with a 22q11.2 deletion" Schizophr. Res., (2013) vol. 143, pp. 55-59.

Welsh, Robert C. et al., "Low-frequency BOLD fluctuations demonstrate altered thalamocortical connectivity in schizophrenia". Schizophr. Bull., vol. 36, pp. 713-722 (2010).

Wong, D. F. et al., "Positron emission tomography reveals elevated D2 dopamine receptors in drug-naive schizophrenics" Science (1986) vol. 234, pp. 1558-1563.

Woo, P. Y. et al., "Monoaural musical hallucinations caused by a thalamocortical auditory radiation infarct: a case report" J. Med. Case. Rep. (2014) vol. 8, No. 400, pp. 1-4.

Woodruff, P. et al., "Auditory hallucinations and perception of external speech" Lancet (1995) vol. 346, pp. 1035-1036.

Woodward, N. D. et al., "Thalamocortical dysconnectivity in schizophrenia" Am. J Psychiatry (2012) vol. 169, pp. 1092-1099.

(56) References Cited

OTHER PUBLICATIONS

Yu, J-Y. et al., "RNA Interference by Expression of Short-Interfering RNAs and Hairpin RNAs in Mammalian Cells" PNAS (2002) vol. 99, No. 9, pp. 6047-6052.
Javitt, D. C. et al., "Auditory dysfunction in schizophrenia: integrating clinical and basic features" Nat. Rev. Neurosci. (2015) vol. 16, pp. 535-550.
Judice, J.K. et al., "Inhibition of HIV Type 1 Infectivity by Constrained Alpha-Helical Peptides: Implications for the Viral Fusion Mechanism" Pro Natl Acad Sci (1997) vol. 94, pp. 13426-13430.
Kaminsky, E. B. et al., "An evidence-based approach to establish the functional and clinical significance of copy number variants in intellectual and developmental disabilities" Genetics in Medicine (2011) vol. 13, pp. 777-784.
Karayiorgou, M. et al., "22q11.2 microdeletions: linking DNA structural variation to brain dysfunction and schizophrenia" Nat Rev Neuroscience (2010) vol. 11, pp. 402-416.
Kirsch, R.D. et al., "An Improved PCR-Mutagenesis Strategy for Two-Site Mutagenesis or Sequence Swapping Between Related Genes" Nucleic Acids Research (1998) vol. 26, No. 7, pp. 1848-1850.
Kluiver, J. et al., "Generation of miRNA sponge constructs," Methods (2012) vol. 58, pp. 113-117.
Kluiver, J. et al., "Rapid Generation of MicroRNA Sponges for microRNA inhibition" PLoS One (2012) vol. 7, Issue No. 1, pp. 1-8.
Kompus, K. et al., "The "paradoxical" engagement of the primary auditory cortex in patients with auditory verbal hallucinations: a meta-analysis of functional neuroimaging studies" Neuropsychologia (2011) vol. 49, pp. 3361-3369.
Kunkel, T.A., "Rapid and Efficient Site-Specific Mutagenesis Without Phenotypic Selection" Proc. Natl. Acad. Sci. (1985) vol. 82, pp. 488-492.
Lemaitre, M. et al., "Specific Antiviral Activity of a Poly(L-Lysine)-Conjugated Oligodeoxyribonucleotide Sequence Complementary to Vesicular Stomatitis Virus N Protein mRNA Initiation Site" Proc Natl Acad Sci (1987) vol. 84, pp. 648-652.
Lennox, B. R. et al., "The functional anatomy of auditory hallucinations in schizophrenia" Psychiatry Res. (2000) vol. 100, pp. 13-20.
Letsinger, R.L. et al., "Cholesteryl-Conjugated Oligonucleotides: Synthesis, Properties, and Activity as Inhibitors of Replication of Human Immunodeficiency Virus in Cell Culture" Proc Natl Acad Sci (1989) vol. 86, pp. 6553-6556.
Leucht, S. et al., "Second-generation versus first-generation antipsychotic drugs for schizophrenia: a meta-analysis" Lancet (2009) vol. 373, pp. 31-41.
Lewis, D. A. et al., "Catching up on schizophrenia: natural history and neurobiology" Neuron (2000) vol. 28, pp. 325-334.
Lindsay, E. A. et al., "Congenital heart disease in mice deficient for the DiGeorge syndrome region" Nature (1999) vol. 401, pp. 379-383.
Lindsay, E. A. et al., "Tbx1 haploinsufficieny in the DiGeorge syndrome region causes aortic arch defects in mice" Nature (2001) vol. 410, pp. 97-101.
Lisman, J. E. et al., "A thalamo-hippocampal-ventral tegmental area loop may produce the positive feedback that underlies the psychotic break in schizophrenia" Biol. Psychiatry (2010) vol. 68, pp. 17-24.
Llinas, R. et al., "Coherent 40-Hz oscillation characterizes dream state in humans" Proc. Natl. Acad. Sci. (1993) vol. 90, pp. 2078-2081.
Llinas, R.R. et al., "Of dreaming and wakefulness" Neuroscience (1991) vol. 44, pp. 521-535.
Marenco, S. et al., "Investigation of anatomical thalamo-cortical connectivity and FMRI activation in schizophrenia" Neuropsychopharmacology (2012) vol. 37, pp. 499-507.
McDonald-McGinn, D.M. et al., "Chromosome 22q11.2 deletion syndrome (DiGeorge syndrome/velocardiofacial syndrome)" Medicine (Baltimore) (2011) vol. 90, No. 1, pp. 1-18.
Mellado Lagarde, M.M. et al., "Spontaneous regeneration of cochlear supporting cells after neonatal ablation ensures hearing in the adult mouse" Proc Natl Acad Sci. (2014) vol. 111, No. 47, pp. 16919-16924.
Miyamoto, S. et al., "Pharmacological treatment of schizophrenia: a critical review of the pharmacology and clinical effects of current and future therapeutic agents" Mol. Psychiatry (2012) vol. 17, pp. 1206-1227.
Mueser, K. T. et al., "Schizophrenia" Lancet (2004) vol. 363, pp. 2063-2072.
Mueser, K.T. et al., "Hallucinations in schizophrenia" Acta Psychiatr Scan (1990) vol. 82, pp. 26-29.
Murphy, K. C. et al., "High rates of schizophrenia in adults with velo-cardio-facial syndrome" Arch. Gen. Psychiatry (1999) vol. 56, pp. 940-945.
Murphy, K. C., "Schizophrenia and velo-cardio-facial syndrome" Lancet (2002) vol. 359, pp. 426-430.
Ndetei, D.M. et al., "A comparative cross-cultural study of the frequencies of hallucination in schizophrenia" Acta Psychiatr. Scand. (1984) vol. 70, pp. 545-549.
Oke, A. F. et al., "Elevated dopamine/norepinephrine ratios in thalami of schizophrenic brains" Biol. Psychiatry (1988) vol. 24, pp. 79-82.
Paddison, P.J. et al., "Short Hairpin RNAs (shTNAs) Induce Sequence-Specific Silencing in Mammalian Cells" Genes & Development (2002) vol. 16, pp. 948-958.
Parnaudeau, S. et al., "Inhibition of mediodorsal thalamus disrupts thalamofrontal connectivity and cognition" Neuron, Cell Press (2013) vol. 77, pp. 1151-1162.
Pulver, A. E. et al., "Psychotic illness in patients diagnosed with velo-cardio-facial syndrome and their relatives" The Journal of Nervous and Mental Disease (1994) vol. 182, No. 8, pp. 476-478.
Pulver, A.E., "Search for schizophrenia susceptibility genes" Biol Psychiatry (2000) vol. 47, pp. 221-230.
Rabinowitz, J.E. et al., "Cross-Packaging of a Single Adeno-Associated Virus (AAV) Type 2 Vector Genome into Multiple AAV Serotypes Enables Transduction with Broad Specificity" Journal of Virology (2002) vol. 76, No. 2, pp. 791-801.
Rehm, B.H. et al., "Membrane Topology of the Outer Membrane Protein OprH from Pseudomonas aeruginosa: PCR-Mediated Site-Directed Insertion and Deletion Mutagenesis" Journal of Bacteriology (1996) vol. 178, No. 11, pp. 3346-3349.
Richardson, R.J. et al., "Connectivity patterns revealed by mapping of active inputs on dendrites of thalamorecipient neurons in the auditory cortex". J Neurosci. (2009) vol. 29, pp. 6406-6417.
Samulski, R.J. et al., "A Recombinant Plasmid from Which an Infectious Adeno-Associated Virus Genome Can Be Excised In Vitro and Its Use to Study Viral Replication" Journal of Virology (1987) vol. 61, No. 10, pp. 3096-3101.
Samulski, R.J. et al., "Helper-Free Stocks of Recombinant Adeno-Associated Viruses: Normal Integration Does Not Require Viral Gene Expression" Journal of Virology (1989) vol. 63, No. 9, pp. 3822-3829.
Scambler, P. J., et al. "Velo-cardio-facial syndrome associated with chromosome 22 deletions encompassing the DiGeorge locus" Lancet (1992) vol. 339, pp. 1138-1139.
Schneider, M. et al., "Psychiatric disorders from childhood to adulthood in 22q11.2 deletion syndrome: results from the International Consortium on Brain and Behavior in 22q11.2 Deletion Syndrome" Am. J. Psychiatry (2014) vol. 171, pp. 627-639.
Schulman, C. A. et al., "Hallucinations and disturbances of affect, cognition, and physical state as a function of sensory deprivation" Perceptual & Motor Skills (1967) vol. 25, pp. 1001-1024.
Seeman, P. et al., "Antipsychotic drugs: direct correlation between clinical potency and presynaptic action on dopamine neurons" Science (1975) vol. 188, pp. 1217-1219.
Selbach, M. et al., "Widespread Changes in Protein Synthesis Induced by MicroRNAs" Nature (2008) vol. 455, pp. 59-63.
Shprintzen, R.J. et al., "Late-onset psychosis in the velo-cardio-facial syndrome" Am. J. Med. Genet. (1992) vol. 42, pp. 141-142.
Silbersweig, D. A. et al., "A functional neuroanatomy of hallucinations in schizophrenia," Nature (1995) vol. 378, pp. 176-179.

(56) References Cited

OTHER PUBLICATIONS

Small, E. M. et al., "Pervasive roles of microRNAs in cardiovascular biology" Nature (2011) vol. 469, pp. 336-342.

Small, I. F. et al., "Clinical Characteristics of Hallucinations of Schizophrenia" Diseases of the Nervous System (1966) vol. 27, pp. 349-353.

Smith, P. H. et al., "Fundamental differences between the thalamocortical recipient layers of the cat auditory and visual cortices" J Comp Neurol. (2001) vol. 436, pp. 508-519.

Snyder, S. H., "Drugs for a new millennium" Philos Trans. Royal Society Lond B Biol Sci. (1999) vol. 354, pp. 1985-1994.

Sobin, C. et al., "Associations between prepulse inhibition and executive visual attention in children with the 22q11 deletion syndrome" Molecular Psychiatry (2005) vol. 10, pp. 553-562.

International Search Report and Written Opinion issued by the International Searching Authority in International Application No. PCT/US2015/040414, dated Oct. 4, 2016.

Shioya, M., et al., "Aberrant microRNA Expression in the Brains of Neurodegenerative Diseases: miR-29a Decreased in Alzheimer Disease Brains Targets Neurone Navigator 3" Neuropathology and Applied Neurobiology (2010) vol. 36, Issue 4, pp. 320-330.

* cited by examiner

MGv

ACx (L3/4)

*miR-338-3p* sponge (SEQ ID NO: 37)
(SEQ ID NO: 38)

MGv

FIG. 4f
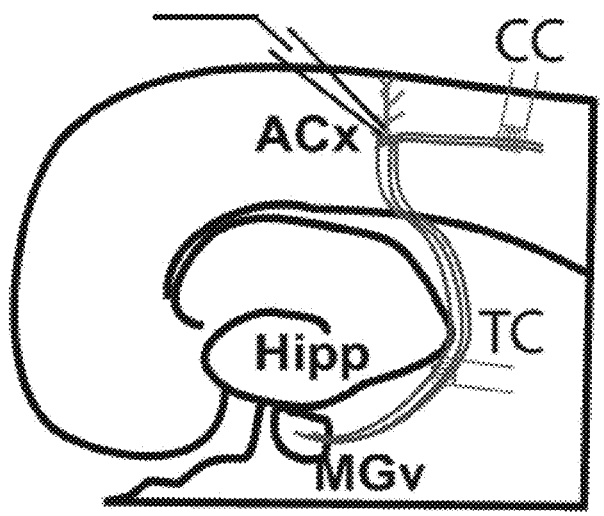
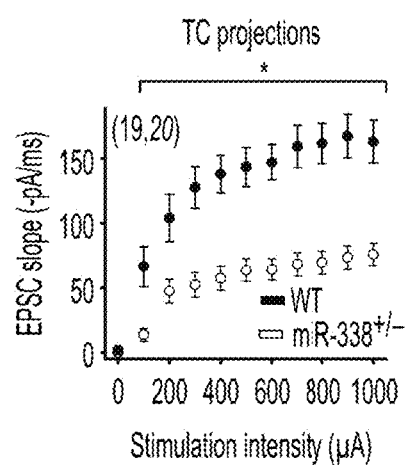
FIG. 4g
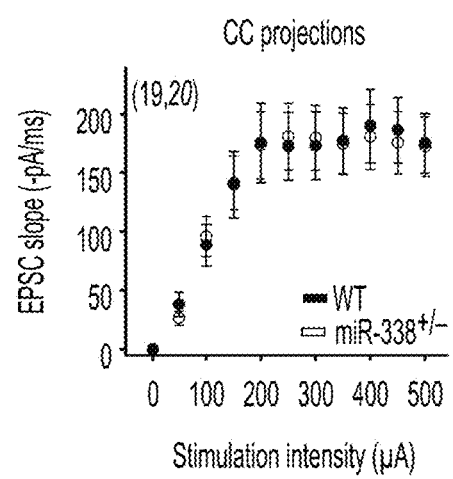
FIG. 4h

SEQUENCE LISTING

<160> NUMBER OF SEQ ID NOS: 44

<210> SEQ ID NO 1
<211> LENGTH: 22
<212> TYPE: RNA
<213> ORGANISM: Homo sapiens

<400> SEQUENCE: 1
uccagcauca gugauuuugu ug                                             22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tccagcatca gtgattttgt tg                                             22

```
<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttcatta ttgctcctga cc                                              22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcaagagcaa taacgaaaaa tgt                                             23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcagctccta tatgatgcct tt                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cggcgtcatg caggagttga tt                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcaacaaaat cactgatgct gg                                              22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcagcaccag gatattgttg ggg                                             23
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggatgtcatg atgtgcacag c                                          21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgcttgcgga gaacgatg                                              18

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atgctggcct gcctgtgttg t                                          21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggggcagga catacacatc gg                                         22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgcttcggca gcacatatac                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttcacgaatt tgcgtgtcat                                            20
```

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
cttttgaacc cttttccatc tg                                             22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
ttaacaaaaa ttcgtcacta cca                                            23

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
gtacagctgt tgacagtgag cgactccagc atcagtgatt ttgttgtgtg aa            52

<210> SEQ ID NO 18
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ccatctgtgg cttcacacaa caaaatcact gatgctggag tcgctcactg tcaacagct     59

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
gccacagatg gcaacaaaat ctgatgctgg agctgcctac tgcctcggaa               50

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
agctttccga ggcagtaggc agctccagca tcagattttg ttg                      43

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtacagctgt tgacagtgag cgactcagct cctatatgat gccttttgtg aa            52

<210> SEQ ID NO 22
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccatctgtgg cttcacaaaa ggcatcatat aggagctgag tcgctcactg tcaacagct     59

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccacagatg gaaaggcatc ataggagctg agctgcctac tgcctcggaa               50

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctttccga ggcagtaggc agctcagctc ctatgatgcc ttt                      43

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtacagctgt tgacagtgag cgaccggcgt catgcaggag ttgatttgtg aa            52

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccatctgtgg cttcacaaat caactcctgc atgacgccgg tcgctcactg tcaacagct     59

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gccacagatg gaatcaactc gcatgacgcc ggctgcctac tgcctcggaa        50

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
agctttccga ggcagtaggc agccggcgtc atgcgagttg att        43

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gtacagctgt tgacagtgag cgacttttc attattgctc ctgacctgtg aa        52

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ccatctgtgg cttcacaggt caggagcaat aatgaaaaag tcgctcactg tcaacagct        59

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
gccacagatg gggtcaggag ataatgaaaa agctgcctac tgcctcggaa        50

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
agctttccga ggcagtaggc agcttttca ttatctcctg acc        43

<210> SEQ ID NO 33
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtacagctgt tgacagtgag cgactcaaga gcaataacga aaaatgttgt gaa          53

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccatctgtgg cttcacaaca tttttcgtta ttgctcttga gtcgctcact gtcaacagct    60

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gccacagatg gacattttc gattgctctt gagctgccta ctgcctcgga a              51

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agctttccga ggcagtaggc agctcaagag caatcgaaaa atgt                     44

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caacaaaatg cggatgctgg a                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gacactgtga gcgaagacat a                                              21

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atagcataca ttatacgaag ttatcactgg                                     30

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cttcactaca ctctccctag tacagtctc                                      29

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tctagaaagt ataggaactt ccatggtc                                       28

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aggagactca tagttctctg tatcatagc                                      29

<210> SEQ ID NO 43
<211> LENGTH: 2545
<212> TYPE: DNA
<213> ORGANISM: Mus musculus

<400> SEQUENCE: 43
acggctgccg gagggcggc cgtgcgtgga tgcggcggga gctggaagcc tcgagcagcc      60
ggcgccttct ctggccccgg gcgccctatg gcttgaagag ccgtgccacc cagtggcccc     120
actgccccaa tggatccact gaacctgtcc tggtacgatg atgatctgga gaggcagaac     180
tggagccggc ccttcaatgg gtccgaaggg aaggcagaca ggccccacta caactactat     240
gccatgctgc tcaccctcct catctttatc atcgtctttg gcaatgtgct ggtgtgcatg     300
gctgtatcac gagagaaggc tttgcagacc accaccaact acctgatagt cagcctcgct     360
gtggccgatc ttctggtggc cacactggtt atgccctggg tcgtctatct ggaggtggtg     420
ggtgagtgga aattcagcag gattcactgt gacatctttg tcactctgga tgtcatgatg     480
tgcacagcaa gcatcttgaa cctgtgtgcc atcagcatcg acaggtacac agctgtggcc     540
atgcctatgt tgtataacac acgctacagc tccaagcgcc gagttactgt catgatcgcc     600

```
attgtctggg tcctgtcctt caccatctct tgcccactgc tctttggact caacaacaca    660
gaccagaatg agtgtatcat tgccaaccct gccttcgtgg tctactcctc catcgtctcg    720
ttctacgtgc ccttcatcgt caccctgctg gtctatatca aaatctacat cgttctccgc    780
aagcgtcgga agcgggtcaa caccaagcgt agcagccgag ctttcagagc caacctgaag    840
acaccactca agggcaactg tacccaccct gaggacatga aactctgcac cgttatcatg    900
aagtctaatg ggagtttccc agtgaacagg cggagaatgg atgctgcccg ccagctcag     960 gagctggaaa tggagatgct gtcaagcacc agccccccag agaggacccg gtatagcccc   1020
atccctccca gtcaccacca gctcactctc cccgatccat cccaccacgg tctacatagc   1080
aaccctgaca gtcctgccaa accagaaaag aatgggcatg ccaagattgt caatcccagg   1140
attgccaagt tctttgagat ccagaccatg cccaatggca aaacccggac ctcccttaag   1200
acgatgagcc gcaggaagct ctcccagcag aaggagaaga agccactca gatgcttgcc    1260 attgttcttg gtgtgttcat catctgctgg ctgcccttct tcatcacgca catcctgaat   1320
atacactgtg actgcaacat cccaccagtc tctacagcg ccttcacatg gctgggctat    1380
gtcaacagtg ccgtgaaccc catcatctat accaccttca acattgagtt ccgcaaggcc   1440
ttcatgaaga tcctgcactg ctgagtctgc cccttgcctg cacagcagct gcttgccgcc   1500
tccctgccta ggcaggccag acctcatccc tgcaagctgt gggcagaaag gcccagatgg   1560
actcggcctt tccttgaccc tgcaggctct gcagtgttag cttggctcgg tgccctctc    1620 tgcccacaca cccttatcct gccagggtag ggccagggag actggtatct taccagctct   1680
ggggttggat ccatggctca gagcagctca cagagtgccc cttcacatg cagatcctgt    1740 ctccttggca ccaaagaagc agcagccttc cttgaccttc ctctcaggca cggaagctag   1800
ctcagtagcg gagcacacct tgattgtggg cttggcctgg cccttgcttg cctatgttgg   1860
atcaggtggt agaagagaag gacagttctt actttacagg gaccacatag gaaagcaggg   1920
aacatgccaa ggcctccagg tgacgttagt gtcgggagac acacataaac accaggtagc   1980
tccacggacc ccagagaaac tgaggctgaa atctgttttt ccaccccaac tctagtgtga   2040
atccctactt tccatagcag tgggtattgc tatgttctcc actgttatag aatcccatgg   2100
ggtttctgta ccttcggggg aaaataactc taatcctcaa gggccccaag agagactgta   2160
aagagaaaaa tagctgattt ccctctaccc tccaatccac tccgccactt cttgacatac   2220
attggacata gccattcccc acagcagatg ctggacagcc tgggaagttg agccttggac   2280
cagtgttgga gctgaagttg gaggtggtaa cttggggctc ttgggcgggg ggtgttgata   2340
tcttccctct tccaagtctc ttctctgcca gtgcctctgc cttagaggag gctgtggatg   2400
gggctgctgg ggctgctgat accattgggt ctggccctga gtgagggtgg ggaagctgca   2460
gcttggaggg gtctgggctc caactctgta acatcaccat acatgcacca aaccaataaa   2520
accttgacaa gagtcattcc cacgg                                         2545
```

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 44

```
tccagcatca gtgatttgt tg                                               22
```

METHOD FOR TREATING SCHIZOPHRENIA

CROSS-REFERENCE TO RELATED APPLICATIONS

This application is the U.S. National Phase application under 35 U.S.C. § 371 of International Patent Application No. PCT/US2016/040414, filed on Jun. 30, 2016, and claims priority to U.S. Provisional Application No. 62/186,890, filed on Jun. 30, 2015, both of which applications are incorporated by reference in their entireties.

STATEMENT AS TO FEDERALLY SPONSORED RESEARCH

This invention was made with government support under grants MH097742 and MH095810 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 24, 2016, is named 243734_000079_SL.txt and is 13,687 bytes in size.

FIELD OF THE INVENTION

The invention is directed to a method for treating the 22q11 deletion syndrome (22q11 DS) and schizophrenia (SCZ) by replenishment of decreased levels of miR-338-3p in thalamic neurons.

BACKGROUND OF THE INVENTION

Auditory hallucinations and other positive symptoms of schizophrenia (SCZ) such as delusions, disorganized thought, and psychosis typically appear during late adolescence or early adulthood[1,2] and are alleviated in most patients by antipsychotics that inhibit D2 dopamine receptors (DRD2s)[3-5]. The mechanisms of such late onset of schizophrenia's positive symptoms and underlying neuronal circuits remain unknown. Thalamocortical (TC) projections to the auditory cortex (ACx) emerged as a circuit specifically disrupted in mouse models of 22q11 deletion syndrome (22q11DS)[6,7]. This disorder is a leading genetic cause of schizophrenia[8-10] and instigated by the hemizygous deletion of multiple genes (1.5-3 Mb) of the q (long) arm of chromosome 22 in humans[11]. Deletion of one 22q11DS gene, the microRNA (miRNA)-processing gene Dgcr8, leads to high levels of Drd2 in the auditory thalamus, TC disruption, abnormal sensitivity of TC projections to antipsychotics, and deficits in acoustic-startle responses characteristic of schizophrenia[6], through miRNA depletion[12-14].

Several studies have indicated that drug-naïve schizophrenic patients have elevated levels of DRD2s in their brains[25,26]. Drd2 upregulation leads to deficits in TC synaptic transmission and acoustic startle and also renders TC projections sensitive to antipsychotics. Antipsychotics that effectively treat only positive symptoms but not cognitive or negative symptoms of the disease[27], eliminate synaptic deficits at TC projections and acoustic-startle deficiency in 22q11DS mice[6]. Antipsychotics alleviate positive symptoms of schizophrenia through systemic inhibition of DRD2, which is accompanied by multiple and sometimes devastating side effects, such as blood abnormalities, weight gain, abnormal movements (such as the movements as with Parkinson's disease) and many others[2,28].

The 22q11.2 deletion syndrome (22q11DS) is associated with high risk of developing schizophrenia symptoms, including psychosis, later in life. Auditory thalamocortical projections recently emerged as a circuit specifically disrupted in 22q11DS mouse models. Haploinsufficiency of the microRNA-processing gene Dgcr8 results in the elevation of the dopamine receptor Drd2 in the auditory thalamus, an abnormal sensitivity of thalamocortical projections to antipsychotics, and an abnormal acoustic-startle response. These auditory abnormalities have a delayed onset in 22q11DS mouse models and are associated with age-dependent reduction of the microRNA miR-338-3p, which targets Drd2 and is enriched in the thalamus of humans and mice. Replenishing depleted miR-338-3p in the mature 22q11DS mice rescued the thalamocortical abnormalities, and miR-338-3p deletion/knockdown mimicked thalamocortical and behavioral deficits and eliminated their age dependence. Thus, miR-338-3p depletion is necessary and sufficient to disrupt auditory thalamocortical signaling in 22q11DS mouse models and may therefore mediate the pathogenic mechanism of 22q11DS-related psychosis and control its late onset.

The 22q11DS is considered a leading genetic cause of schizophrenia[46-48]. Schizophrenia develops in 23% to 43% of individuals with 22q11DS[49-54], most of whom experience psychosis[55,56] Furthermore, 30% to 50% of nonschizophrenic individuals with 22q11DS demonstrate subthreshold symptoms of psychosis[57]. Nonpsychotic behavioral abnormalities are present from early adulthood in 22q11DS[58,59], but psychotic symptoms and schizophrenia are delayed until adulthood[54,60] It remains unclear why the onset of psychotic symptoms is so delayed. In schizophrenic patients, auditory hallucinations and other psychotic symptoms are similarly delayed until late adolescence or early adulthood[61,62], are present in 60% to 90% of cases[63], and are often alleviated by antipsychotics that inhibit D2 dopamine receptors (DRD2s)[64-67]. Given the germline occurrence of deleted genes in 22q11DS, it is not clear why the onset of positive symptoms is delayed.

Recently, Dgcr8 emerged as a culprit gene responsible for several neuronal phenotypes observed in mouse models of 22q11DS[68-70], including the disruption of synaptic transmission at TC projections to the ACx[39]. Dgcr8 is part of the microprocessor complex that mediates the biogenesis of microRNAs (miRNAs), small RNAs that negatively regulate the expression of complementary mRNAs and protein translation[71]. Dgcr8 haploinsufficiency in 22q11DS leads to depletion of miRNAs and the resultant upregulation of respective targets, which in turn disrupts synaptic transmission, synaptic plasticity, and proper functioning of neural circuits[72]. In adult 22q11DS mouse models, Dgcr8 haploinsufficiency is sufficient to upregulate Drd2 mRNA and protein in the auditory thalamus, which causes auditory abnormalities that include decreased glutamatergic synaptic transmission at TC projections to the ACx and deficient prepulse inhibition (PPI) of the acoustic-startle response[39]. Abnormally high levels of Drd2 in the thalamus of 22q11DS mice increase TC projection sensitivity to Drd2 antagonists, including antipsychotics. As a consequence, auditory synaptic and behavioral abnormalities of 22q11DS mice are rescued by antipsychotics[39].

It was tested whether TC disruption follows the same age-dependent trajectory as psychosis in patients with 22q11DS or schizophrenia and determined the molecular underpinnings of TC disruption in 22q11DS mice. Similar to psychotic symptoms, TC disruption of synaptic transmission had a delayed onset. In a series of miRNA and physiological screens, the thalamus-enriched Drd2-targeting miR-338-3p was identified as that which mediates the Dgcr8-Drd2 mechanism of TC disruption. It is also shown that miR-338-3p is depleted in mouse models of 22q11DS and schizophrenic patients and that replenishment of miR-338-3p in the auditory thalamus rescued the TC deficits in 22q11DS mouse models. Lastly, evidence is presented showing that miR-338-3p is a key controller of the late onset of TC disruption in 22q11DS mice.

SUMMARY OF THE INVENTION

There is a great need in the art to develop effective treatments for schizophrenia and the 22q11 deletion syndrome, including treatment of positive symptoms of schizophrenia, such as, e.g., hallucinations, delusions, disorganized thought, and psychosis. There is also a great need to develop diagnostic methods for schizophrenia. The present invention addresses these and other needs by providing methods based on microRNA miR-338-3p.

In one aspect, the invention provides a method for treatment and/or prevention of schizophrenia in a subject in need thereof, the method comprising administering to the subject a therapeutically effective amount of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p.

In a related aspect, the invention provides a method for treatment of 22q11 deletion syndrome in a subject in need thereof, the method comprising administering to the subject a therapeutically effective amount of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p.

In another related aspect, the invention provides a method for treatment and/or prevention of a positive symptom of schizophrenia (e.g., hallucinations, delusions, disorganized thought, or psychosis) in a subject in need thereof, the method comprising administering to the subject a therapeutically effective amount of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p.

In one embodiment of any of the above methods, the miR-338-3p or mimic or derivative thereof comprises the sequence UCCAGCAUCAGUGAUUUUGUUG (SEQ ID NO: 1). In one embodiment of any of the above methods, the miR-338-3p or mimic or derivative thereof consists of the sequence UCCAGCAUCAGUGAUUUUGUUG (SEQ ID NO: 1).

In one embodiment of any of the above methods, the vector is selected from the group consisting of adeno-associated virus (AAV) vectors, lentivirus vectors and Sindbis virus vectors.

In one embodiment of any of the above methods, the expression of miR-338-3p or mimic or functional derivative thereof in the vector is controlled by a promoter selected from the group consisting of Synapsin promoter, CMV promoter, β-actin promoter, and CamKIIa promoter.

In one embodiment of any of the above methods, the administration is systemic. In another embodiment of any of the above methods, the administration is intranasal.

In one embodiment of any of the above methods, the administration is targeted to the thalamus.

In one embodiment of any of the above methods, the administration results in an increase in the level of miR-338-3p in thalamic neurons of the subject to the level found in healthy subjects.

In one embodiment of any of the above methods, the administration results in a decrease in sensitivity of thalamic neurons to an antipsychotic agent (e.g., haloperidol, clozapine, olanzapine, or another antipsychotic agent inhibiting a D2 dopamine receptor).

In one embodiment of any of the above methods, the subject has a decreased level of miR-338-3p in thalamic neurons as compared to a control (e.g., a predetermined standard, or the level of miR-338-3p in thalamic neurons of a healthy age- and gender-matched subject or an average value for several such subjects).

In one embodiment of any of the above methods, the method further comprises determining the level of miR-338-3p in thalamic neurons or a bodily fluid sample obtained from the subject (e.g., blood [e.g., whole blood, blood lymphocytes, peripheral blood mononuclear cells (PBMCs), blood plasma, or blood serum], urine, saliva, or cerebrospinal fluid [CSF]). In one specific embodiment, the level of miR-338-3p is determined using a method selected from the group consisting of hybridization, array-based assays, PCR-based assays (e.g., qPCR), and sequencing. In one specific embodiment, the level of miR-338-3p is determined prior to the administration of the treatment. In one specific embodiment, the level of miR-338-3p is determined both prior and after the administration of the treatment.

In one embodiment of any of the above methods, the method further comprises administering to the subject an additional treatment agent. In one specific embodiment, the additional treatment agent is an antipsychotic (e.g., haloperidol, clozapine, olanzapine, or another antipsychotic agent inhibiting a D2 dopamine receptor).

In a separate aspect, the invention provides a method for determining efficacy of a treatment for schizophrenia or 22q11 deletion syndrome in a subject, the method comprising:
(a) determining the level of miR-338-3p in thalamic neurons or a bodily fluid sample obtained from the subject before the treatment,
(b) determining the level of miR-338-3p in thalamic neurons or a bodily fluid sample obtained from the subject after the treatment,
(c) comparing the levels determined in steps (a) and (b), and
(d) determining that the treatment is effective if the level of miR-338-3p in thalamic neurons or the bodily fluid of the subject has increased after the treatment.

In another aspect, the invention provides a method for determining the likelihood of developing a positive symptom of schizophrenia (e.g., hallucinations, delusions, disorganized thought, or psychosis) in a subject, the method comprising:
(a) determining the level of miR-338-3p in thalamic neurons or a bodily fluid sample obtained from the subject,
(b) comparing the level determined in step (a) to a control level, and
(c) determining that the subject is at risk of developing a positive symptom of schizophrenia if the level of miR-338-

3p in thalamic neurons or the bodily fluid sample obtained from the subject is lower than the control level.

In one embodiment of any of the above diagnostic methods, the control is a predetermined standard, or the level of miR-338-3p in thalamic neurons of a healthy age- and gender-matched subject or an average value for several such subjects.

In one embodiment of any of the above diagnostic methods, the bodily fluid is selected from the group consisting of blood (e.g., whole blood, blood lymphocytes, peripheral blood mononuclear cells (PBMCs), blood plasma, or blood serum), urine, saliva, and cerebrospinal fluid (CSF).

In one embodiment of any of the above diagnostic methods, the level of miR-338-3p is determined using a method selected from the group consisting of hybridization, array-based assays, PCR-based assays (e.g., qPCR), and sequencing.

In one embodiment of any of the above diagnostic methods, prior to determining miR-338-3p level, miRNA is purified from the sample isolated from the subject.

In one embodiment of any of the above diagnostic methods, the method further comprises the step of reducing or eliminating degradation of miRNA.

In one embodiment of any of the above diagnostic methods, the miR-338-3p comprises the sequence UCCAGCAUCAGUGAUUUUGUUG (SEQ ID NO: 1). In one embodiment of any of the above diagnostic methods, the miR-338-3p consists of the sequence UCCAGCAUCAGUGAUUUUGUUG (SEQ ID NO: 1). In one embodiment of any of the above methods of the invention, the subject is human. In another embodiment of any of the above methods of the invention, the subject is an experimental animal model.

In a related aspect, the invention provides a kit for determining the likelihood of developing a positive symptom of schizophrenia comprising primers and/or probes specific for miR-338-3p.

In another related aspect, the invention provides a kit for determining efficacy of a treatment for schizophrenia or 22q11 deletion syndrome comprising primers and/or probes specific for miR-338-3p.

In one embodiment, the kits of the invention comprise miRNA isolation and/or purification means.

In one embodiment, the kits of the invention comprise instructions for use.

In another aspect, the invention provides the use of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p in the manufacture of a medicament in the treatment and/or prevention of schizophrenia.

In yet another aspect, the invention provides the use of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p in the manufacture of a medicament in the treatment of 22q11 deletion syndrome.

In a further aspect, the invention provides the use of (i) miR-338-3p or a mimic or a functional derivative thereof (including functional fragments of miR-338-3p and their derivatives), or (ii) a vector expressing said miR-338-3p or mimic or functional derivative thereof, or (iii) an agent capable of increasing the level or activity of miR-338-3p in the manufacture of a medicament in the treatment and/or prevention of a positive symptom of schizophrenia.

In one embodiment of any of the above aspects, the invention further provides the use of In another aspect, the invention provides a pharmaceutical composition comprising miR-338-3p or a mimic or a functional derivative thereof (including functional fragments of miR-338-3p and their derivatives) and a pharmaceutically acceptable carrier or excipient. In one embodiment, said composition is suitable for intranasal administration. In another embodiment, said composition is suitable for systemic administration.

In a related aspect, the invention provides a pharmaceutical dosage form comprising miR-338-3p or a mimic or a functional derivative thereof (including functional fragments of miR-338-3p and their derivatives) and a pharmaceutically acceptable carrier or excipient. In one embodiment, said dosage form is suitable for intranasal administration. In another embodiment, said dosage form is suitable for systemic administration.

These and other aspects of the present invention will be apparent to those of ordinary skill in the art in the following description, claims and drawings.

DETAILED DESCRIPTION OF THE INVENTION

Figure 1A:
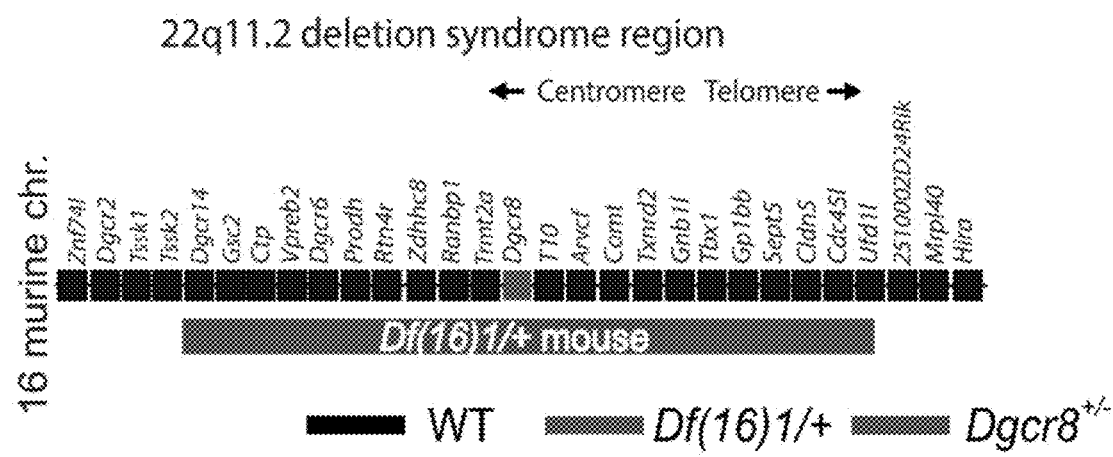
FIG. 1a-1n. Adult onset of antipsychotics sensitivity and synaptic transmission disruption in auditory TC projections of mouse models of 22q11DS. (a) Map of 22q11DS orthologs deleted in Df(16)1/+ mice. (b) Illustration of voltage-clamp recordings of thalamorecipient L3/4 pyramidal neurons in TC slices. TC projections are shown in red. ACx, auditory cortex; TC, thalamocortical; MGv, ventral part of the medial geniculate nuclei. (c, d, e) Late onset of Drd2 elevation in the auditory thalamus and TC synaptic transmission disruption in 22q11DS mice. (c, d) Input-output relations between stimulation intensity and EPSCs at TC projections in the ACx of 2- (c) or 4-month-old (d) WT (black) mice and Df(16)1/+ (white) mice. (e) Drd2 transcript levels in the MGV of 2- and 4-month-old WT (left black bar) and Df(16)1/+ mice (right gray bar) (numbers of mice are shown inside columns). (f, g) The effect of haloperidol on TC EPSCs in 2- (f) and 4-month-old (g) WT (black) and Df(16)1/+(white) littermates. Haloperidol-induced percentage change ($\Box$H) in the slope of TC EPSCs relative to baseline (before haloperidol application; dashed line). (h) The $\Box$H as a function of mouse age in WT (black) and Df(16)1/+(white) littermates. (i, j) The effect of haloperidol on TC EPSCs in 2-(i) and 4-month-old (j) WT (black) and Dgcr8$^{+/-}$ (gray) littermates. (k) The $\Box$H as a function of mouse age in WT (black) and Dgcr8$^{+/-}$ (gray) littermates. (l) Average Drd2 mRNA levels normalized to Gapdh in the auditory thalamus of 2- and 4-month-old WT (left black bar) and Dgcr8$^{+/-}$ littermates (right gray bar). (m, n) Mean PPI of maximal acoustic-startle response in 2-(m) and 4-month-old (n) WT (left black bar) and Dgcr8$^{+/-}$ (right gray bar) littermates. For the 2-month experiment (m), 23 WT mice and 22 Dgcr8$^{+/-}$ mice were used; in the 4-month experiment (n), 36 WT mice and Dgcr8$^{+/-}$ mice were used. Scale bars, 50 pA, 10 ms. Insets show representative EPSCs before (1) and after (2) haloperidol application. Numbers of mice or neurons are shown inside the columns or parenthesis, with the number of WT mice/neurons first. Data are represented as the mean±SEM. SPL (sound pressure level), *p<0.05.

The present invention is based on an unexpected discovery by the inventor that miR-338-3p miRNA is depleted in 22q11 deletion syndrome (which in 30% cases leads to schizophrenia) and this leads to abnormal elevation of Drd2 in the thalamus. This renders thalamic neurons sensitive to antipsychotics.

As further demonstrated herein, replenishment of miR-338-3p normalizes the Drd2 level and rescues abnormal function of thalamic neurons and their abnormal sensitivity to antipsychotics. Thalamic knockdown or deletion of miR-338-3p mimics 22q11DS molecular, synaptic, and behavioral auditory abnormalities, and more importantly, does so regardless of age. This result suggests that thalamic miR-338-3p is the crucial mediator and the late-onset controller of a pathogenic pathway underlying the positive symptoms of schizophrenia.

Based on these observations, the invention provides a targeted therapy against positive symptoms of schizophrenia that is devoid of side-effects attributable to antipsychotics, which therapy comprises replenishment of miR-338-3p in the thalamus.

Definitions

As used herein, the term "schizophrenia" includes a condition generally described as schizophrenia or a condition having symptoms related thereto. Schizophrenia can be considered a disease with a spectrum of manifestations with various threshold levels. Symptoms of schizophrenia may appear in a range of related disorders including classical schizophrenia as well as dementia, bipolar disorder, obsessive compulsive disorder (OCD), panic disorder, phobias, acute stress disorder, adjustment disorder, agoraphobia without history of panic disorder, alcohol dependence (alcoholism), amphetamine dependence, brief psychotic disorder, cannabis dependence, cocaine dependence, cyclothymic disorder, delirium, delusional disorder, dysthymic disorder, generalized anxiety disorder, hallucinogen dependence, major depressive disorder, nicotine dependence, opioid dependence, paranoid personality disorder, Parkinson's disease, schizoaffective disorder, schizoid personality disorder, schizophreniform disorder, schizotypal personality disorder, sedative dependence, shared psychotic disorder, smoking dependence and social phobia.

In the present application, the terms "microRNA", "miRNA" and "miR" are used interchangeably to refer to a class of small approximately 20-25 nt long non-coding RNA molecules. They play important roles in the regulation of target genes through sequence-specific hybridization to the 3' untranslated region (UTR) of messenger RNAs (mRNA) to repress their translation or regulate degradation (Griffiths-Jones Nucleic Acids Research, 2006, 34, Database issue: D140-1144; Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research, 102, 3-9; He et al., 2004, Nat. Rev. Genet., 5, 522-531; and Ying et al., 2004, Gene, 342, 25-28). Most miRNAs are transcribed by RNA polymerase II from intergenic, intronic or polycistronic loci to long primary transcripts, called pri-miRNAs. vPri-miRNAs are processed sequentially first in the nucleus (usually by the Drosha-DGCR8 complex) to approximately 70-100 nt pre-miRNA hairpin structures and then in the cytoplasm by the Dicer (ribonuclease III-like nuclease enzyme)-TRBP complex to approximately 2-25 nt miRNA duplexes (van Rooij and Kauppinen, EMBO Mol Med., 2014, 6(7): 851-864). In the cytoplasm, miRNA duplexes are incorporated into an Argonaute protein-containing miRNA-induced silencing complex (miRISC), followed by unwinding of the duplex and retention of the mature miRNA strand in miRISC, while the complementary strand is released and degraded (van Rooij and Kauppinen, EMBO Mol Med., 2014, 6(7): 851-864). miRNAs guide the miRISC to target mRNAs by base pairing imperfectly with their 3'-UTRs, leading to translational repression and/or degradation of the mRNA targets. The miRNA target sites, located in the 3'UTR of mRNAs, are often imperfectly matched to the miRNA sequence. Frequently, one miRNA can target multiple mRNAs and one mRNA can be regulated by multiple miRNAs targeting different regions of the 3' UTR. The 5' region of miRNA, also known as the "seed" region (nt 2-7), is the most critical sequence for targeting and function. Unless otherwise noted, the name of a specific miRNA refers to a mature miRNA sequence. Under current nomenclature rules, human miR-NAs are preceded with the prefix "hsa-" (i.e., an abbreviation for *Homo sapiens*). Throughout the specification and figures the hsa- prefix may be dropped for purposes of abbreviation, thus, for example, "hsa-miR-338-3p" and "miR-338-3p" would represent the same RNA sequence.

The present invention relates to miR-338, which is encoded within the intronic region of the gene for apoptosis-associated tyrosine kinase (AATK). It has been reported that miR-338 may downregulate genes which have a downstream negative effect on AATK expression. The sequence of the mature human miR-338-3p is 5'UCCAGCAUCA-GUGAUUUUGUUG3' (SEQ ID NO: 1).

As defined herein, the term "functional derivative" of a miRNA refers to a miRNA that has less than 100% identity to a corresponding wild-type miRNA and possesses one or more biological activities of the corresponding wild-type miRNA. Examples of such biological activities include, but are not limited to, inhibition of expression of a target RNA molecule (e g, inhibiting translation of a target mRNA molecule and/or modulating the stability of a target mRNA molecule) and inhibition of a cellular process associated therewith. These functional derivatives include species variants and variants that are the consequence of one or more mutations (e.g., a substitution, a deletion, an insertion) in a miRNA-encoding gene. In certain embodiments, the variant is at least about 70%, 75%, 80%, 85%, 90%, 95%, 98%, or 99% identical to a corresponding wild-type miRNA. Functional derivatives also encompass "functional fragments" of miRNA, i.e., portions of miRNA which are less than the full-length molecule (and their species and mutant variants) and that possess one or more biological activities of a corresponding wild-type miRNA. In certain embodiments, the biologically-active fragment is at least about 5, 7, 10, 12, 15, or 17 nucleotides in length.

As used herein, the term "miRNA mimic" refers to a double-stranded miRNA-like RNA fragment. Such miRNA mimic is designed to have its 5'-end bearing a partially complementary motif to the selected sequence in the 3'UTR unique to the target mRNA. Once introduced into cells, miRNA mimic, mimicking an endogenous miRNA, can bind to its target mRNA and inhibit its translation and/or modulate its stability. Unlike endogenous miRNAs, miR-mimics can be made to act in a gene-specific fashion by increasing the region of perfect complementarity with mRNA 3' UTR. Often, miRNA mimics are made to harbor chemical modifications to improve stability and/or cellular uptake (Rooij and Kauppinen, EMBO Mol Med., 2014, 6(7): 851-864). In such double-stranded miRNA mimics, the strand identical to the miRNA of interest is the guide (antisense) strand, while the opposite (passenger or sense) strand is less stable and can be linked to a molecule, such as, e.g., cholesterol, to enhance cellular uptake. In addition, the passenger strand may contain chemical modifications to prevent RISC loading, while it is further left unmodified to ensure rapid degradation. Since the miRISC needs to recognize the guide strand as a miRNA, the chemical modifications that can be used for the guide strand are limited. For example, the 2'-fluoro (2'-F) modification helps to protect against exonucleases, hence making the guide strand more stable, while it does not interfere with RISC loading (Rooij and Kauppinen, EMBO Mol Med., 2014, 6(7): 851-864).

The terms "vector", "expression vector", and "expression construct" are used interchangeably to refer to a composition of matter which can be used to deliver a nucleic acid of interest to the interior of a cell and mediate its expression within the cell. Most commonly used examples of vectors are autonomously replicating plasmids and viruses (such as, e.g., adenoviral vectors, adeno-associated virus vectors (AAV), lentiviral vectors, Sindbis virus vectors, etc.). An expression construct can be replicated in a living cell, or it can be made synthetically. In one embodiment, an expression vector comprises a promoter operably linked to a polynucleotide (e.g., a polynucleotide encoding miR-338-3p or its derivative or mimic) which promoter controls the initiation of transcription by RNA polymerase and expression of the polynucleotide. Typical promoters for mammalian cell expression include, e.g., SV40 early promoter, CMV immediate early promoter (see, e.g., U.S. Pat. Nos. 5,168,062 and 5,385,839), mouse mammary tumor virus LTR promoter, adenovirus major late promoter (Ad MLP), herpes simplex virus promoter, murine metallothionein gene promoter, and U6 or H1 RNA pol III promoter. Non-limiting examples of promoters useful for expression miRNA338-3p in the methods of the present invention include, e.g., Synapsin promoter (neuron specific), CamKIIa promoter (specific for excitatory neurons), CMV promoter, and β-actin promoter. These and other promoters can be obtained from commercially available plasmids, using techniques well known in the art. See, e.g., Sambrook et al., supra. Enhancer elements may be used in association with promoters to increase expression levels of the vectors. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression vector. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include, e.g., an Internal Ribosome Entry Site (IRES) present in the leader sequences of picornaviruses such as the encephalomyocarditis virus (EMCV) UTR (Jang et al. J. Virol. (1989) 63:1651-1660. Other useful picornavirus UTR sequences include, e.g., the polio leader sequence, hepatitis A virus leader and the hepatitis C IRES.

In certain embodiments of the invention, the cells containing nucleic acid constructs of the present invention may be identified in vitro or in vivo by including a marker in the expression vector. Such markers would confer an identifiable change to the cell permitting easy identification of cells containing the expression vector. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., green fluorescent protein (GFP), EGFP, or Dronpa), or immunologic markers can also be employed. Further examples of selectable markers are well known to one of skill in the art.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease. Within the meaning of the present invention, the term "treat" also encompasses preventing and/or reducing a positive symptom associated with schizophrenia or 22q11 DS, such as, e.g., hallucinations, delusions, disorganized thought, or psychosis.

As used herein the term "therapeutically effective" applied to dose or amount refers to that quantity of a compound or pharmaceutical composition that is sufficient to result in a desired activity (e.g., decrease in positive symptoms associated with schizophrenia and/or 22q11DS) upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like. An appropriate "effective" amount in any individual case may be determined by one of ordinary skill in the art using routine experimentation, based upon the information provided herein.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "combination" of a composition of the invention and at least a second pharmaceutically active ingredient means at least two, but any desired combination of compounds can be delivered simultaneously or sequentially (e.g., within a 24 hour period). It is contemplated that when used to treat various diseases, the compositions and methods of the present invention can be utilized with other therapeutic methods/agents suitable for the same or similar diseases. Such other therapeutic methods/agents can be co-administered (simultaneously or sequentially) to generate additive or synergistic effects. Suitable therapeutically effective dosages for each agent may be lowered due to the additive action or synergy.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

An "individual" or "subject" or "animal", as used herein, refers to humans, veterinary animals (e.g., cats, dogs, cows, horses, sheep, pigs, etc.) and experimental animal models of schizophrenia or 22q11 DS. In a preferred embodiment, the subject is a human.

The term "associated with" is used to encompass any correlation, co-occurrence and any cause-and-effect relationship.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean within an order of magnitude, preferably within 50%, more preferably within 20%, still more preferably within 10%, even more preferably within 5%, and most preferably within 1% of a given value or range. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It must be noted that, as used in this specification and the appended claims, the singular forms "a," "an" and "the" include plural referents unless the content clearly dictates otherwise.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Therapeutic Methods of the Invention

In one embodiment, the present invention provides a method for treatment and/or prevention of schizophrenia in a subject in need thereof, the method comprising administering to the subject a therapeutically effective amount of (i) miR-338-3p or a mimic or a functional derivative (including functional fragments) thereof, or (ii) a vector expressing said miR-338-3p or mimic or functional derivative thereof, or (iii) an agent capable of increasing the level or activity of miR-338-3p. In another embodiment, the invention provides a method for treatment of 22q11 deletion syndrome in a subject in need thereof, the method comprising administering to the subject a therapeutically effective amount of (i) miR-338-3p or a mimic or a functional derivative thereof, or (ii) a vector expressing said miR-338-3p or mimic or functional derivative thereof, or (iii) an agent capable of increasing the level or activity of miR-338-3p. In yet another embodiment, the invention provides a method for treatment of a positive symptom of schizophrenia in a subject in need thereof, the method comprising administering to the subject a therapeutically effective amount of (i) miR-338-3p or a mimic or a functional derivative thereof, or (ii) a vector expressing said miR-338-3p or mimic or functional derivative thereof, or (iii) an agent capable of increasing the level or activity of miR-338-3p. In one embodiment, the miR-338-3p or mimic or derivative thereof targets Drd2, e.g., Drd2 present in the thalamus. In another embodiment, the miR-338-3p or mimic or derivative thereof mediates TC disruption, e.g., by mediating the Dgcr8-Drd2 mechanism.

The therapeutic methods of the invention encompass over-expressing miR-338-3p, functional derivatives thereof or miR-338-3p mimics, e.g., using viral constructs, or using sense-based oligonucleotides or modified-oligonucleotide mimics (e.g., technologies from miRNA Therapeutics and miRagen Therapeutics), or inhibiting negative or activating positive miRNA regulators (transcriptional or epigenetic), etc.

The miR-338-3p can be expressed from recombinant viral vectors. The recombinant viral vectors of the invention comprise sequences encoding the miR-338-3p and any suitable promoter for expressing the RNA sequences. Typical promoters for mammalian cell expression include, e.g., SV40 early promoter, CMV immediate early promoter (see, e.g., U.S. Pat. Nos. 5,168,062 and 5,385,839), mouse mammary tumor virus LTR promoter, adenovirus major late promoter (Ad MLP), herpes simplex virus promoter, murine metallothionein gene promoter, and U6 or H1 RNA pol III promoter. Non-limiting examples of promoters useful for expression miRNA338-3p in the methods of the present invention include, e.g., Synapsin promoter (neuron specific), CamKIIa promoter (specific for excitatory neurons), CMV promoter, and β-actin promoter. Cell-type- or tissue-specific promoters can be used to express miRNA to allow for cell type- or tissue-specific expression. For example, the recombinant viral vectors of the invention can comprise inducible or regulatable promoters for expression of the miR-338-3p in thalamic neuronal cells.

Any viral vector capable of accepting the coding sequences for the miR-338-3p can be used. For example, vectors derived from adenovirus (AV), adeno-associated virus (AAV), retroviruses (e.g., lentiviruses (LV), Rhabdoviruses, murine leukemia virus), Sindbis virus, herpes virus, and the like. The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to specifically target certain cells or tissues by engineering the vectors to express certain capsid protein serotypes. Currently, there are several AAV serotypes available that can be used for tissue enrichment based on natural tropism toward specific cell types and interaction between different cellular receptors and serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), J Virol 76:791801. A method for constructing the recombinant AV vector, and a method for delivering the vector into target cells, are also described in Xia et al. (2002), Nat. Biotech. 20:1006-1010. Suitable AAV vectors for expressing the miRNAs, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641.

Alternatively, the miR-338-3p can be expressed from recombinant circular or linear DNA plasmids using any suitable promoter, including inducible/regulatable promoters. In one embodiment, the miR-338-3p is expressed as RNA precursor molecules from a plasmid, and the precursor molecules are processed into the functional mature miR-338-3p by a suitable processing system, including, but not limited to, processing systems existing within the thalamic neurons. Other suitable processing systems include, e.g., the in vitro Drosophila cell lysate system (e.g., as described in U.S. Published Patent Application No. 2002/0086356 to Tuschl et al.) and the E. coli RNAse III system (e.g., as described in U.S. Published Patent Application No. 2004/0014113 to Yang et al.).

Selection of plasmids suitable for expressing miR-338-3p, methods for inserting nucleic acid sequences into the plasmid to express miR-338-3p, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508.

In one embodiment, a plasmid expressing the miR-338-3p comprises a sequence encoding a miR precursor RNA under the control of the excitatory neuron-specific promoter, such as CamKIIa. In another embodiment, a plasmid expressing the miR-338-3p comprises a sequence encoding a miRNA precursor RNA under the control of the CMV and/or □-actin (ubiquitous) promoter. In yet another embodiment, a plasmid expressing the miR-338-3p comprises a sequence encoding a miR precursor RNA under the control of a neuron specific Synapsin promoter.

In the therapeutic methods of the invention, miR-338-3p, mimics and functional derivatives thereof can be also administered directly. Such miR-338-3p, mimics and functional derivatives can be chemically synthesized or recombinantly produced using methods known in the art. In one embodiment, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

In some embodiments, of the invention, a synthetic miRNA contains one or more design elements. These design elements include, but are not limited to: (i) a replacement group for the phosphate or hydroxyl of the nucleotide at the 5' terminus of the complementary region; (ii) one or more sugar modifications. In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. In particular embodiments, the sugar modification is a 2'O-Me modification. In further embodiments, there is one or more sugar modifications in the first or last 2 to 4 residues of the complementary region or the first or last 4 to 6 residues of the complementary region. In a particular embodiment, miR-338-3p, mimics and functional derivatives are made resistant to degradation by nucleases, e.g., by incorporating one or more ribonucleotides that are modified at the 2'-position with fluoro, amino, alkyl, alkoxy, and O-allyl.

Delivery of miR-338-3p, mimics and functional derivatives thereof can be enhanced by complexing with liposome nanoparticles, exosomes, polyethyleneimine, or atelocollagen (Rooij and Kauppinen, EMBO Mol Med., 2014, 6(7): 851-864).

Liposomes can increase the blood half-life of the nucleic acids. Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369. The liposomes for use in the present methods can comprise a ligand molecule that targets the liposome to thalamic neurons. The liposomes for use in the present methods can also be modified so as to avoid clearance by the mononuclear macrophage system ("MIMS") and reticuloendothelial system ("RES"). Such modified liposomes have opsonization-inhibition moieties on the surface or incorporated into the liposome structure. In one embodiment, a liposome of the invention comprises both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016. Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; animated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive animation using Na(CN)BH3 and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects will efficiently accumulate these liposomes; see Gabizon, et al. (1988), Proc. Natl. Acad. Sci., USA, 18:6949-53. In addition, the reduced uptake by the RES lowers the toxicity of stealth liposomes by preventing significant accumulation of the liposomes in the liver and spleen.

In certain embodiments of the invention, the liposome may be complexed with a hemagglutinating virus (HVJ). This has been shown to facilitate fusion with the cell membrane and promote cell entry of liposome-encapsulated nucleic acids (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Exosomes are nano-sized vesicles (30-120 nm in size) produced by many cell types, including dendritic cells (DC), B cells, T cells, mast cells, epithelial cells, and tumor cells. These vesicles are formed by inward budding of late endosomes and are then released to the extracellular environment upon fusion with the plasma membrane. Exosomes can be isolated from cells (e.g., by centrifugation) and loaded with miRNA using, e.g., lipofectamine or electroporation.

Other expression constructs which can be employed to deliver miR-338-3p or a mimic or a functional derivative thereof into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

miR-338-3p or a mimic or a functional derivative thereof can be also administered in combination with a cationic lipid. Examples of cationic lipids include, but are not limited to, lipofectin, DOTMA, DOPE, and DOTAP. The publication of WO/0071096 describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787. Methods used for forming particles are also disclosed in U.S. Pat. Nos. 5,844,107, 5,877,302, 6,008,336, 6,077,835, 5,972,901, 6,200,801, and 5,972,900.

It is contemplated that when used to treat various diseases, the compositions and methods of the present invention can be combined with other therapeutic agents suitable for the same or similar diseases. Also, two or more embodiments of the invention may be also co-administered to generate additive or synergistic effects. When co-administered with a second therapeutic agent, the embodiment of the invention and the second therapeutic agent may be simultaneously or sequentially (in any order). Suitable therapeutically effective dosages for each agent may be lowered due to the additive action or synergy. As a non-limiting example, the invention can be combined with other therapies that decrease the positive symptoms of schizophrenia, e.g., antipsychotics.

Compositions and Methods of Administration

The invention provides that miR-338-3p or a mimic or a functional derivative thereof, or a vector expressing said miR-338-3p or mimic or functional derivative thereof, or an agent capable of increasing the level or activity of miR-338-3p can be administered to the subject to replenish the endogenous miR-338-3p that is down-regulated in thalamic neurons of the subjects suffering from schizophrenia and/or 22q11 DS. The invention further provides that the isolated miR-338-3p or a mimic or a functional derivative thereof, or a vector expressing said miR-338-3p or mimic or functional derivative thereof, or an agent capable of increasing the level or activity of miR-338-3p can be used as pharmaceutical compositions and can be optionally combined with other antipsychotics, therapeutic molecules and/or treatments. In certain embodiments, miR-338-3p, or a mimic or a functional derivative thereof, or a vector expressing said miR-338-3p or mimic or functional derivative thereof, or an agent capable of increasing the level or activity of miR-338-3p, is used before, during, and after antipsychotics in combination therapies for treating positive symptoms associated with schizophrenia and/or 22q11 DS. The invention encompasses any now known or later developed antipsychotics for treating schizophrenia and/or 22q11 DS.

miR-338-3p molecules or mimics or functional derivatives thereof can include one or more modifications (e.g., to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and LNA. Where the miRNA molecule is produced synthetically, or by in vitro transcription, a modified ribonucleoside may be introduced during synthesis or transcription. Non-limiting examples of modified base moieties include inosine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2, 6-di aminopurine. Non-limiting examples of modified sugar moieties include arabinose, 2-fluoroarabinose, xylulose, and hexose. Modified miRNAs may contain substituted sugar moieties comprising one of the following at the 2' position: OH, SH, SCH$_3$, F, OCN, O(CH$_2$)$_n$NH$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O-; S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified miRNAs may also have sugar mimetics such as cyclobutyls or other carbocyclics in place of the pentofuranosyl group. Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with CH$_2$—NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$ backbones (where phosphodiester is O—PO$_2$—O—CH$_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are modified miRNA molecules having morpholino backbone structures in which the bases are linked to 6-membered morpholine rings, which are connected to other morpholine-linked bases via non-ionic phosphorodiamidate intersubunit linkages. Morpholino miRNAs are highly resistant to nucleases and have good targeting predictability (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220). Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497). In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-0, 4'-C methylene bridge. This bridge restricts the flexibility of the ribofuranose ring and locks the structure into a rigid C3-endo conformation, conferring enhanced hybridization performance and exceptional biostability.

Modified miRNAs can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810) or blood-brain barrier (see, e.g., PCT Publication No. WO 89/10134), etc.

miR-338-3p or mimics or functional derivatives thereof used in the present invention can be synthesized by standard methods known in the art, e.g., by use of an automated synthesizer. Following chemical synthesis, miRNA molecules are deprotected and purified (e.g., by gel electrophoresis or HPLC). Alternatively, standard procedures may used for in vitro transcription of miRNA from DNA templates carrying RNA polymerase promoter sequences (e.g., T7 or SP6 RNA polymerase promoter sequences). See, e.g., Donzé and Picard, Nucleic Acids Res. 2002; 30:e46; and Yu et al., Proc. Natl. Acad. Sci. USA 2002; 99:6047-6052. miRNA molecules may be also formed within a cell by transcription of RNA from an expression construct introduced into the cell. The expression constructs for in vivo production of miRNA molecules comprise miRNA encoding sequences operably linked to elements necessary for the proper transcription of the miRNA encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The miRNA expression constructs can further comprise vector sequences that facilitate the cloning of the expression constructs. Standard vectors that maybe used in practicing the current invention are known in the art (e.g., pSilencer 2.0-U6 vector, Ambion Inc., Austin, Tex.).

In some embodiments, miR-338-3p or a mimic or a functional derivative thereof, or a vector expressing said miR-338-3p or mimic or functional derivative thereof, or an agent capable of increasing the level or activity of miR-338-3p, is formulated into a suitable pharmaceutical preparation such as, e.g., solution, suspension, tablet, dispersible tablet, pill, capsule, powder, sustained release formulation or elixir, for oral administration; sterile solution or suspension for parenteral administration; powdered or liquid spray, nose drops, a gel or ointment for intranasal administration; powdered or liquid spray for administration by inhalation; films for sublingual administration; patch for transdermal administration, etc. miR-338-3p or a mimic or a functional derivative thereof, or a vector expressing said miR-338-3p or mimic or functional derivative thereof, or an agent capable of increasing the level or activity of miR-338-3p, can be formulated into pharmaceutical compositions using any of the techniques and procedures known in the art (see, e.g., Ansel Introduction to Pharmaceutical Dosage Forms, Fourth Edition 1985, 126).

In the compositions, effective concentrations of miR-338-3p or a mimic or a functional derivative thereof, or a vector expressing said miR-338-3p or mimic or functional derivative thereof, or an agent capable of increasing the level or activity of miR-338-3p is (are) mixed with a suitable pharmaceutical carrier or vehicle.

Pharmaceutically acceptable derivatives include acids, bases, enol ethers and esters, salts, esters, hydrates, solvates and prodrug forms. A suitable derivative is selected such that its pharmacokinetic properties are superior with respect to at least one characteristic to the corresponding parent agent. The miR-338-3p, or its mimics, may be derivatized prior to formulation.

In one embodiment of the invention, miR-338-3p or a mimic or a functional derivative thereof, or a vector expressing said miR-338-3p or mimic or functional derivative thereof, or an agent capable of increasing the level or activity of miR-338-3p is administered intranasally. Compositions for intranasal administration can comprise one or more nasal delivery-enhancing agents. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity such as the brain) of miR-338-3p or a mimic or a functional derivative thereof, or a vector expressing said miR-338-3p or mimic or functional derivative thereof, or an agent capable of increasing the level or activity of miR-338-3p. Enhancement of mucosal delivery can thus occur by any of a variety of mechanisms, for example by increasing the diffusion, transport, persistence or stability of miR-338-3p or a mimic or a functional derivative thereof, or a vector expressing said miR-338-3p or mimic or functional derivative thereof, or an agent capable of increasing the level or activity of miR-338-3p, enzyme inhibition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and are further described hereafter.

The pharmaceutical compositions of the present invention can be administered intranasally as a powdered or liquid spray, nose drops, a gel or ointment, through a tube or catheter, by syringe, packtail, pledget or by submucosal infusion. The compositions for intranasal administration can be simple aqueous (e.g., saline) solutions. Alternatively, they can contain various additional ingredients which enhance stability and/or nasal delivery of miR-338-3p or a mimic or a functional derivative thereof, or a vector expressing said miR-338-3p or mimic or functional derivative thereof, or an agent capable of increasing the level or activity of miR-338-3p. Such additional ingredients are well known in the art. Non-limiting examples of useful additional ingredients for enhancing nasal delivery include, e.g., (a) aggregation inhibitory agents (e.g., polyethylene glycol, dextran, diethylaminoethyl dextran, and carboxy methyl cellulose), (b) charge modifying agents, (c) pH control agents, (d) degradative enzyme inhibitors (e.g., amastatin and bestatin [see, e.g., O'Hagan et al., Pharm. Res. 1990, 7: 772-776 and WO 05/120551]; pegylation with PEG molecules, preferably low molecular weight PEG molecules [e.g. 2 kDa; Lee et al., Calcif Tissue Int. 2003, 73: 545-549]); (e) mucolytic or mucus clearing agents (e.g., n-acetyl-cysteine, propylgallate and cysteine methionine dimmers, chaotropes [see, e.g., WO 04/093917]), (f) ciliostatic agents; (g) membrane penetration-enhancing agents, (h) modulatory agents of epithelial junction physiology, such as nitric oxide (NO) stimulators, chitosan, and chitosan derivatives; (i) vasodilator agents, (j) selective transport-enhancing agents, and (k) stabilizing delivery vehicles, carriers, supports or complex-forming agents. See, e.g., EP 037943, EP 094157, EP 173990, EP 214898, EP 215697, EP 327756, EP 490806, U.S. Pat. Nos. 4,476,116, 5,759,565, WO 04/093917 and WO 05/120551.

The activity or physical stability of miR-338-3p or a mimic or a functional derivative thereof, or a vector expressing said miR-338-3p or mimic or functional derivative thereof, or an agent capable of increasing the level or activity of miR-338-3p in aqueous solutions or lyophilized preparations can be enhanced by various additives such as, e.g., polyols (including sugars [e.g., sucrose and Ficoll 70]), amino acids, and various salts. For example, miR-338-3p or a mimic or a functional derivative thereof microparticles can be prepared by simply lyophilizing or spray drying a solution containing various stabilizing additives described above. A wide non-limiting range of suitable methods and anti-aggregation agents are available for incorporation within the compositions of the invention such as disclosed in WO 05/120551, Breslow et al. (J. Am. Chcm. Soc. 1 996; 118: 1 1678-11681), Breslow et al. (PNAS USA 1997; 94: 11156-11158), Breslow et al. (Tetrahedron Lett. 1 998; 2887-2890), Zutsh i et al. (Curr. Opin. Chem. Biol. 1998; 2: 62-66). Daugherty et al. (J. Am. Chem. Soc. 1999; 121: 4325-4333), Zutshi et al. (J. Am. Chem. Soc. 1997; 119: 484-4845), Ghosh et al. (Chem. Biol. 1997; 5: 439-445), Hamuro et al. (Angew. Chem. Int. Fd. Fngl. 1997; 36: 2680-2683), Alberg et al., Science 1993; 262: 248-250), Tauton et al. (J. Am. Chem. Soc. 1996; 1 1 8: 10412-10422), Park et al. (J. Am. Chem. Soc. 1999; 1 2 1: 8-1 3), Prasanna et al. (Biochemistry 1998; 37:6883-6893), Tiley et al. (J. Am. Chem. Soc. 1997; 119: 7589-7590), Judice et al. (PNAS USA 1997; 94: 13426-13430), Fan et al. (J. Am. Chem. Soc. 1998; 120: 8893-8894), Gamboni et al. (Biochemistry 1998; 37: 12189-12194).

Non-limiting examples of membrane penetration-enhancing agents useful in the intranasal compositions of the invention include, e.g., (i) a surfactant (e.g., Tween 80, Poloxamer 1 88, polysorbates; see also EP 490806, U.S. Pat. No. 5,759,565, and WO 04/093917), (ii) a bile salt or bile salt derivative (e.g., unsaturated cyclic ureas and Transcutol). (iii) a phospholipid or fatty acid additive, mixed micelle, liposome, or carrier, (iv) an alcohol, (v) an enamine, (vi) a nitric oxide donor compound (e.g., S-nitroso-N-acetyl-DF-penicillamine, NOR 1, NOR4, which are preferably co-administered with an NO scavenger such as carboxy-PITO or doclofenac sodium), (vii) a long-chain amphipathic molecule (e.g., dcacylmethyl sulfoxide, azone, sodium lauryl sulfate, oleic acid) (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodcxtrin or beta-cyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc., inclusive of their alkali metal or alkaline earth metal salts), (xv) an N-acctylamino acid or salt thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, polyoxyethylencalkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like; mixed micelles; glycerol esters of acetoacetic acid (e.g., glyceryl-1,3-diacetoacetate or 1,2-isopropylideneglycerine-3-acetoacetate) and triglycerides (e.g., amylodextrin, Estaram 299, Miglyol 810); cyclodcxtrins and β-cyclodextrin derivatives (e.g., 2-hydroxypropyl-p-cyclodextrin and heptakis (2,6-di-0-methyl-[3-cyclodextrin) which can be optionally formulated in an oleaginous base; and N-acetylamino acids (N-acetylalaninc, N-acetylphenylalaninc, N-acetylserine, N-acetylglycine, N-acetyllysine, N-acetylglutamic acid, N-acetylproline, N-acetylhydroxyproline, etc.) and their salts (alkali metal salts and alkaline earth metal salts), as well as other penetration-promoting agents that are physiologically compatible for intranasal delivery. See, e.g., WO04/093917, WO05/120551 and Davis and Ilium (Clin. Pharmacokinet. 2003, 42: 1107-1128).

Non-limiting examples of useful absorption enhancers include, e.g., surfactants, glycosides, cyclodextrin and glycols. Non-limiting examples of useful bioadhesive agents include, e.g., carbopol, cellulose agents, starch, dextran, and chitosan.

In various embodiments of the invention, miR-338-3p or a mimic or a functional derivative thereof, or a vector expressing said miR-338-3p or mimic or functional derivative thereof, or an agent capable of increasing the level or activity of miR-338-3p is combined with one or more of the nasal delivery-enhancing agents recited above. These nasal delivery-enhancing agents may be admixed, alone or together, with the nasal carrier and with miR-338-3p or a mimic or a functional derivative thereof, or a vector expressing said miR-338-3p or mimic or functional derivative thereof, or an agent capable of increasing the level or activity of miR-338-3p, or otherwise combined therewith in a pharmaceutically acceptable formulation or delivery vehicle. For nasal delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the nasal mucosa with long term use.

The useful delivery volume of the intranasal pharmaceutical compositions of the invention is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml. A solid composition may comprise from 1 to 30 mg carrier per dosage, more particularly 4 to 20 mg.

The liquid compositions of the invention may be prepared by bringing into intimate admixture miR-338-3p or a mimic or a functional derivative thereof, or a vector expressing said miR-338-3p or mimic or functional derivative thereof, or an agent capable of increasing the level or activity of miR-338-3p in the liquid carrier optionally together with the further ingredients, additives and/or agents. Preferably the resulting mixture is then lyophilized and dissolved in water or aqueous saline for use in a liquid form according to the invention. The solid nasal composition of the invention may be prepared in conventional manner. miR-338-3p or a mimic or a functional derivative thereof, or a vector expressing said miR-338-3p or mimic or functional derivative thereof, or an agent capable of increasing the level or activity of miR-338-3p may be admixed with the carrier particles, e.g., a polymer base or cellulose product in conventional manner, optionally with further ingredients, additives and/or agents as indicated above e.g. a mucosal delivery enhancing agent or surfactant such as disclosed. miR-338-3p or a mimic or a functional derivative thereof, or a vector expressing said miR-338-3p or mimic or functional derivative thereof, or an agent capable of increasing the level or activity of miR-338-3p may be in solution, e.g., an aqueous or alcoholic solution when being mixed with the carrier particles and the solvent evaporated, e.g., under freeze-drying or spray drying. Such drying may be effected under the conventional conditions. Alternatively, the mixture may be compacted or granulated and then be pulverized and/or sieved. If desired the particles may be coated. According to a preferred embodiment of the invention, the nasal composition is prepared by lyophilisation. A homogeneous solution, preferably aqueous, containing miR-338-3p or a mimic or a functional derivative thereof, or a vector expressing said miR-338-3p or mimic or functional derivative thereof, or an agent capable of increasing the level or activity of miR-338-3p and optionally containing further ingredients, additives and/or agents as discussed above, is prepared and then submitted to lyophilisation in analogy with known lyophilisation procedures, and to subsequent drying. The resulting powder may then be dissolved in a liquid excipient or nasal carrier before administration, e.g., to reconstitute nasal drops, gel or spray. Alternatively it may be administered as such in the form of lyophilized powder or it may be mixed with further ingredients, additives and/or agents as discussed above. For example, a lyophilized powder comprising miR-338-3p or a mimic or a functional derivative thereof, or a vector expressing said miR-338-3p or mimic or functional derivative thereof, or an agent capable of increasing the level or activity of miR-338-3p but free of any nasal carrier may be prepared and then admixed with the desired nasal carrier or mixture of nasal carriers.

The present invention encompasses any delivery device that is suitable for nasal administration of the compositions of the invention. Preferably, such means administers a metered dosage of the composition. The composition of the present invention may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-free sprays, compressed air nebulizers, metered-disc inhalers, insufflators and pressurized metered dose inhalers.

For administration of a liquid in drop form, compositions of the invention can be placed in a container provided with a conventional dropper/closure device, e.g., comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Krich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g. compressed air-, jet-, ultrasonic-, and piezoelectric nebulizers.

Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., Biol. Pharm. Bull. 2001; 24: 1411-1416.

If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

Delivery devices are important not only for delivering miR-338-3p or a mimic or a functional derivative thereof, or a vector expressing said miR-338-3p or mimic or functional derivative thereof, or an agent capable of increasing the level or activity of miR-338-3p, but also for providing an appropriate environment for storage. This would include protection from microbial contamination and chemical degradation. The device and formulation should be compatible so as to avoid potential leaching or adsorption.

The delivery device (or its packaging) can be optionally provided with a label and/or with instructions for use indicating that the composition should be used intranasally.

In another embodiment, the composition of the invention can be provided as a nasal insert having miR-338-3p or a mimic or a functional derivative thereof, or a vector expressing said miR-338-3p or mimic or functional derivative thereof, or an agent capable of increasing the level or activity of miR-338-3p dispersed therein. The insert may be retained in the naris, but flushed by the nasal mucus, and may be designed to release miR-338-3p or a mimic or a functional derivative thereof, or a vector expressing said miR-338-3p or mimic or functional derivative thereof, or an agent capable of increasing the level or activity of miR-338-3p at the same place in the naris. Suitable nasal insert types include nasal plugs, tampons and the like, further examples of nasal inserts, their characteristics and preparation are described in HP 490806.

The compounds and compositions of the invention may further comprise agents, which facilitate delivery across the blood brain barrier (BBB). Non-limiting examples of such useful agents include, e.g., an implantable reservoir (Omaya reservoir), polysialation, functionalized nanocarriers (e.g., nanoparticles coated with transferrin or transferrin receptor [TR] antibodies), exosomes, liposomes (e.g., liposomes coated with targeting molecules such as antibodies, Trojan Horses Liposomes [THL]), antibodies (e.g., antibodies against transferrin receptor [TR] or insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, receptor-associated protein, apolipoprotein E, melanotransferrin/p97, etc.

In one embodiment, in order to enhance brain delivery of miR-338-3p or a mimic or a functional derivative thereof, or a vector expressing said miR-338-3p or mimic or functional derivative thereof, or an agent capable of increasing the level or activity of miR-338-3p, the patient is treated in a manner so as to increase the selective permeability of the blood-brain barrier (BBB). Treatments to selectively increase the permeability of the BBB in a patient include, but are not limited to, the administration of about 1 to about 1000 μg/kg body weight, preferably about 10 to about 100 μg/kg body weight, of IGF-I (e.g., as a bolus injection to a patient about 0.5 to 10 hours, preferably about 1 hour, before the inhibitor administration).

The amount of miR-338-3p or a mimic or a functional derivative thereof, or a vector expressing said miR-338-3p or mimic or functional derivative thereof, or an agent capable of increasing the level or activity of miR-338-3p, administered and the regimen of administration depends on absorption, inactivation and excretion rates of the active agent, the physicochemical characteristics of the agent, the severity of the condition to be alleviated, the age, condition, body weight, sex and diet of the patient, the disease state, other medications administered, and other factors known to those of skill in the art. An effective amount to treat the disease would broadly range (e.g., between about 0.001 mg and about 2000 mg per kg body weight of the recipient per day), and may be administered as a single dose or divided doses.

It is to be further understood that for any particular subject, specific dosage regimens should be adjusted over time according to the individual need and the professional judgment of the person administering or supervising the administration of the compositions.

The compositions of the invention are intended to be administered by a suitable route, including by way of example and without limitation orally, parenterally (e.g., intravenously, subcutaneously, intramuscularly), intranasally, by inhalation, sublingually, and topically. miR-338-3p or a mimic or a functional derivative thereof, or a vector expressing said miR-338-3p or mimic or functional derivative thereof, or an agent capable of increasing the level or activity of miR-338-3p, can be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection; subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the brain and/or within thalamic neurons), and/or via viral vector (e.g., AAV and/or lentiviral vector) mediated delivery.

The compositions are in liquid, semi-liquid or solid form and are formulated in a manner suitable for each route of administration.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN®80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, croscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein.

Briefly, an inhibitor of Nt5e or A1R is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethyl ene-vinyl acetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethyl ene/vinyl alcohol copolymer, ethyl ene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

miR-338-3p or a mimic or a functional derivative thereof, or a vector expressing said miR-338-3p or mimic or functional derivative thereof, or an agent capable of increasing the level or activity of miR-338-3p may be formulated as aerosols for application e.g., by inhalation or intranasally (e.g., as described in U.S. Pat. Nos. 4,044,126, 4,414,209, and 4,364,923). These formulations can be in the form of an aerosol or solution for a nebulizer, or as a microtine powder for insufflation, alone or in combination with an inert carrier such as lactose. In such a case, the particles of the formulation will, by way of example and without limitation, have diameters of less than about 50 microns, such as less than about 10 microns.

The agents may be also formulated for local or topical application, such as for application to the skin and mucous membranes (e.g., intranasally), in the form of nasal solutions, gels, creams, and lotions.

Other routes of administration, such as transdermal patches are also contemplated herein. Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

miR-338-3p or a mimic or a functional derivative thereof, or a vector expressing said miR-338-3p or mimic or functional derivative thereof, or an agent capable of increasing the level or activity of miR-338-3p may be packaged as articles of manufacture containing packaging material and a label that indicates that miR-338-3p or a mimic or a functional derivative thereof, or a vector expressing said miR-338-3p or mimic or functional derivative thereof, or an agent capable of increasing the level or activity of miR-338-3p, or pharmaceutically acceptable derivative thereof, are used for replenish miR-338-3p in thalamic neurons for rescue abnormal function of thalamic neurons and their abnormal sensitivity to antipsychotics, so as to treat one or more positive symptoms of schizophrenia and/or 22q11 DS.

In one embodiment of any of the above compositions, the composition further comprises an inhibitor of Drd2, including an inhibitor of the expression of Drd2, now known or later discovered. In one embodiment of any of the above compositions, the composition further comprises an activator of Dcgr8, including an activator of the expression of Dcgr8, now known or later discovered.

Diagnostic Methods of the Invention

In one embodiment, the invention provides a method for determining efficacy of a treatment for schizophrenia or 22q11 deletion syndrome in a subject, the method comprising:
(a) determining the level of miR-338-3p in thalamic neurons or in a bodily fluid sample obtained from the subject before the treatment,
(b) determining the level of miR-338-3p in thalamic neurons of the subject after the treatment,
(c) comparing the levels determined in steps (a) and (b), and
(d) determining that the treatment is effective if the level of miR-338-3p in thalamic neurons or in the bodily fluid sample obtained from the subject has increased after the treatment.

In another embodiment, the invention provides a method for determining the likelihood of developing a positive symptom of schizophrenia in a subject, the method comprising:
(a) determining the level of miR-338-3p in thalamic neurons or in a bodily fluid sample obtained from the subject,
(b) comparing the level determined in step (a) to a control level, and
(c) determining that the subject is at risk of developing positive symptoms of schizophrenia if the level of miR-338-3p in thalamic neurons or in the bodily fluid sample obtained from the subject is lower than the control level.

In the diagnostic methods of the invention, the level of miR-388-3p is measured in a biological sample obtained from the subject. For example, a brain tissue sample can be removed from the subject, and neurons can be isolated by standard techniques. Alternatively, a bodily fluid sample can be used. Non-limiting examples of useful bodily fluids for determination of the levels of miR-338-3p include, e.g., blood, urine, saliva, CSF. The blood sample may comprise whole blood, blood lymphocytes, peripheral blood mononuclear cells (PBMCs), blood plasma, or blood serum. The identification of miRNA expression in the blood sample will typically take place ex vivo, but the present invention also contemplates in vivo testing.

A corresponding control sample can be obtained from a healthy age- and gender-matched subject or a population of such healthy subjects. The control sample is then processed along with the sample from the subject, so that the levels of miR-338-3p in the subject's sample can be compared to the corresponding miR-338-3p levels from the control sample. A reference miRNA expression standard for the biological sample can also be used as a control.

The level of miR-338-3p in a sample can be measured using any technique that is suitable for detecting RNA levels in a biological sample. Suitable techniques include hybridization (e.g., Northern blot analysis, in situ hybridization), array-based assays, PCR-based assays, and sequencing. Array-based assays include, e.g., commercial arrays from Agilent, Exiqon, Affymetrix or custom-designed two-color arrays with a common reference (e.g., a specific quantity of 'artificial' miRNA for all probes on the chip or a specific sample such as, e.g., large batches of RNA isolated from patient blood, etc), or solution hybridization assays such as Ambion mirVana miRNA Detection Kit). Sequencing methods include, e.g., direct sequencing by one of the next generation sequencing technologies (e.g., Helicos small RNA sequencing, miRNA BeadArray (Illumina), Roche 454 (FLX-Titanium), and ABI SOLiD). For review of additional applicable techniques see, e.g., Chen et al., BMC Genomics, 2009, 10:407; Kong et al., J Cell Physiol. 2009; 218:22-25.

In a particular embodiment, the level of at least one miR-338-3p is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7.

Suitable probes for Northern blot hybridization of miR-338-3p can be produced from the nucleic acid sequences provided in the figures and include, but are not limited to, probes having at least about 70%, 75%, 80%, 85%, 90%, 95%, 98%, 99% or complete complementarity to miR-338-3p. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylyated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. Suitable probes for in situ hybridization of a given miRNA can be produced from the nucleic acid sequences, and include, but are not limited to, probes having at least about 70%, 75%, 80%, 85%, 90%, 95%, 98%, 99% or complete complementarity to a miRNA of interest, as described above.

The relative number of miRNA molecules in cells can also be determined by reverse transcription of miRNA, followed by amplification of the reverse-transcribed transcripts by polymerase chain reaction (RT-PCR). Non-limiting examples of useful commercial RT-PCR assays include Taqman miRNA assays (stem-loop assays; Applied Biosystems) and LNA-based miRNA PCR assays (poly-A-based assays; Exiqon) or quantitative RT-PCR based array method (qPCR-array). Other methods of amplification include ligase chain reaction (LCR), transcription-mediated amplification (TMA), strand displacement amplification (SDA) and nucleic acid sequence based amplification (NASBA).

The levels of miRNA can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

Useful methods of miRNA isolation and purification, include, e.g., Qiazol or Trizol extraction or the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), concentration and purification on anion-exchangers, magnetic beads covered by RNA-binding substances, or adsorption of certain miRNA on complementary oligonucleotides.

In some embodiments, miRNA degradation in patients' samples is reduced or eliminated. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecyl sulphate (SDS), or a combination thereof. Air-exposure-related RNA degradation can be reduced, e.g., by storage of samples in an inert air environment, performing RNA extraction within 3-4 days from the time of sample collection to minimize air-related RNA degradation, or minimizing time to tissue fixation. Reducing miRNA degradation in samples is particularly important when sample storage and transportation is required prior to miRNA quantification.

In one embodiment of any of the above methods, the method further comprises determining the level of Dcgr8 and/or Drd2 expression, such as for example and not limitation, by hybridization (including protein and nucleic acid hybridization assays, e.g., ELISA, Western blotting, Northern blotting, Southern blotting), array-based assays, PCR-based assays (e.g., qPCR), and sequencing.

Kits of the Invention

In conjunction with the above diagnostic methods, the present invention also provides various kits comprising primers and/or probes specific for miR-338-3p. The kits of the invention can be useful, e.g., for diagnosing schizophrenia or for determining efficacy of a treatment for schizophrenia or 22q11 deletion syndrome.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Materials and Methods

Animals.

Mice of both sexes were used for all experiments. Df(16) 1/+ and Dgcr8$^{+/-}$ mouse strains were reported previously[40,68] and were back-crossed onto the C57BL/6J genetic background for at least 10 generations. The miR-338$^{+/-}$ and miR-338$^{-/-}$ mice were generated from embryonic stem cells from C57BL/6N-A$^{tm1Brd}$ mice that were purchased from the Mutant Mouse Regional Resource Center (MMRRC; clone #034476-UCD). C57BL/6 blastocyst injections were performed by the Transgenic/Gene Knockout Shared Resource at St. Jude Children's Research Hospital (St. Jude). Chimeric mice were genotyped according to MMRRC protocols by using the following primers: 5' common reverse (ATAGCATACATTATACGAAGTTATCACTGG; SEQ ID NO: 39), 5' gene-specific (CTTCACTACACTCTCCCTAGTACAGTCTC; SEQ ID NO: 40), 3' common forward (TCTAGAAAGTATAGGAACTTCCATGGTC; SEQ ID NO: 41), and 3' gene-specific (AGGAGACTCATAGTTCTCTGTATCATAGC SEQ ID NO: 42). PCR was performed under the following conditions: 93° C. for 3 min, 93° C. for 15 s, and 68° C. for 9 min for 8 cycles and then 93° C. for 15 s, 60° C. for 30 s, and 68° C. for 9 min for 32 cycles. The mutant allele generated a 6.1-kb band with 5' common-reverse and 5' gene-specific primers and a 4.1-kb band with 3' common-forward and 3' gene-specific primers. The wild-type (WT) allele did not generate a band with either primer set. Subsequent genotyping was performed at Transnetyx (Cordova, Tenn.). For the majority of experiments, mice were divided into groups according to genotype or viral injections, and the experimenters were blinded to the genotype or treatment. The care and use of animals were reviewed and approved by the St. Jude Institutional Animal Care and Use Committee.

Whole-Cell Electrophysiology.

Acute primary thalamocortical (TC) slices (400-μm thick) containing the left auditory cortex (ACx) and the left ventral part of the medial geniculate nuclei (MGv) of the thalamus were prepared as previously described[5]. Briefly, mouse brains were quickly removed and placed in cold (4° C.) dissecting artificial cerebrospinal fluid (ACSF) containing 125 mM choline-Cl, 2.5 mM KCl, 0.4 mM CaCl$_2$, 6 mM MgCl$_2$, 1.25 mM NaH$_2$PO$_4$, 26 mM NaHCO$_3$, and 20 mM glucose (300-310 mOsm), with 95% O$_2$/5% CO$_2$. Primary TC slices were obtained from the left hemisphere by using a slicing angle of 15°. After a 1-h incubation in ACSF [125 mM NaCl, 2.5 mM KCl, 2 mM $CaCl_2$, 2 mM $MgCl_2$, 1.25 mM $NaH_2PO_4$, 26 mM $NaHCO_3$, 20 mM glucose (300-310 mOsm), with 95% $O_2$/5% $CO_2$] at room temperature, the slices were transferred into the recording chamber and superfused (2-3 mL/min) with warm (30-32° C.) ACSF.

Whole-cell recordings were obtained from cell bodies of layer (L) 3/4 thalamorecipient neurons in the ACx and thalamic-relay neurons in the MGv. Mice were chosen in a pseudorandom order, without the experimenter's prior knowledge of genotype or treatments. Patch pipettes (open-pipette resistance, 3.5-5 MΩ) were filled with an internal solution containing 125 mM $CsMeSO_3$, 2 mM CsCl, 10 mM HEPES, 0.1 mM EGTA, 4 mM MgATP, 0.3 mM NaGTP, 10 mM $Na_2$ creatine phosphate, 5 mM QX-314, 5 mM tetra-ethylammonium Cl (pH 7.4 adjusted with CsOH, 290-295 mOsm). Voltage-clamp recordings were made using a Multiclamp 700B (Molecular Devices, Sunnyvale Calif.), digitized (10 kHz), and recorded using the pCLAMP 10.0 software (Molecular Devices, Sunnyvale Calif.). EPSCs were recorded at holding membrane potentials of −70 mV. In all experiments, membrane potentials were corrected for a liquid junction potential of −10 mV. TC excitatory postsynaptic currents (EPSCs) were evoked by current pulses (duration, 100 μs) delivered to the thalamic radiation via tungsten bipolar electrodes. Paired-pulse ratio (PPR) of TC and corticocortical (CC) EPSCs and the NMDAR/AMPAR ratio were measured as described previously[39]. To ensure consistent access resistance of the recording electrode during long-term experiments, the peak amplitude of a brief (10-ms) hyperpolarizing test pulse (−5 mV) was monitored, which was given 250 ms after a stimulus. Access resistance (Ra) in recorded neurons was typically 10 to 25 MΩ. Recordings were discarded if the access resistance was higher than 25 MΩ, or if it changed more than 15% during the course of the whole-cell recording.

Two-Photon Imaging.

Two-photon laser-scanning microscopy was performed using an Ultima imaging system, a Ti:sapphire Chameleon Ultra femtosecond-pulsed laser, and 60× (0.9 NA) water-immersion infrared objectives (Coherent, Santa Clara, Calif.). Synaptically evoked calcium transients were measured in dendritic spines, the site of thalamic inputs, as described previously[81]. Briefly, Alexa Fluor 594 (30 μM) and Fluo-5F (300 μM) (ThermoFischer Scientific) were included in the internal pipette solution (see above) and were excited at 820 nm. Synaptically evoked changes in fluorescence of both fluorophores were measured in the line-scan mode (750 Hz) in spine heads and the parent dendritic shaft. Line scans were analyzed as changes in green (G, Fluo-5F) fluorescence normalized to red (R, Alexa Fluor 594) fluorescence (ΔG/R). The amplitude and probability of calcium transients were measured in response to 10 to 20 stimulations delivered at 0.1 Hz to the thalamic radiation. Distance (angular) of the active thalamic inputs from the center of the soma was calculated using maximum-intensity projections of z-scan images of the entire cell collected at lower magnification.

Optogenetics.

In optogenetic experiments, the light-activated cation channel ChR2 was expressed in the MGv by using adeno-associated virus (AAV) and optically induced EPSCs were evoked by briefly illuminating TC slices with a 473-nm light[116]. AAVs were generated from the pAAV-CaMKIIα-hChR2(H134R)—YFP-WPRE-pA (CaMKIIα-ChR2-YFP) plasmid and produced commercially (UNC Vector; serotype 2/1; 4×10[12] IFU/mL). AAVs were injected into the MGv as described previously[79]. Adult mice were anesthetized with isoflurane in pure oxygen, and a 200- to 400-nL sample of virus was slowly pressure-injected into the MGv (from the bregma: anterior-posterior, −3.0 mm; medial-lateral, ±2.0 mm; dorsal-ventral, 3.1 mm). Approximately 21 to 28 days after virus injection, the mice were decapitated, and TC slices were prepared. Confocal imaging of YFP in the MGv was used to verify on-target infection of CamKIIα-ChR2-YFP viruses. Short light pulses (10-200 mW) from a 473-nm laser were directed to the slices through the visible light photoactivation module or through the objective.

Slice Electrophysiology.

Acute primary thalamocortical (TC) slices (400 μm thick) containing the auditory cortex (ACx) and the ventral part of the medial geniculate nuclei (MGv) of the thalamus were prepared as previously described[6]. Briefly, mouse brains were quickly removed and placed in cold (4° C.) dissecting artificial cerebrospinal fluid (ACSF) containing 125 mM choline-Cl, 2.5 mM KCl, 0.4 mM $CaCl_2$, 6 mM $MgCl_2$, 1.25 mM $NaH_2PO_4$, 26 mM $NaHCO_3$, and 20 mM glucose (300-310 mOsm), with 95% $O_2$/5% $CO_2$. Primary TC slices were obtained from the left hemisphere by using a slicing angle of 15°. After a 1 hour incubation in ACSF (125 mM NaCl, 2.5 mM KCl, 2 mM $CaCl_2$, 2 mM $MgCl_2$, 1.25 mM $NaH_2PO_4$, 26 mM $NaHCO_3$, 20 mM glucose [300-310 mOsm], with 95% $O_2$/5% $CO_2$) at room temperature, the slices were transferred into the recording chamber and superfused (2-3 mL/min) with warm (30-32° C.) ACSF.

Whole-cell recordings were obtained from cell bodies of layer (L) 3/4 thalamorecipient neurons in the ACx and thalamic-relay neurons in the MGv. Patch pipettes (open pipette resistance, 3.5-5 MΩ) were filled with an internal solution containing 125 mM $CsMeSO_3$, 2 mM CsCl, 10 mM HEPES, 0.1 mM EGTA, 4 mM MgATP, 0.3 mM NaGTP, 10 mM $Na_2$ creatine phosphate, 5 mM QX-314, 5 mM tetra-ethylammonium Cl (pH 7.4 was adjusted with CsOH, 290-295 mOsm). Voltage-clamp recordings were made using a Multiclamp 700B, digitized (10 kHz), and recorded using the pCLAMP 10.0 software. EPSCs were recorded at holding membrane potentials of −70 mV. In all experiments, membrane potentials were corrected for a liquid junction potential of −10 mV. TC EPSCs were evoked by current pulses (duration, 100 μs) delivered to the thalamic radiation via tungsten bipolar electrodes. To ensure consistent access resistance of the recording electrode during long-term experiments, the peak amplitude of a brief (10-ms) hyperpolarizing test pulse (−5 mV) was monitored given 250 ms after a stimulus. Access resistance (Ra) in recorded neurons was typically 10 to 25 MΩ. Recordings were discarded if access resistance was higher than 25 MΩ or if access resistance changed more than 15% during the course of the whole-cell recording.

miRNA Microarray.

Total RNA was isolated from 2- and 4-month-old male WT, Df(16)1/+, and Dgcr8[+/−] thalami containing MGv using mirVana RNA isolation kit (Life Technologies, Carlsbad, Calif.). Total RNAs (100 ng) were labeled using miRNA Complete Labeling and Hyb Kit (Agilent, Santa Clara, Calif.), followed by hybridizing to the Mouse miRNA v19 microarray (Agilent-046065) that contains 3,105 unique biological featured probes targeting 1,247 mature miRNAs according to mouse miRBase version 19.0 (www.mirbase.org; August 2012). Microarrays were scanned by using an Agilent array scanner (G2565CA) at 3-μm resolution. Microarray data were extracted by Agilent Feature Extraction software (v.10.5.1.1). The data process was performed using Partek software (St. Louis, Mo.).

After quantile normalization among arrays, each probe was summarized by averaging with a single normalized intensity value. The Student's t-test was used to determine statistical significance between sets of replicates from different experimental groups. The miRNA was considered significantly differentially expressed if the p-value<0.01 and $\log_2$ fold change (FC)>0.2 for more than one probe targeting the mature form of the miRNA. The mRNAs targeted by differentially expressed miRNAs were predicted using bioinformatics tools miRWalk[76] and TargetScan (www.targetscan.org).

Quantitative RT-PCR.

Total RNA was isolated from various brain regions (i.e., the auditory thalamus containing the MGv, hippocampus, or cortex) by using mirVana RNA isolation Kit (Life Technologies, Carlsbad, Calif.). The synthesis of cDNA from mRNA was performed with iScript (Bio-Rad, Hercules, Calif.), and miRNA First-Strand cDNA Synthesis Kit (Agilent) was used to synthesize cDNA from miRNA. The experiments were performed using SYBR Green (Life Technologies, Carlsbad, Calif.). The following forward primers were used for miRNA analysis: mmu-miR-338-3p (TCCAGCATCA-GTGATTTTGTTG, SEQ ID NO: 2), hsa-miR-338-3p (TC-CAGCATCAGTGATTTTGTTG; SEQ ID NO: 44) mmu-miR-335-3p (TTTTTCATTATTGCTCCTGACC, SEQ ID NO: 3), mmu-miR-335-5p (TCAAGA GCAATAAC-GAAAAATGT, SEQ ID NO: 4), mmu-miR-337-3p (TCA-GCTCCTATATGATG CCTTT, SEQ ID NO: 5), mmu-miR-337-5p (CGGCGTCATGCAGGAGTTGATT, SEQ ID NO: 6), mmu-miR-3065-5p (TCAACAAAATCACTGAT-GCTGG, SEQ ID NO: 7), and mmu-miR-3065-3p (TCA-GCACCAGGATATTGTTGGGGm SEQ ID NO: 8).

The universal reverse-primer specific to the sequence tag (miRNA First-Strand cDNA Synthesis Kit; Agilent) was used. The following primers were used for mRNA analysis: Drd2 forward (GGATGTCATGATGTGCACAGC, SEQ ID NO: 9), Drd2 reverse (CGCTTGCGGAGAACGATG, SEQ ID NO: 10), Aatk forward (ATGCTGGCCTGCCTGTGT-TGT, SEQ ID NO: 11), and Aatk reverse (AGGGGCAG-GACATACACATCGG, SEQ ID NO: 12). The following loading controls were used: U6 snRNA forward (CGCT-TCGGCAGCACATATAC, SEQ ID NO: 13), U6 snRNA reverse (TTCACGAATTTGCGTGTCAT, SEQ ID NO: 14), SnoRNA202 (CTTTTGAACCCTTTTCCATCTG, SEQ ID NO: 15), and SnoRNA234 (TTAACAAAAATTCGTCAC-TACCA, SEQ ID NO: 16). The same universal reverse primer was used for SnoRNA202 and SnoRNA234. The same U6 snRNA primers were used for human and mouse samples. Samples from each mouse were run in triplicate.

Human Brain Tissue.

Postmortem samples of human MGv and ACx (Brodmann area 41) were obtained from The Maryland Brain Collection (Maryland Psychiatric Research Center, University of Maryland School of Medicine, Catonsville, Md.). The level of mature miR-338-3p wase tested in six patients with schizophrenia and six age-, race-, and sex-matched healthy controls. Only samples with RNA integrity number>7 were used in these experiments (Agilent RNA 6000 Nano kit). The mean postmortem interval was 15.8±1.8 h for patients with schizophrenia and 16.5±1.2 h (p>0.05) for healthy controls. Quantitative RT-PCR for each brain tissue sample was run in triplicate.

Plasmids and Viruses.

To overexpress miRNAs of interest, recombinant AAVs (serotype 5) were generated by cloning chimeric hairpins of the miRNAs of interest[31] with hsa-miR-30a into the 3' UTR of GFP under the CamKII☐ promoter using a previously described strategy[31]. The following primers were used: miR-338-3p-1 (GTACAGCTGTTGACAG TGAGC-GACTCCAGCATCAGTGATTTTGTTGTGTGAA, SEQ ID NO: 17), miR-338-3p-2 (CCATCTGTGGCTTCACA-CAACAAAATCACTGATGCTGGAGTCGCTCACTGT-CAACA GCT, SEQ ID NO: 18), miR-338-3p-3 (GCCACA-GATGGCAACAAAATCTGATGCTGGAG CTGCCTACTGCCTCGGAA, SEQ ID NO: 19), miR-338-3p-4 (AGCTTTCCGAGGCAGTA GGCAGCTCCAG-CATCAGATTTTGTTG, SEQ ID NO: 20), miR-337-3p-1 (GTACAGCTG TTGACAGTGAGCGACTCAGCTC-CTATATGATGCCTTTTGTGAA, SEQ ID NO: 21), miR-337-3p-2 (CCATCTGTGGCTTCACAAAAGGCAT-CATATAGGAGCTGAGTCGCTCACTGT CAACAGCT, SEQ ID NO: 22), miR-337-3p-3 (GCCACAGATG-GAAAGGCATCATAGGAG CTGAGCTGCCTACTGC-CTCGGAA, SEQ ID NO: 23), miR-337-3p-4 (AGCTTTC-CGAGG CAGTAGGCAGCTCAGCTCCTATGATGCCTTT, SEQ ID NO: 24), miR-337-5p-1 (GTACAG CTGTTGACAGT-GAGCGACCGGCGTCATGCAGGAGTTGATTTGT-GAA, SEQ ID NO: 25), miR-337-5p-2 (CCATCTGTG-GCTTCACAAATCAACTCCTGCATGACGCCGGTCG-CTC ACTGTCAACAGCT, SEQ ID NO: 26), miR-337-5p-3 (GCCACAGATGGAATCAAC TCGCATGACGCCG-GCTGCCTACTGCCTCGGAA, SEQ ID NO: 27), miR-337-5p-4 (AGCTTTCCGAGGCAGTAGGCAGCCGGCGTCATGC-GAGTTGATT, SEQ ID NO: 28), miR-335-3p-1 (GTACA-GCTGTTGACAGTGAGCGACTTTTTCATTATTGCTC-CTGACCTGT GAA, SEQ ID NO: 29), miR-335-3p-2 (CCATCTGTGGCTTCACAGGTCAGGA GCAATAAT-GAAAAAGTCGCTCACTGTCAACAGCT, SEQ ID NO: 30), miR-335-3p-3 (GCCACAGATGGGGTCAGGAGA-TAATGAAAAAGCTGCCTACTGCCTCGGAA, SEQ ID NO: 31), miR-335-3p-4 (AGCTTTCCGAGGCAGTAG-GCAGCTTTTTCATTATCTCCTG ACC, SEQ ID NO: 32), miR-335-5p-1 (GTACAGCTGTTGACAGTGAGCGACTC AAGAGCAATAACGAAAAATGTTGTAA, SEQ ID NO: 33), miR-335-5p-2 (CCATCTGT GGCTTCA-CAACATTTTTCGTTATTGCTCTTGAGTCGCTCACT-GTCAACAGCT, SEQ ID NO: 34), miR-335-5p-3 (GC-CACAGATGGACATTTTTCGATTGCTCTTGAGCTGC-CTACT GCCTCGGAA, SEQ ID NO: 35), and miR-335-5p-4 (AGCTTTCCGAGGCAG TAGGCAGCTCAAGAG-CAATCGAAAAATGT, SEQ ID NO: 36).

Generation of miR-338-3p sponges and *Renilla* and Firefly activity using the dual-luciferase reporter assay was performed as described previously[32,33]. Twelve copies of the following sequences were inserted for the miR-338-3p sponge (CAACAAAATGCGGATGCTGGA, SEQ ID NO: 37) or scrambled control (GACACTGTGAGCGAAGA-CATA, SEQ ID NO: 38) into the 3' UTR of GFP under the control of the CamKII☐ promoter. Recombinant AAVs ($1-2 \times 10^{13-14}$ particles/mL) were generated at the St. Jude Vector Development & Production Core and injected into the MGvs of anesthetized mice, as described previously[6].

In the luciferase assay, multiple copies of the miR-338-3p sponge and scramble control were cloned into 3'-UTR of *Renilla* luciferase gene contained within the psiCHECK-2 vector (Promega). The plasmids were transfected into HEK 293T cells along with miR-338-3p overexpression plasmid or control pcDNA3.1 or irrelevant miR-185-5p overexpressing plasmid. After two days in culture, *Renilla* and Firefly activities were measured using the dual-luciferase reporter assay (Promega) according to the manufacturer's instructions. The *Renilla* luciferase expression was normalized to Firefly luciferase expression as a readout.

Generation of miR-338 KO Mice.

Heterozygous embryonic stem cells from C57BL/6N-A$^{tm1Brd}$ mice were purchased from Mutant Mouse Regional Resource Center (clone #034476-UCD). C57BL/6 blastocysts injections were performed by the Transgenic/Gene Knockout Shared Resource at St. Jude Children's Research Hospital. Genotyping of chimeric mice was performed according to Mutant Mouse Regional Recourse Center protocols using the following primers: 5' common reverse (ATAGCATACATTATACGAAGTTATCACTGG, SEQ ID NO: 39), 5' gene-specific (CTTCACTACACTCTCCCTAG-TACAGTCTC, SEQ ID NO: 40), 3 ' common forward (TCTAGAAAGTATAGGAACTTCCATGGTC, SEQ ID NO: 41), and 3' gene-specific (AGGAGACTCATAGT-TCTCTGTATCATAGC, SEQ ID NO: 42). PCR conditions were a follows: 93° C. for 3 min, 93° C. for 15 s, and 68° C. for 9 min for 8 cycles and then 93° C. for 15 s, 60° C. for 30 s, 68° C. for 9 min for 32 cycles. Mutant allele generates a 6.1-kilobase band with 5' common reverse and 5' gene-specific primers, and 4.1-kilobase band with 3' common forward and 3' gene-specific primers. WT allele does not generate a band with either primer set. Subsequent genotyping was performed at Transnetyx (Cordova, Tenn.).

Mouse Behavioral Tests.

Prepulse (PPI) experiments were performed as previously described[6]. Briefly, each day before testing, the mice were transported from the animal-housing room and allowed a 1-h habituation period in the testing room. Before experiments were initiated, the mice were allowed to acclimate to the Plexiglas restraint chamber (6 cm×6 cm×4.8 cm) for 20 min. The mice then had a 5-min acclimation period to a 65-dB background white noise, which played throughout the session. For PPI experiments, three acoustic startles (8 kHz, 120 dB, 40 ms) were delivered separated by a 15-s intertrial interval. The testing session consisted of the following trials: pulse-alone, in which the startle pulse was presented; the combination of a 40-ms white-noise prepulse (74 dB, 82 dB, or 90 dB) in WT and Dgcr8$^{+/-}$ littermates and (70 dB, 80 dB, or 90 dB) in WT and miR-338$^{+/-}$ littermates and preceding the startle pulse by 100 ms, and no stimuli. Trials were separated by 15 s and presented in a pseudo-random order. PPI was calculated as follows: 100×(pulse-alone response−prepulse+pulse response)/pulse-alone response.

Auditory Brainstem Responses (ABR) experiments were performed as previously described[34, 86]. Briefly, mice were anesthetized with Avertin (0.6 mg/g bodyweight, i.p.) and ABR was measured using a Tucker Davis Technology (TDT) System III with RZ6 Multiprocessor and BioSigRZ software (Tucker Davis Technology, Alachua, Fla.). Sounds were delivered via the MF-1 speaker in the open-field configuration. ABR waveforms were recorded using subdermal needles placed at the vertex of the skull, below the pinna of the ear, and at the base of the tail. The needles were connected to a low impedance head-stage (RA4LI, TDT) and fed into the RZ6 multiprocessor through a pre-amplifier (RA4PA, Gain 20×, TDT) (Tucker Davis Technology, Alachua, Fla.). ABR waveforms were averages obtained from 500 presentations of a tone (21 tones/s) in the alternating phase and were band-pass filtered (300 Hz-3 kHz). The ABR threshold was defined as the minimum sound intensity that elicited a wave above the noise level. All ABR experiments were conducted in a sound booth (Industrial Acoustic Company, IAC, Model 120A double wall).

Statistical Analyses.

Data are represented as the means±SEM. All statistics were computed using the Sigma Plot software. Differences in mean data were determined by the t-test, Wilcoxon signed rank test, a one-way ANOVA followed by Student-Newman-Keuls post-hoc test, or a two-way ANOVA, followed by Holm-Sidak multiple comparisons and were considered significant at p<0.05.

Example 2: Delayed Disruption of TC Synaptic Transmission in 22q11DS Models: The Sensitivity of TC Projections and TC Excitatory Postsynaptic Currents (EPSCs) Measurements in Animal Models at Different Postnatal Ages In adult (4- to 5-month-old) Df(16)1/+ murine models[7, 15] of 22q11DS (FIG. 1a), a genetic disorder causing schizophrenia in approximately 30% of patients[10, 16], Dgcr8 haploinsufficiency causes deficient synaptic transmission in TC projections to the ACx[6], a brain region that is implicated in auditory hallucinations[17-19]. This deficiency is mediated by an aberrant elevation of Drd2 in the thalamic-relay neurons, which renders them abnormally sensitive to antipsychotics (Drd2 antagonists)[6].

Because the positive symptoms of schizophrenia arise during late adolescence or early adulthood, the sensitivity of TC projections to the antipsychotic agent haloperidol was compared in Df(16)1/+ mice (FIG. 1a) and their wild-type (WT) littermates at different postnatal ages, ranging from 1.5 to 7 months. Using single-cell recordings, TC excitatory postsynaptic currents (EPSCs) were measured from layer (L) 3/4 pyramidal neurons, the main thalamorecipient neurons in the ACx', while stimulating TC projections in acute brain slices containing the auditory thalamus (i.e., the ventral part of the medial geniculate nuclei [MGv]) and the ACx. TC projections in WT mice were not haloperidol-sensitive at any age, whereas Df(16)1/+TC projections became sensitive to haloperidol (1 □M) only at 3 months of age. In older mice (4 months or older), TC EPSCs in the presence of haloperidol increased approximately two fold compared to baseline TC EPSCs, whereas in younger mice (2 months or younger) TC EPSCs were not sensitive to haloperidol. The Drd2 mRNA level was elevated in the auditory thalamus of 4-month-old (haloperidol-sensitive age) but not 2-month-old (haloperidol-insensitive age) Df(16)1/+ mice, and the input-output relation of TC synaptic transmission was deficient in 4-month-old but not 2-month-old Df(16)1/+ mice. Consistent with the notion of a Dgcr8-miRNA-Drd2 mechanism of TC deficiency in 22q11DS[6], TC projections of Dgcr8$^{+/-}$ mice but not WT littermates were sensitive to haloperidol only after 3 months of age. Drd2 mRNA levels were also elevated in the thalamus of 4-month-old but not 2-month-old Dgcr8$^{+/-}$ mice. Impaired glutamate release at TC projections causes an abnormal flow of acoustic information to the ACx, resulting in a decreased acoustic-startle response and impaired prepulse inhibition (PPI) of acoustic startle[6], a measure of sensorimotor gating that is typically reduced in schizophrenic patients[21, 22]. Consistent with the notion of a late onset of schizophrenia symptoms, PPI deficits had a late onset, being present in 4-month-old but not 2-month-old Dgcr8$^{+/-}$ mice.

Figure 1B:
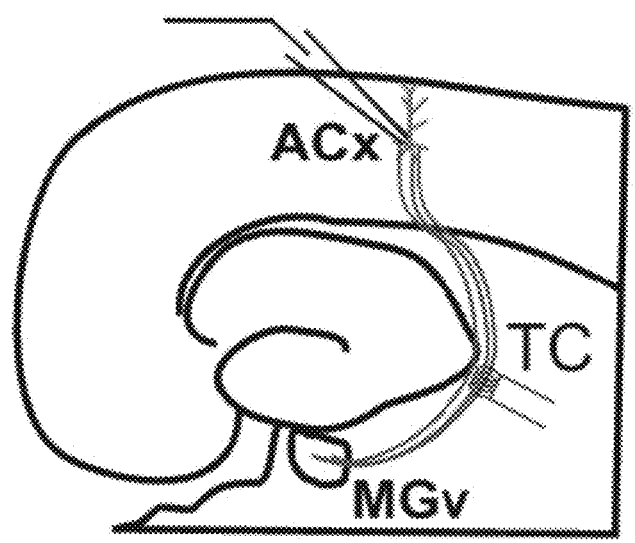
Figure 1C:
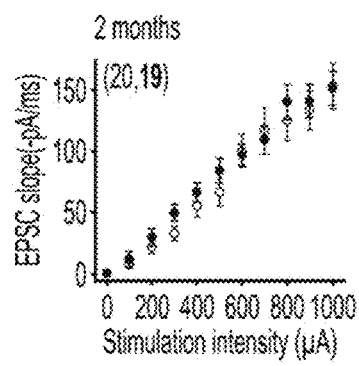
Figure 1D:
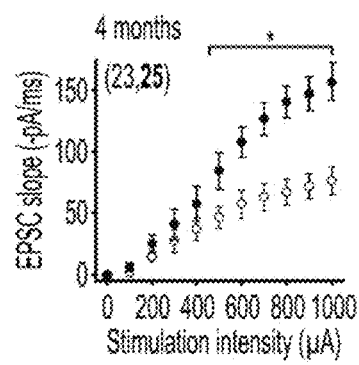
Figure 1E:
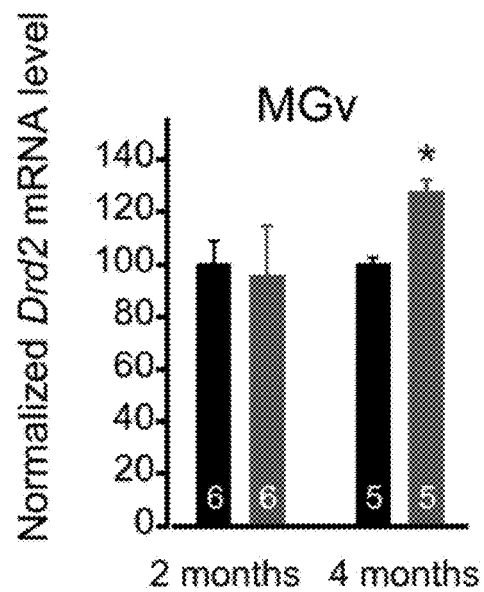

Basal synaptic transmission was compared in young (2-month-old) and mature (4-month-old) Df(16)1/+ mice, a murine model of 22q11DS[40] (FIG. 1a), and their wild-type (WT) littermates. Using whole-cell voltage-clamp recordings, TC excitatory postsynaptic currents (EPSCs) were measured from the cortical layer (L) 3/4 pyramidal neurons, the main thalamorecipient neurons in the ACx', while stimulating TC projections in acute brain slices containing the auditory thalamus (i.e., the ventral part of the medial geniculate nuclei [MGv]) and the ACx (FIG. 1b). The input-output relation between stimulation intensity and TC EPSC, a measure of basal synaptic transmission at TC projections, was deficient in older but not younger mutant mice (white circles) compared to WT (black circles) controls (FIG. 1c,1d). Consistent with the notion that the Drd2 elevation in thalamic-relay neurons reduces glutamatergic synaptic transmission at auditory TC projections in Df(16)1/+ mice[39], the Drd2 mRNA level was elevated in the MGv of older but not younger Df(16)1/+ mice (right gray bars compared to WT shown in the left black bars) (FIG. 1e).

Figure 1F:
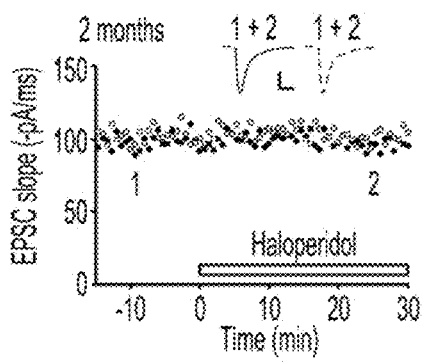
Figure 1G:
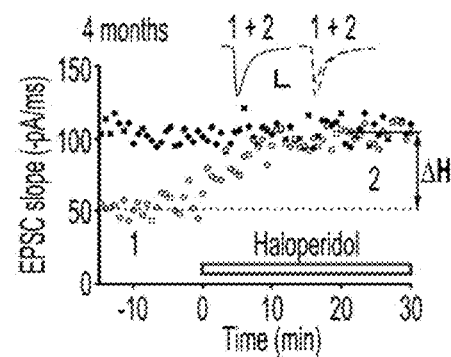
Figure 1H:
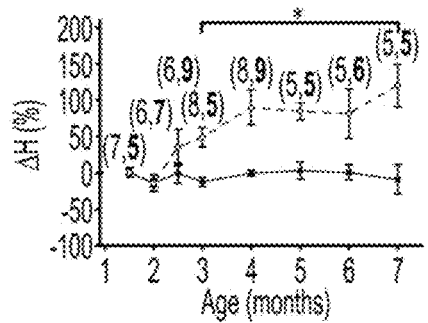

Elevated Drd2 levels in older Df(16)1/+ mice mediate the abnormal sensitivity of mutant TC projections to antipsychotics; thus, the time course of this sensitivity was tested at different postnatal ages (1.5-7 months). In brief, the thalamic radiation of WT mice was stimulated to evoke TC EPSCs with a rise slope of approximately 100 pA/ms. The effect of the antipsychotic agent haloperidol on TC EPSC 30 minutes after its bath application was compared to the preapplication baseline TC EPSC (AH). Using AH as a measure of haloperidol sensitivity, it was determined that TC projections in WT mice were not sensitive to haloperidol at any age. However, Df(16)1/+TC projections became sensitive to haloperidol (1 µM) in an age-dependent manner. The AH was significantly higher in Df(16)1/+ mice (white circles) than in WT littermates (black circles) but only beginning at 3 months of age (FIG. 1f-1h). In older mice, a similar intensity of thalamic stimulation (523±42 µA, n=31 in WT and 550±39 µA, n=30 in Df(16)/+ mice; p>0.05) applied to the thalamic radiation evoked substantially smaller TC EPSCs in Df(16)1/+ mice (white circles) compared to WT controls (black circles), and haloperidol rescued that deficit (FIG. 1f,1g). In contrast, TC projections in younger mutant mice (white circles) were not sensitive to haloperidol at similar stimulation intensities relative to WT mice (black circles) (527±61 µA, n=19 in WT and 568±50 µA, n=21 in Df(16)/+ mice; p>0.05) (FIG. 1h).

Figure 1I:
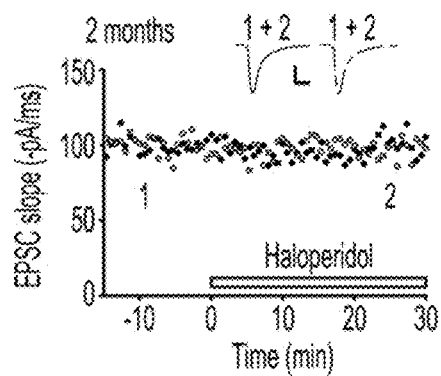
Figure 1J:
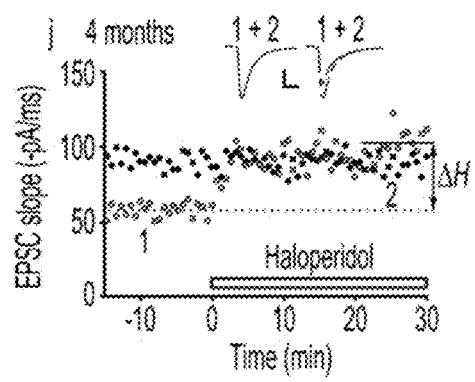
Figure 1K:
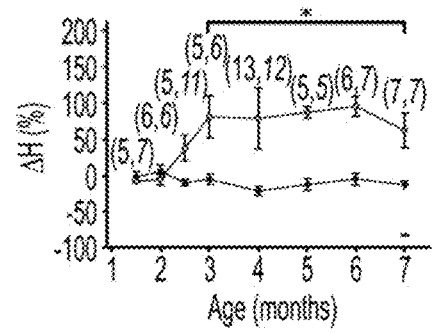
Figure 1L:
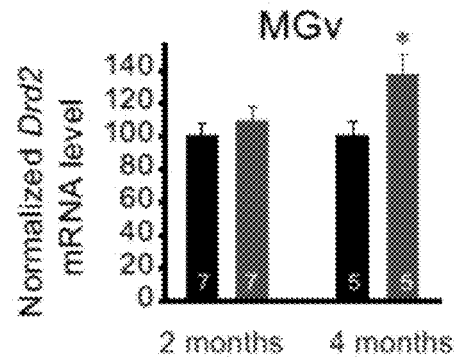
Figure 1M:
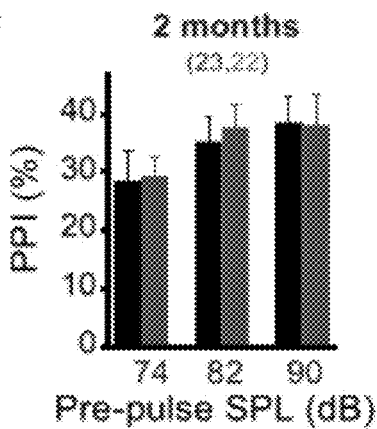
Figure 1N:
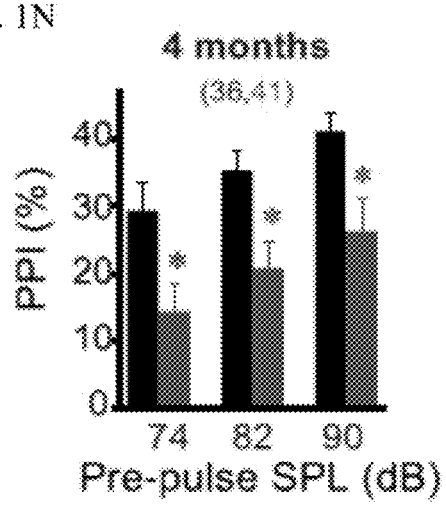

Consistent with the notion that Dgcr8 underlies the TC deficiency in 22q11DS[39], TC projections in Dgcr8$^{+/-}$ mice (gray circles) but not WT mice (black circles) were sensitive to haloperidol at older than 3 months of age, at similar stimulation intensities of the thalamic radiation (543±43 µA, n=36 in WT and 551±43 µA, n=37 in Dgcr8$^{+/-}$ mice; p>0.05). TC projections in younger mice were not sensitive to haloperidol (569±44 µA, n=16 in WT and 582±37 µA, n=24 in Dgcr8$^{+/-}$ mice; p>0.05) (FIG. 1i-1k). Drd2 mRNA levels were also elevated in the thalamus of only the older Dgcr8$^{+/-}$ mice (shown in right gray bars compared to WT, shown in left black bars) (FIG. 1l). Furthermore, the PPI, a measure of sensorimotor gating that is typically reduced in schizophrenic patients[74,75], was deficient in older but not younger Dgcr8$^{+/-}$ mice (shown in right gray bars compared to WT, shown in left black bars) (FIG. 1m,1n). These data indicate that the pathogenic Dgcr8-Drd2 mechanism of 22q11DS underlies the disruption of TC synaptic transmission but only later in life.

Figure 2A:
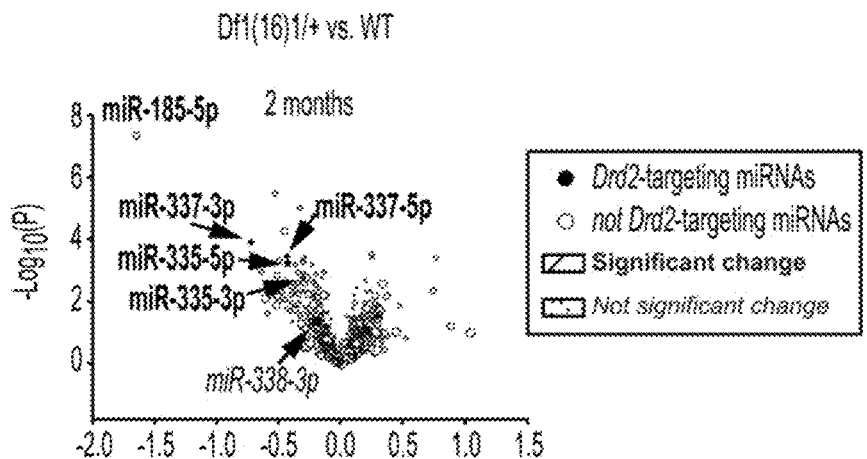
FIG. 2a-2j. Identification of Drd2-targeting miR-338-3p in the auditory thalamus. (a-d) Volcano plots of miRNA microarray data from the auditory thalamus of 2- (a, c) and 4-month-old (b, d) WT and Df(16)1/+ (a, b) and WT and Dgcr8$^{+/-}$ (c, d) male littermates. The difference between miRNA levels in WT and mutants was considered significant if p<0.01 and log$_2$ fold change (FC)>±0.2. Symbol size represents the miRNA expression level in the microarray. Note miR-338-3p had the highest expression among all predicted Drd2-targeting miRNAs. (e) Diagram of the mouse Drd2 3'UTR (XM_006509996.2; SEQ ID NO: 43) with seed sites for the 5 miRNAs indicated. (f) Experimental design of a recombinant AAV encoding a chimeric construct overexpressing an miRNA of interest (top) injected into the mouse MGv (bottom). (g) GFP expressed specifically in the auditory TC projections after in vivo injection of recombinant AAV. (h) Haloperidol sensitivity of TC projections in 4-month-old WT mice (left black bar) and Df(16)1/+ mice (right gray bar) previously injected with AAVs encoding different miRNAs or GFP. Only miR-338-3p eliminates haloperidol sensitivity in TC projections of Df(16)1/+ mice. Numbers of mice are indicated in parentheses above each bar; the left-hand number is the number of WT mice used and the right-hand number is the number of Df(16)1/+ mice used. (i) Relative average levels of miRNA expression in the thalamus, hippocampus, and cortex of WT mice (normalized to the average of three housekeeping genes: U6, snoRNA202, and snoRNA234). Only miR-338-3p shows enrichment in the thalamus. (j) Mean relative miR-338-3p levels (normalized to U6) in the postmortem MGv and ACx tissues from patients with schizophrenia (SCZ) (right gray bar) and healthy controls (left black bar). Six healthy controls and 6 patients with SCZ were used.
Figure 2B:
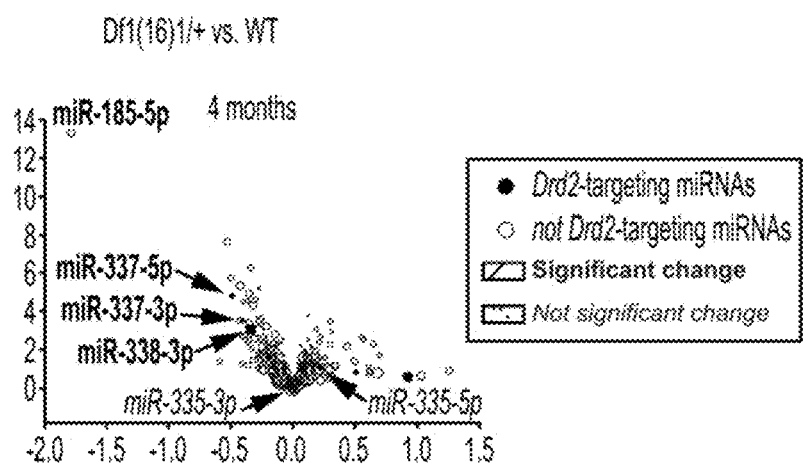
Figure 2C:
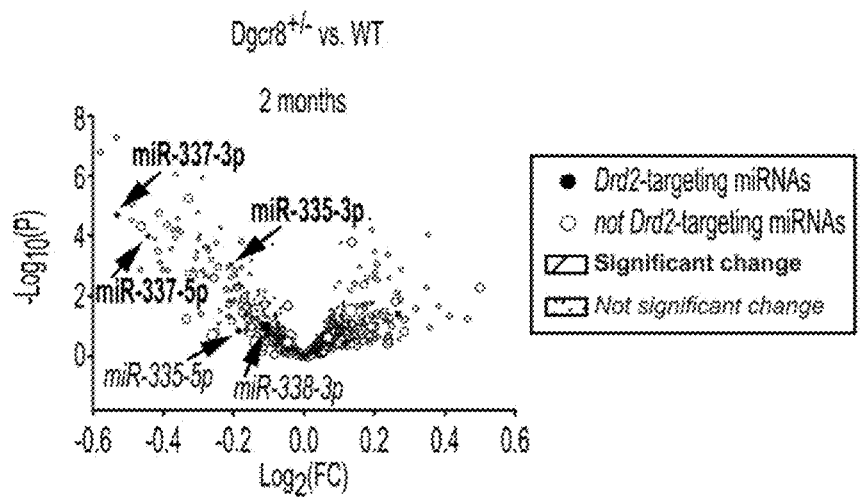
Figure 2D:
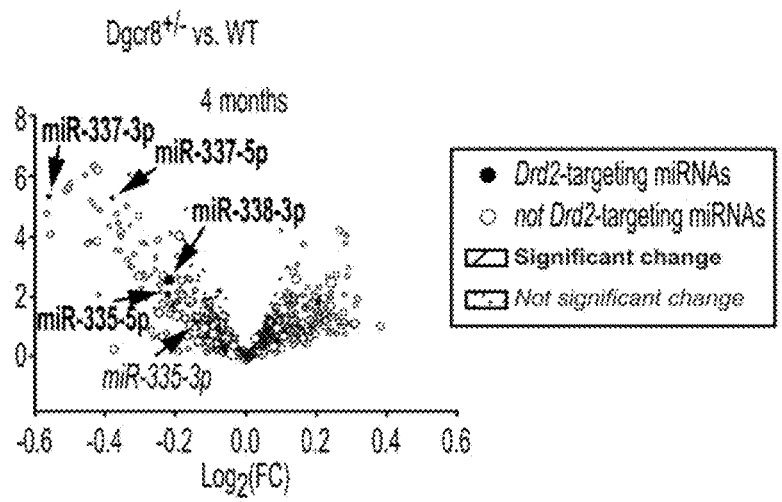
Figure 7:
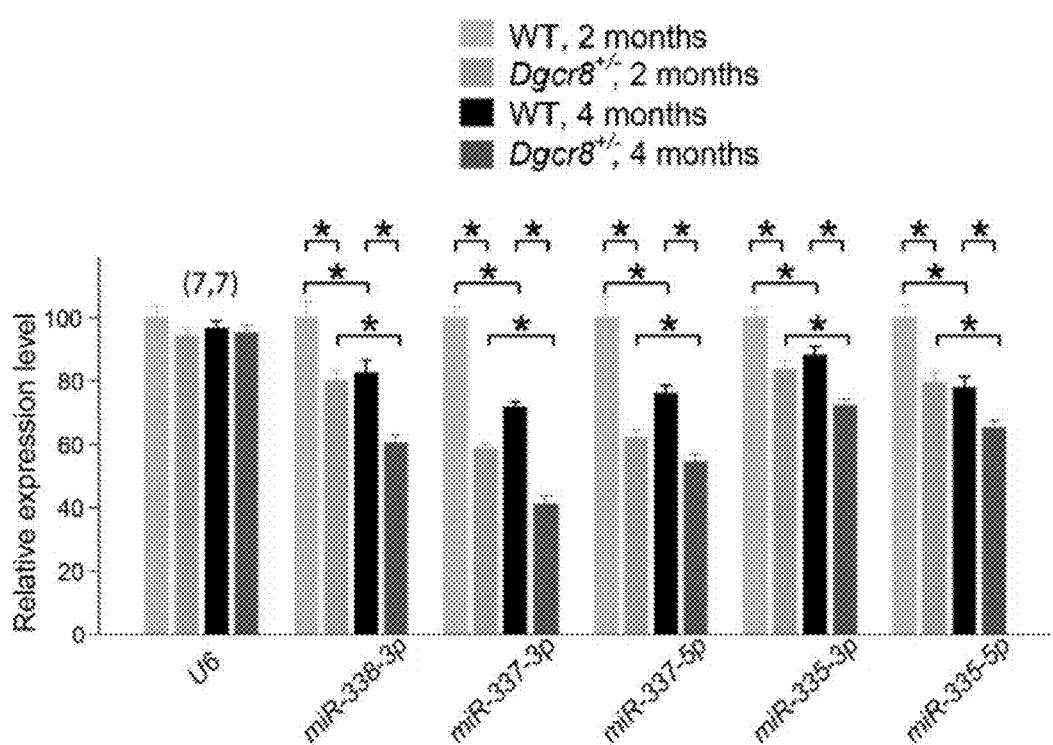
FIG. 7. QRT-PCR verification of depletion of five Drd2-targeting miRNAs in the MGv of Dgcr8$^{+/-}$ mice. Relative expression levels of the U6 loading control and Drd2-targeting miRNAs in the auditory thalamus of 2- and 4-month-old WT and Dgcr8$^{+/-}$ littermates. The left-most (lightest gray) bar for each miRNA corresponds to 2-month WT mice, followed by a lighter gray bar corresponding to 2-month Dgcr8$^{+/-}$ littermates, followed by a black bar corresponding to 4-month WT mice, followed by a dark gray bar corresponding to 4-month Dgcr8$^{+}$ littermates. Data are normalized to the 2-month-old WT levels for each miRNA. Data are represented as the mean±SEM. *p<0.05.
Figure 8A:
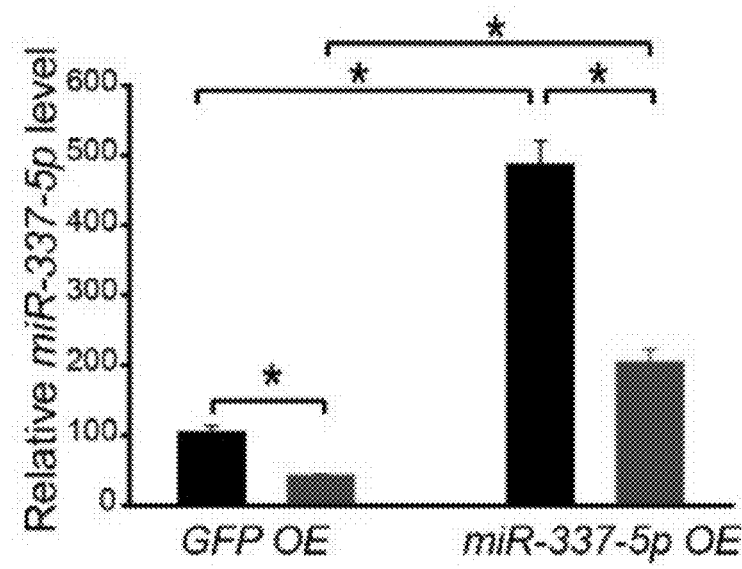
FIG. 8a-8k. MGv restoration of miR-338-3p but not other Drd2-targeting miRNAs eliminates abnormal haloperidol sensitivity of TC projections in 22q11DS mice. (a-e) Mean levels of miR-337-5p (a), miR-338-3p (b), miR-335-5p (c), miR-337-3p (d), and miR-335-3p (e) were normalized to the U6 loading control in the MGv of 4-month-old WT and Df(16)1/+ mice injected with AAVs overexpressing a control vector (GFP) or respective miRNAs (n=3-7 mice per experiment). The left black bar corresponds to WT mice while the right gray bar corresponds to Df(16)1/+ mice in each of a-e. (f-k) Mean TC EPSCs were normalized to baseline before and after haloperidol in 4-month-old WT and Df(16)1/+ mice injected with AAVs overexpressing a control vector (GFP) (f), miR-337-5p (g), miR-338-3p (h), miR-335-5p (i), miR-337-3p (j), or miR-335-3p (k) into the MGv. The black circles correspond to WT mice while the dark gray circles correspond to Df(16)1/+ mice in each of f-k. Insets show representative traces before (1) and during (2) the application of haloperidol. *p<0.05.
Figure 8B:
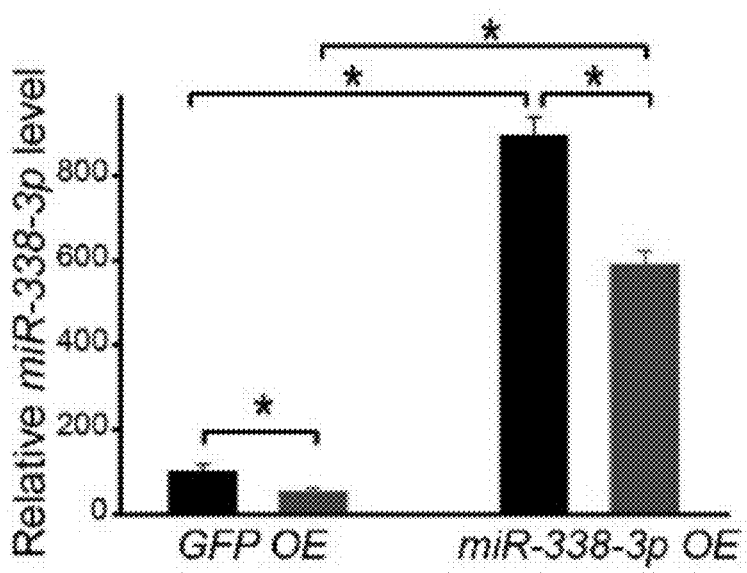
Figure 8C:
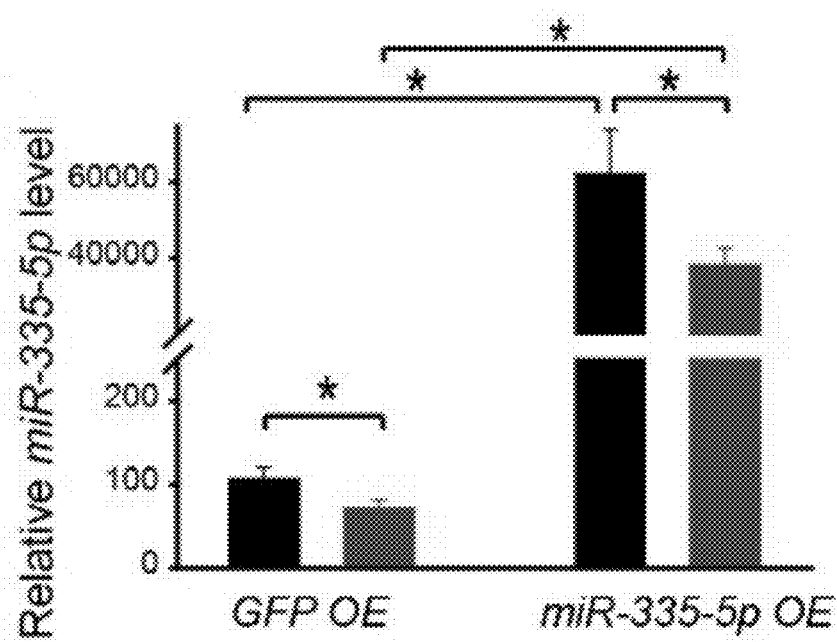
Figure 8D:
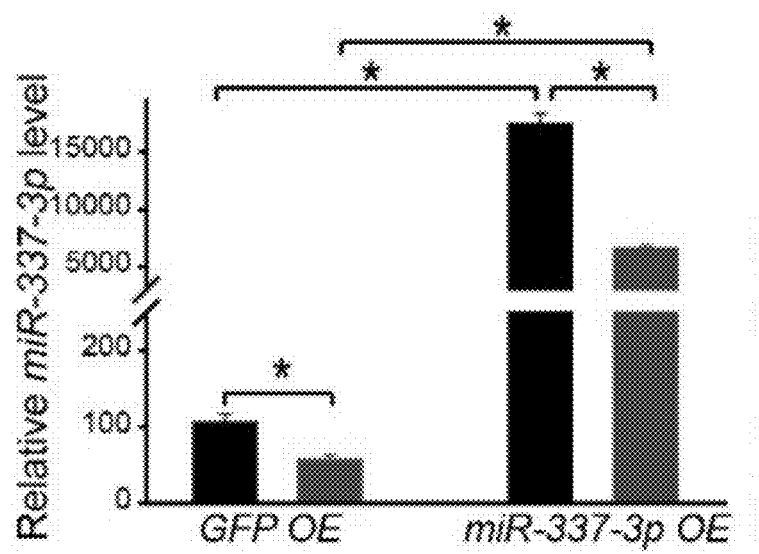
Figure 8E:
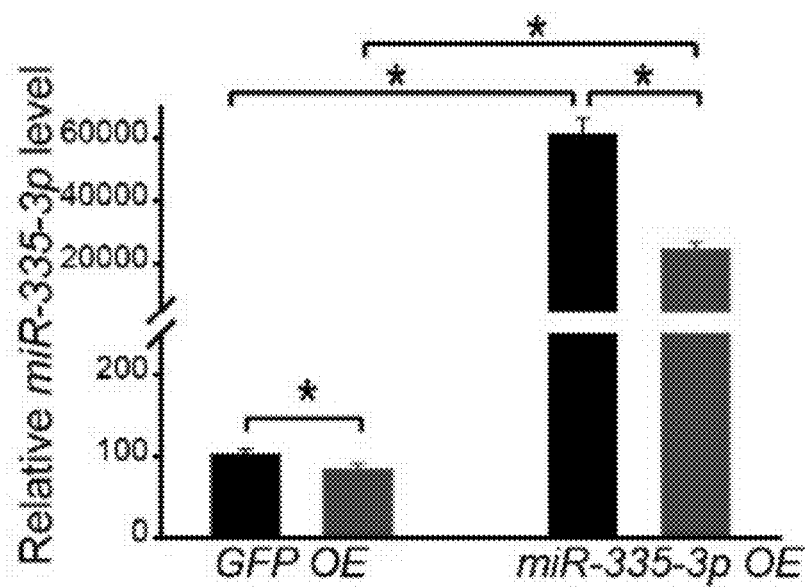
Figure 8F:
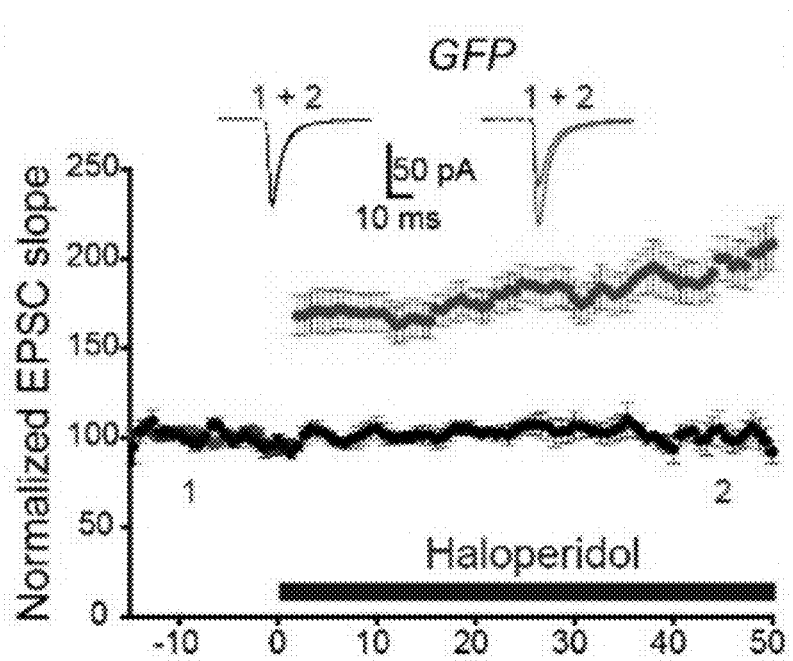
Figure 8G:
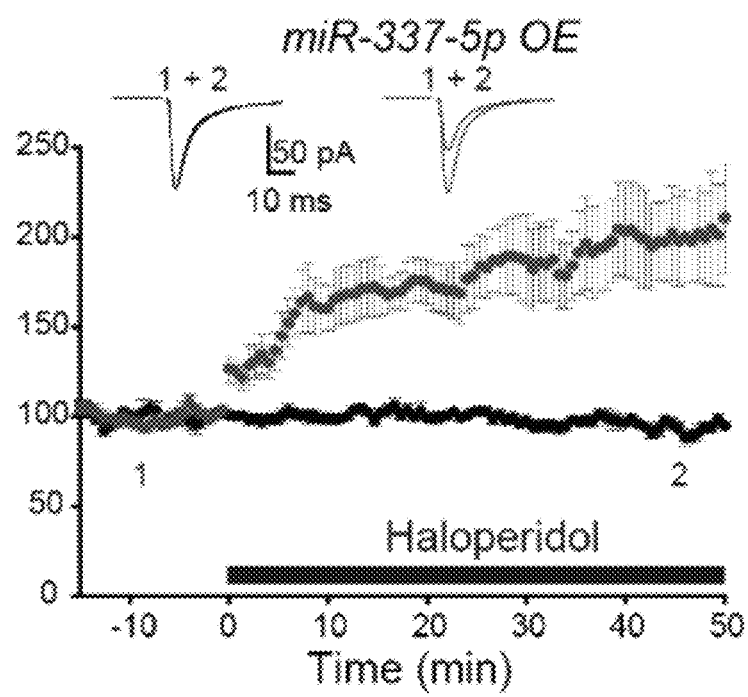
Figure 8H:
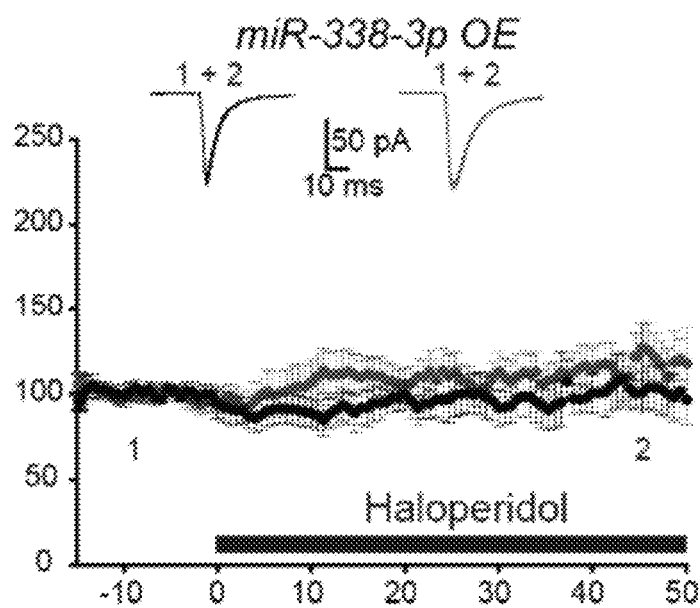
Figure 8I:
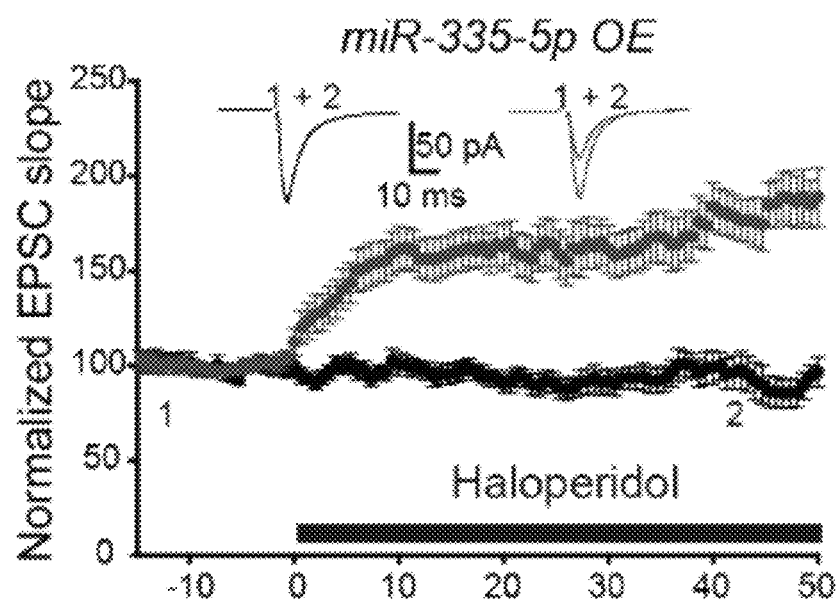
Figure 8J:
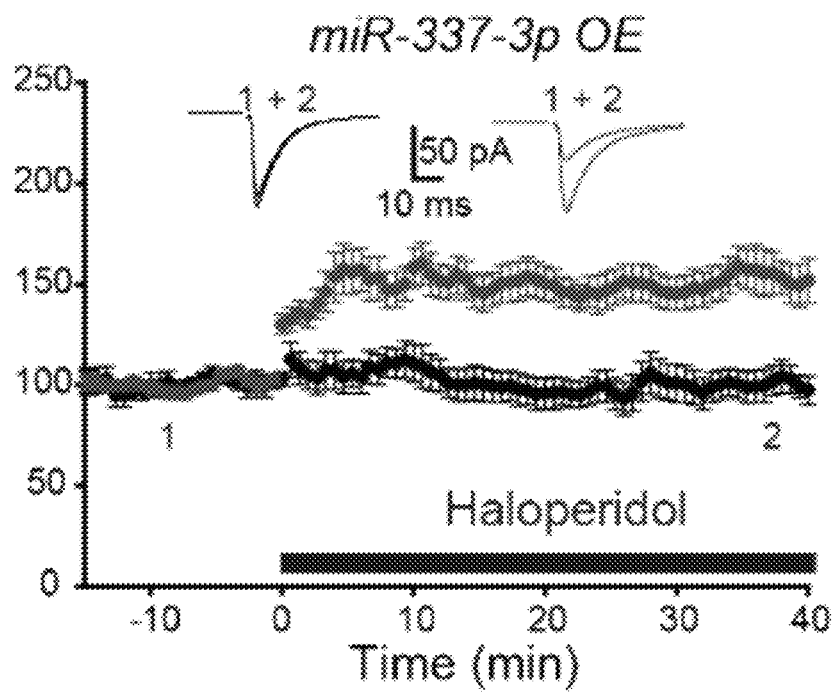
Figure 8K:
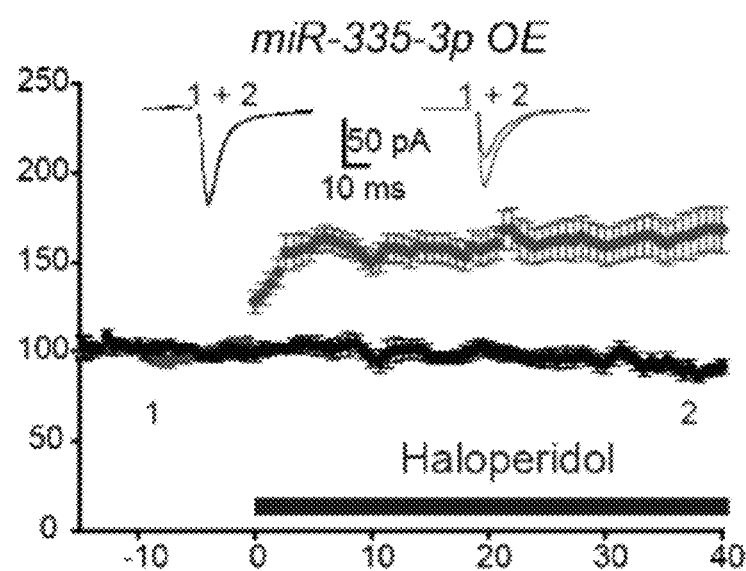

Example 3: miR-338-3p Mediates the Disruption of TC Synaptic Transmission in 22q11DS Because Dgcr8 is involved in miRNA processing[71], the inventors sought to identify the miRNA(s) mediating the Dgcr8-Drd2 mechanism of TC deficiency. To this end, miRNA microarray analysis of the auditory thalamus of 2- and 4-month-old mice was performed (See Table 1, below). Among miRNAs that potentially target the Drd2 transcript (based on miRWalk and Exiqon miRNA target-prediction algorithms providing predicted seed-site sequences) in Drd2 3' UTR, only only five miRNAs (miR-337-3p, miR-337-5p, miR-335-5p, miR-335-3p, and miR-338-3p) were depleted in the auditory thalamus of Df(16)1/+ mice or Dgcr8$^{+/-}$ mice (FIG. 2a-2d). Because miR-185, which is not a Drd2-targeting miRNA, is encoded within the Df(16)1 microdeletion, its substantial depletion in Df(16)1/+ mice served as a positive control (FIG. 2a, 2b). QRT-PCR analysis verified that all five identified Drd2-targeting miRNAs were depleted in Dgcr8$^{+/-}$ mice (second lighter gray and fourth/last darker gray bars of each miRNA) compared to that in WT littermates (first lightest gray and third black bars of each miRNA) at both ages (FIG. 7). Interestingly, the expression of miRNAs decreased with age, regardless of genotype. The levels of identified miRNAs in older mice were lower than those in young WT or Dgcr8$^{+/-}$ mice. However, because Dgcr8 haploinsufficiency depleted these miRNAs at both ages, the age-dependent decline in miRNA expression was exacerbated in mutants and reached minimal values at 4 months in Dgcr8$^{+/-}$ mice (fourth/last darker gray bar of each miRNA) (FIG. 7). This age-dependent decline was exacerbated in Dgcr8$^{+/-}$ mutants and reached the minimal values in 4-month-old Dgcr8$^{+/-}$ mice.

Figure 2E:
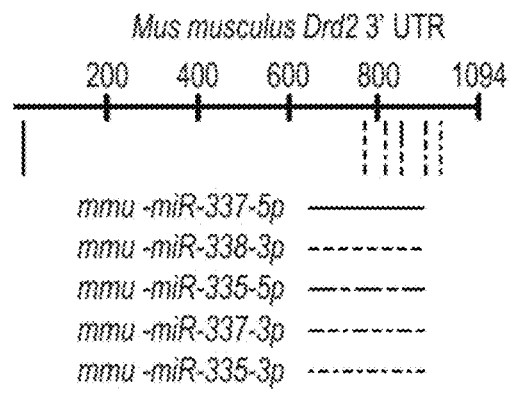
Figure 2F:
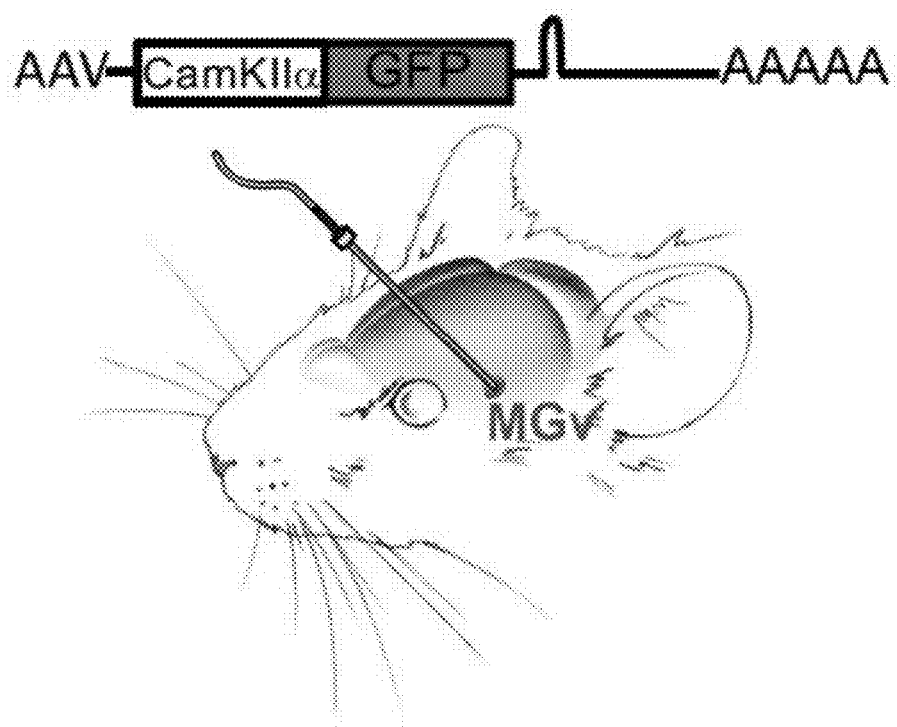
Figure 2G:
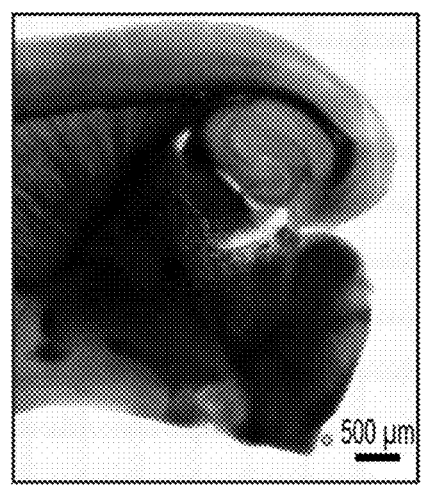
Figure 2H:
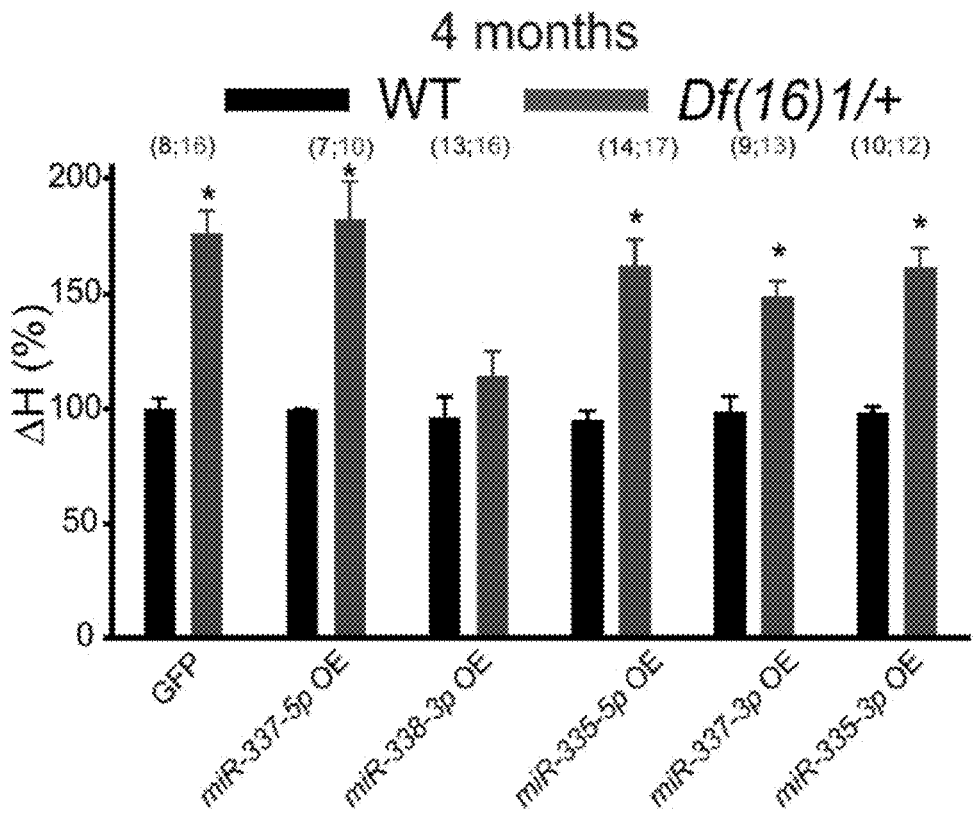

To identify which miRNA(s) targeting the Drd2 3'UTR (FIG. 2e) regulates the Dgcr8-Drd2 mechanism of TC deficiency, a screen was performed based on the abnormal sensitivity of TC projections to haloperidol. To this end, miRNAs were overexpressed in excitatory thalamic neurons by injecting adeno-associated viruses (AAVs) encoding miR-337-5p, miR-338-3p, miR-335-5p, miR-337-3p, or miR-335-3p under control of excitatory neuron-specific promoter CamKII☐ into the MGv of 4-month-old Df(16)1/+ and WT mice (FIG. 2f,2g). Overexpression of individual miRNAs in Df(16)1/+(right gray bars) mice not only replenished the depleted miRNA levels but elevated them beyond those in WT mice (left black bars) (FIG. 8a-8e). However, of the five miRNAs, only miR-338-3p overexpression rescued the abnormal haloperidol sensitivity in Df(16)1/+ mice (FIGS. 2h (right gray bars compared to WT shown in left black bars), 8f-8k (gray lines compared to WT shown in black lines)). Overexpression of miR-338-3p in the MGv of Df(16)1/+ mice decreased Drd2 mRNA levels in the MGv by 47.6%±10.2% compared to the control virus (n=6 mice for AAV-GFP-miR-338-3p and 6 mice for AAV-GFP; p<0.01), confirming that miR-338-3p regulates Drd2 levels. These data suggested that miR-338-3p is the culprit miRNA, and its depletion results in the TC synaptic abnormalities in 22q11DS mice.

Figure 2I:
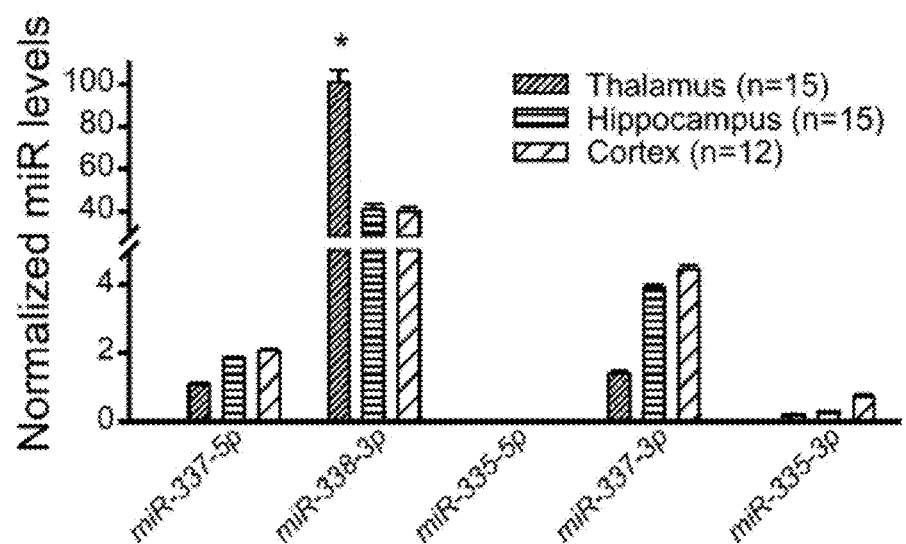
Figure 2J:
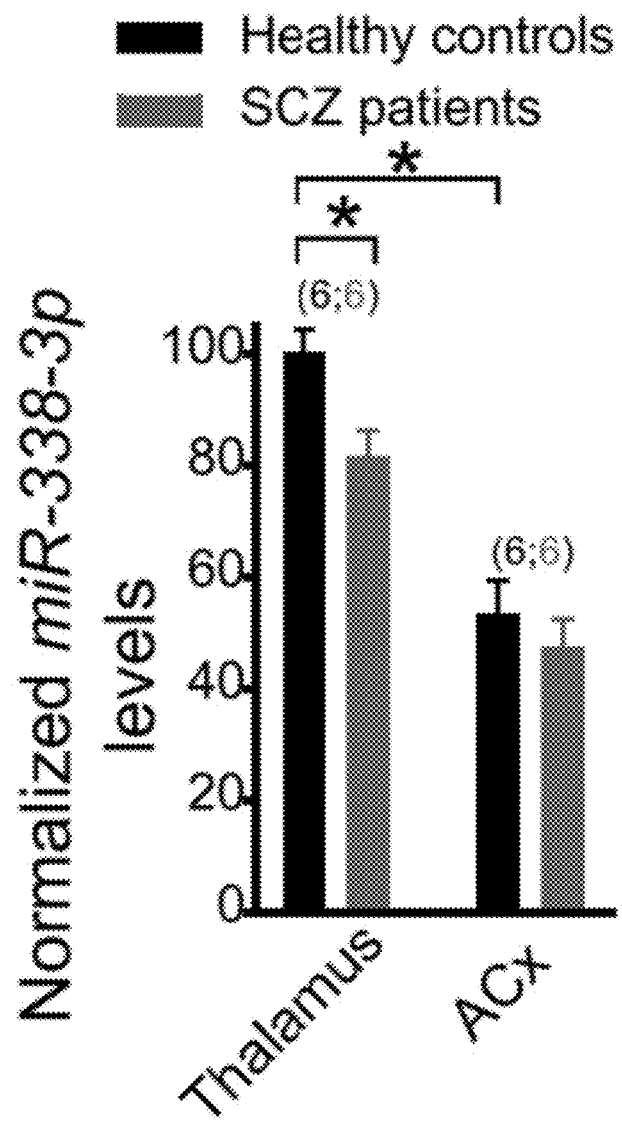
Figure 3A:
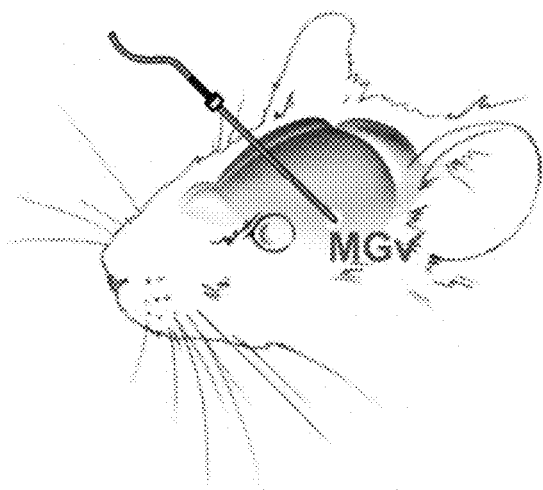
FIG. 3a-3d. Replenishment of miR-338-3p in the auditory thalamus rescues deficits in synaptic transmission and presynaptic neurotransmitter release at TC projections of 22q11DS mouse models. (a) In vivo infection of MGv relay neurons with AAV-GFP-miR-338-3p or AAV-GFP. (b) GFP expression (gray) in cell bodies in the MGv (left) and in projections to the thalamorecipient L3/4 layer of the ACx (right). A patch pipette and part of an L3/4 pyramidal neuron filled with Alexa 594 are shown in gray. (c, d) Input-output relations between stimulation intensity and EPSCs (c) and PPR (d) at TC projections in the ACx of 4- to 5-month-old WT and Df(16)1/+ mice injected with either AAV-GFP-miR-338-3p or AAV-GFP. WT-GFP=black; WT-miR-338-3p=darkest gray in panel c and lightest gray in panel d; Df(16)1/+-GFP=medium gray; Df(16)1/+- miR-338-3p=gray. Insets show representative EPSCs. Scale bar, 20 ms, 50 pA. Numbers of neurons are shown in parentheses, with the number of WT neurons first. Data are represented as the mean±SEM. *p<0.001.
Figure 3B:
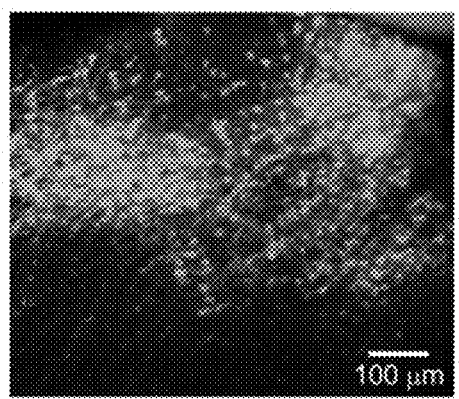
Figure 3B:
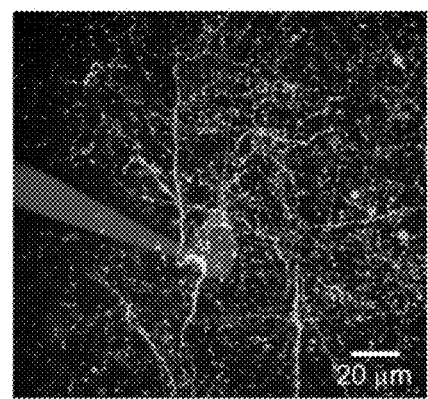
Figure 3C:
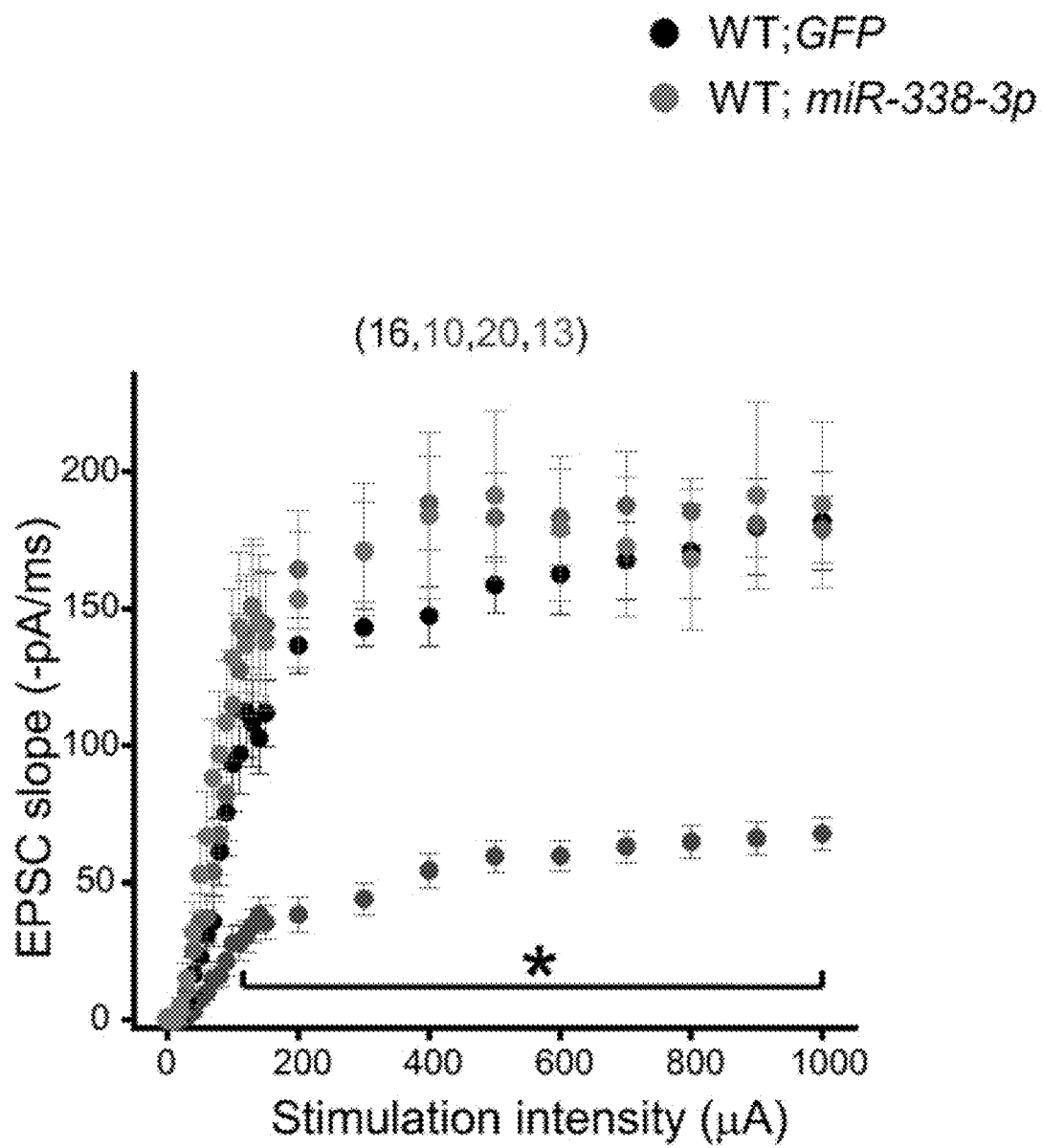
Figure 3D:
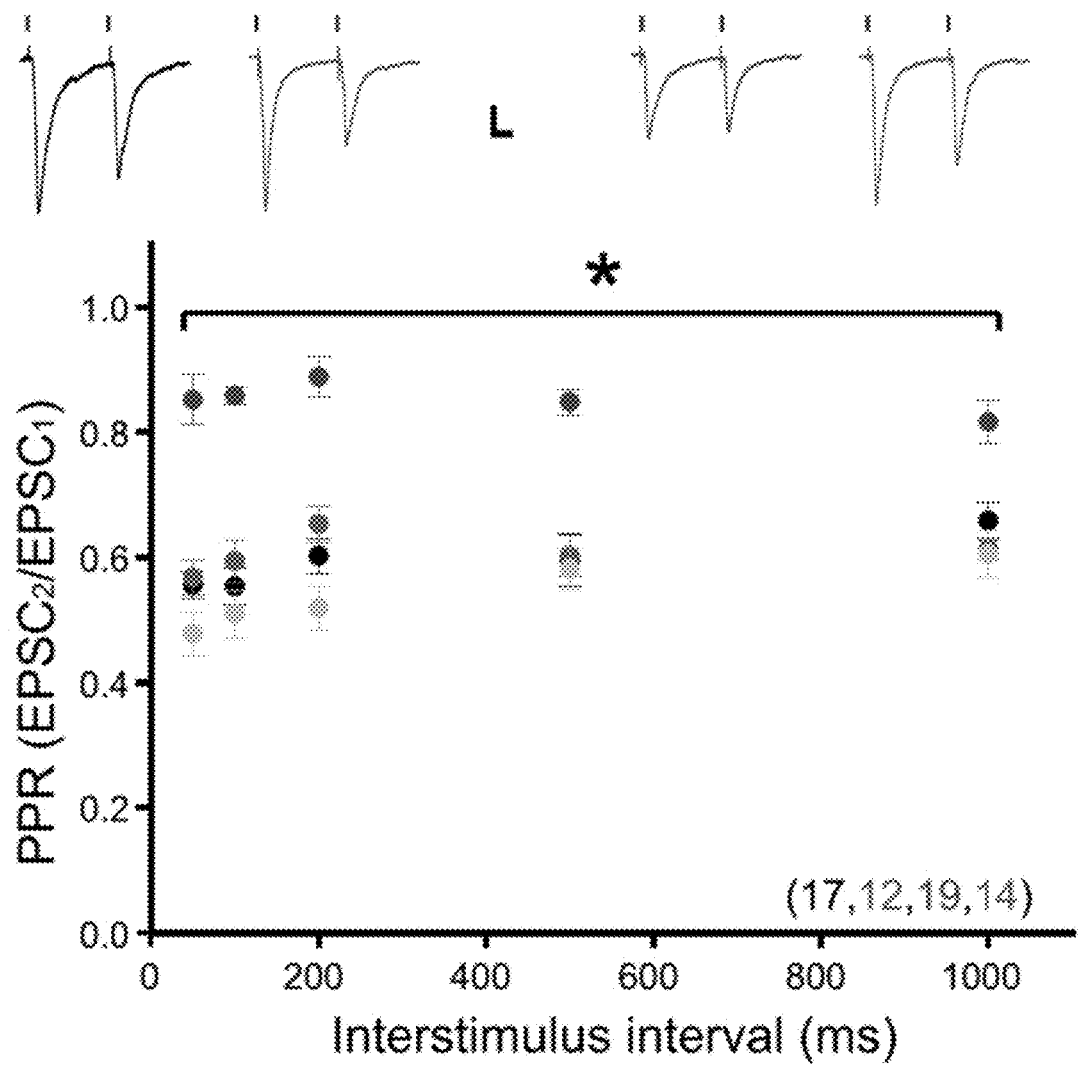
Figure 10A:
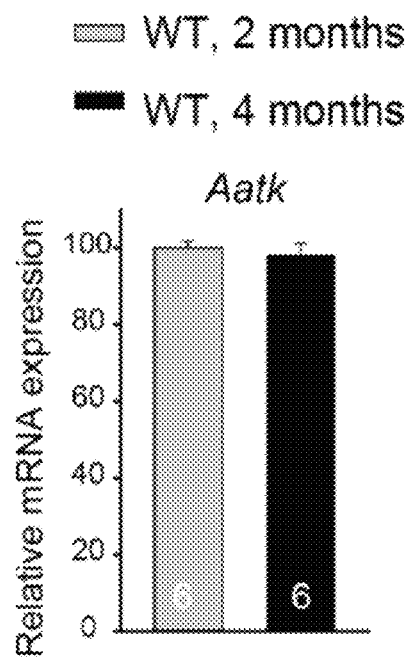
FIG. 10a-10e. The miR-338-targeted deletion in mice does not affect the expression of the miR-338 host gene Aatk or mouse development. (a, b) Normalized average levels of Aatk mRNA in the MGv of 2- (light gray bar) and 4-month-old (black bar) WT mice (a) and in 4-month-old WT (left black bar), miR-338$^{+/-}$ (middle dark gray bar), and miR-338$^{-/-}$ (right light gray bar) littermates (b). Numbers of mice are shown inside the columns. (c) Relative levels of miR-338-3p, miR-338-5p, miR-3065-3p, and miR-3065-5p in the MGv of WT (left black bar), miR-338$^{+/-}$ (middle dark gray bar), and miR-338$^{-/-}$ (right light gray bar) littermates (3-4 mice/genotype). (d, e) Representative image (d) and average body weight (e) of WT (left black bar), miR-338$^{+/-}$ (middle dark gray bar), and miR-338$^{-/-}$ (right light gray bar) male littermates (1.5-3 months of age). Numbers of mice are shown inside the columns. *p<0.05.
Figure 10B:
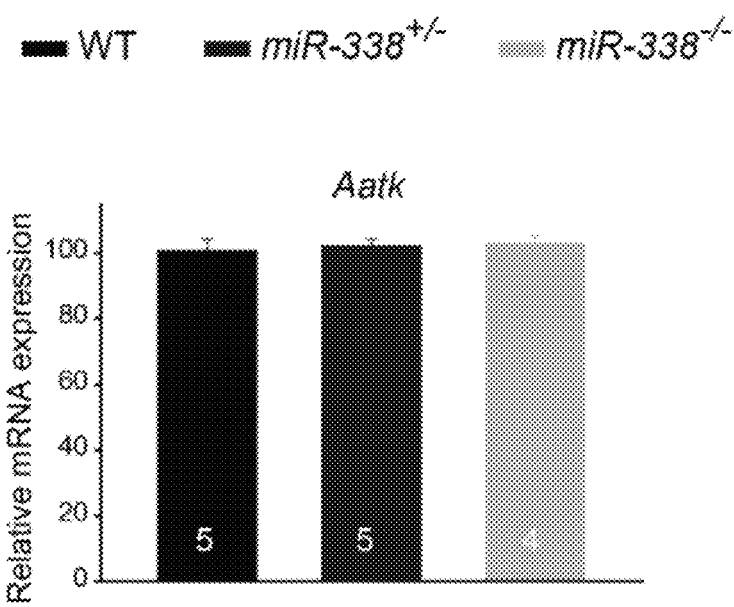
Figure 10C:
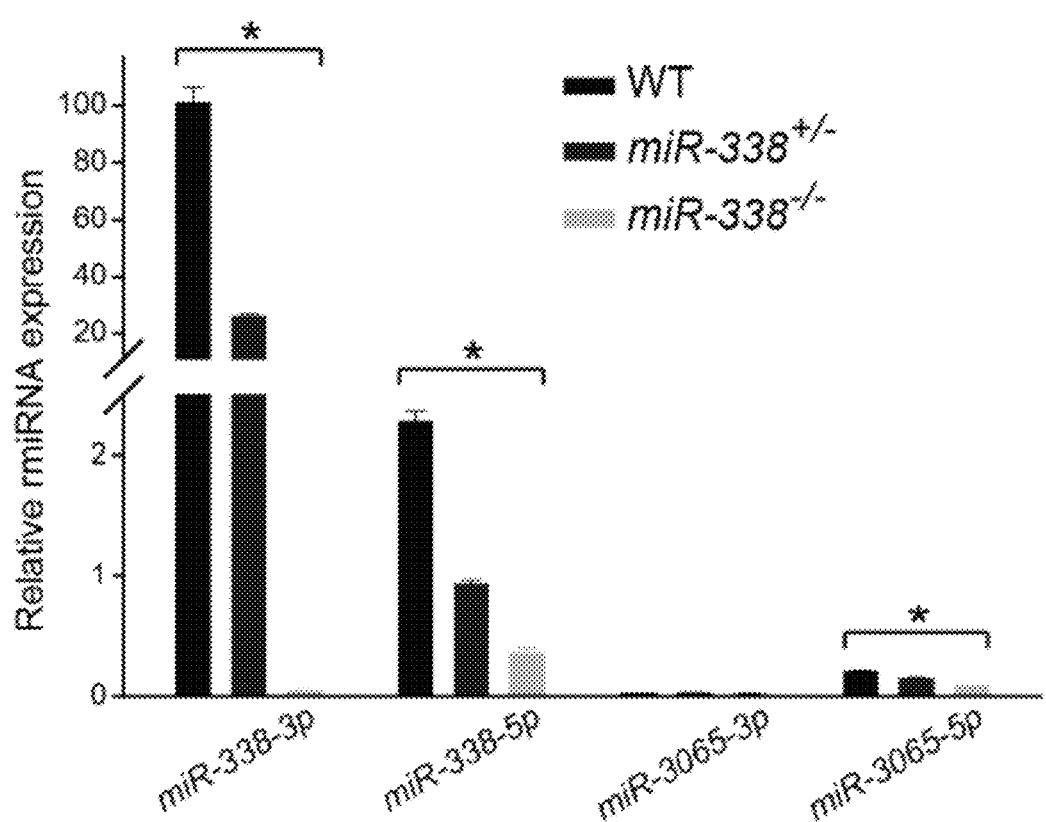

The following data further suggested that miR-338-3p is the culprit miRNA: miR-338-3p overexpression in the MGv substantially decreased Drd2 levels in the MGv (FIG. 10a-10c; left black bars represent WT; middle dark gray bars represent miR-338$^{+/-}$; right light gray bars represent miR-338$^{-/-}$ in 10b,10c). The miR-338-3p was among other miRNAs (miR-335-3p and miR-335-5p) that have conserved seed sites in the mouse and human Drd2 3' UTR (miRWalk algorithm)[58]. Consistent with the notion that only more abundant miRNAs effectively regulate the targeting transcript[59], miR-338-3p appeared to be more crucial for Drd2 regulation in the auditory thalamus than did miR-337-5p, miR-335-5p, miR-337-3p, or miR-335-3p. Indeed, miR-338-3p was enriched in the thalamus compared to the other 4 miRNAs, and the levels of miR-337-3p, miR-335-5p, miR-337-3p, or miR-335-3p ranged between approximately 0% and 4% that of miR-338-3p (FIG. 2i). Moreover, miR-338-3p was substantially enriched in the thalamus compared to other tested brain regions (FIG. 2j), suggesting that depletion of this Drd2-regulating miRNA in 22q11DS mainly affects thalamic function. Similarly, miR-338-3p was enriched in the MGv compared to the ACx (Brodmann area 41) in postmortem tissue samples from human subjects (n=6 for both thalamus and ACx, p<0.001) (FIG. 2j). Moreover, miR-338-3p was significantly decreased in the thalamus of schizophrenic patients (right gray bars) compared to that in age- and sex-matched controls (left black bars) (n=6 for both conditions, p<0.05) (FIG. 2j). The inventors previously showed that the Drd2 protein level is elevated in the same set of MGv samples[39].

Figure 4A:
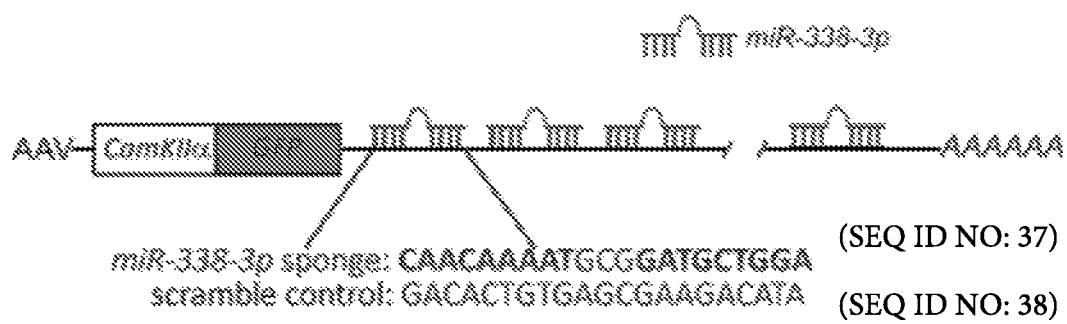
FIG. 4a-4p. The depletion of knockout of miR-338 replicates the TC deficiency of Df(16)1/+ mice. (a) AAV expressing a miR-338-3p sponge construct with multiple binding sites to miR-338-3p in the GFP 3'UTR, under control of the CamKIIα promoter. Sequences for the miR-338-3p sponge and scrambled control are shown below. Bold text indicates seed-site sequence. (b) Relative Drd2 mRNA levels after infection of MGv excitatory neurons in WT mice with an AAV encoding a scrambled control (left black bar) or miR-338-3p sponge (right gray bar). (c) Normalized mean TC EPSCs before and after application of haloperidol in WT mice after infection of MGv neurons with AAVs encoding a scrambled control (black) or miR-338-3p sponge (light gray). Insets show representative EPSCs. (d) Generation of miR-338 KO mice. (e) Normalized levels of miR-338-3p and Drd2 in the auditory thalamus of WT (left black bar), miR-338$^{+/-}$ (middle dark gray bar), and miR-338$^{-/-}$ (right light gray bar) mice. (f) Simultaneous recordings of EPSCs in L3/4 pyramidal neurons evoked by electrical stimulation of the thalamocortical (TC) and corticocortical (CC) projections. (g, h) Input-output relations between electrical stimulation intensity and EPSCs at TC projections (g) and CC projections (h) in the ACx of 4-month-old WT (black) and miR-338$^{+/-}$ (white) mice. (i-l) PPR (i, j) and NMDAR/AMPAR ratio (k, l) of electrically evoked EPSCs measured at TC (i, k) and CC projections (j, 1) of 4-month-old WT (black) and miR-338$^{+/-}$ (gray or white) mice. WT mice (n=26) are represented by the bottom black line and miR-338$^{+/-}$ mice (n=22) are represented by the upper gray line in i. WT mice are represented by the left black bar and miR-338$^{+/-}$ mice are represented by the right gray bar in k, l, with numbers of neurons indicated in the bars. (m) Optogenetic experiments in TC slices. ChR2 was expressed in the MGv, under control of the CamKIIα promoter. (n-p) Input-output relations (n), PPR (o), and NMDAR/AMPAR ratio (p) of optically evoked EPSCs (oEPSC) measured at TC projections of 4-month-old WT (black) and miR-338$^{+/-}$ (white) mice. WT mice are represented by the left black bar and miR-338$^{+/-}$ mice are represented by the right gray bar in p, with numbers of neurons indicated in the bars. Insets show representative AMPAR-mediated (-70 mV holding membrane potential) and NMDAR-mediated (+40 mV holding membrane potential) EPSC and oEPSC traces. Scale bars (if not noted otherwise), 20 ms, 50 pA. Numbers of neurons are shown inside the columns or parentheses, with the number of WT neurons first. Data are represented as the mean±SEM. *p<0.05.
Figure 4B:
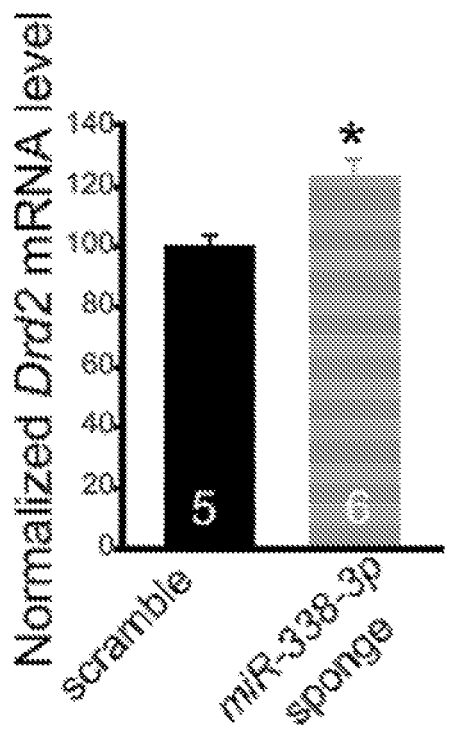
Figure 4C:
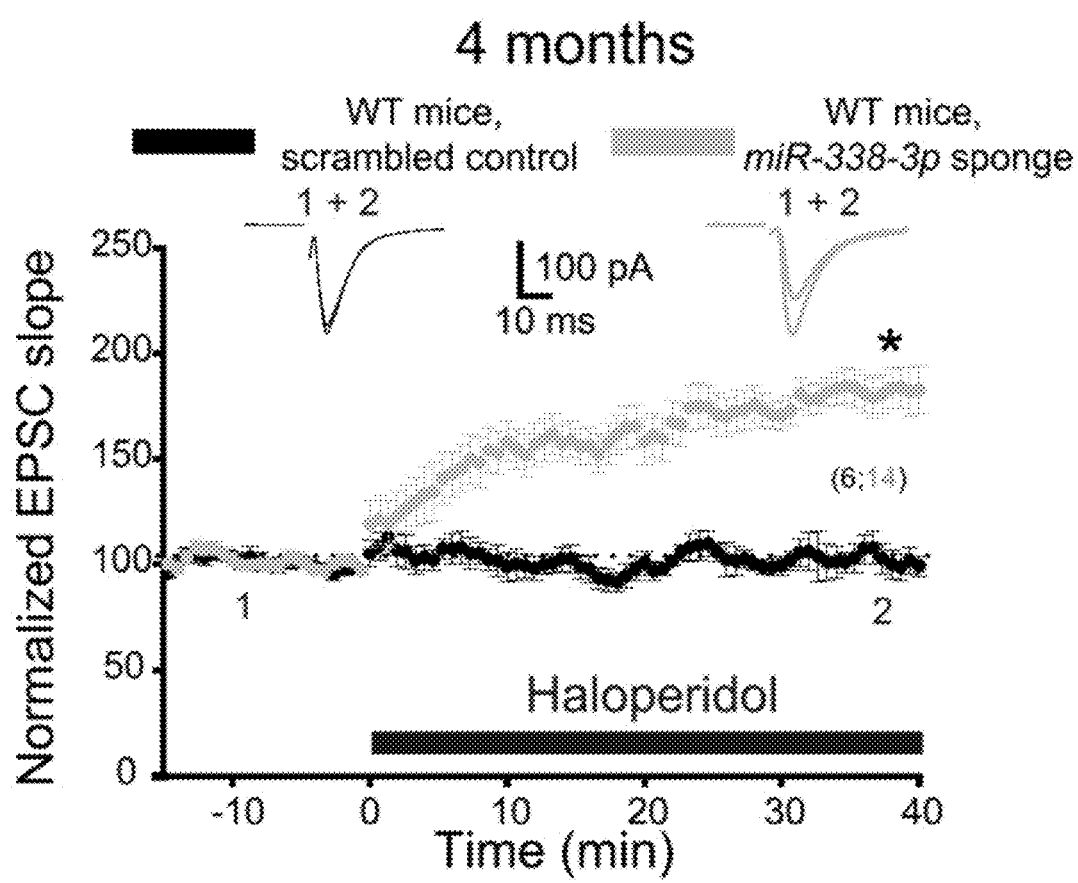
Figure 4D:
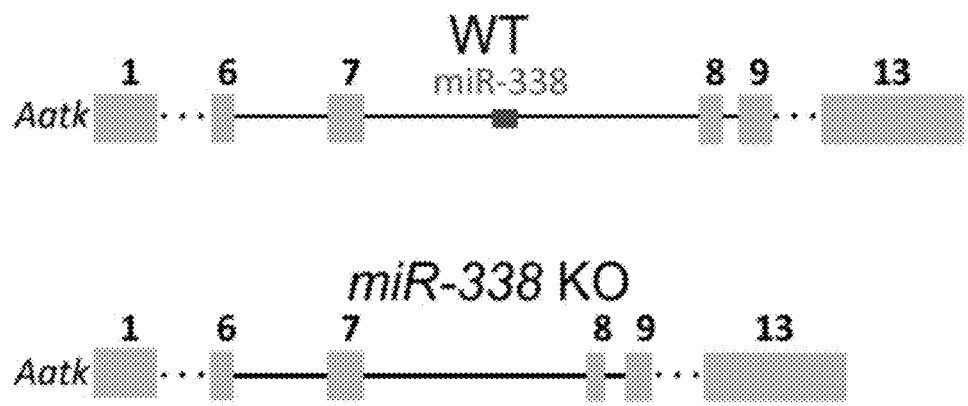
Figure 9:
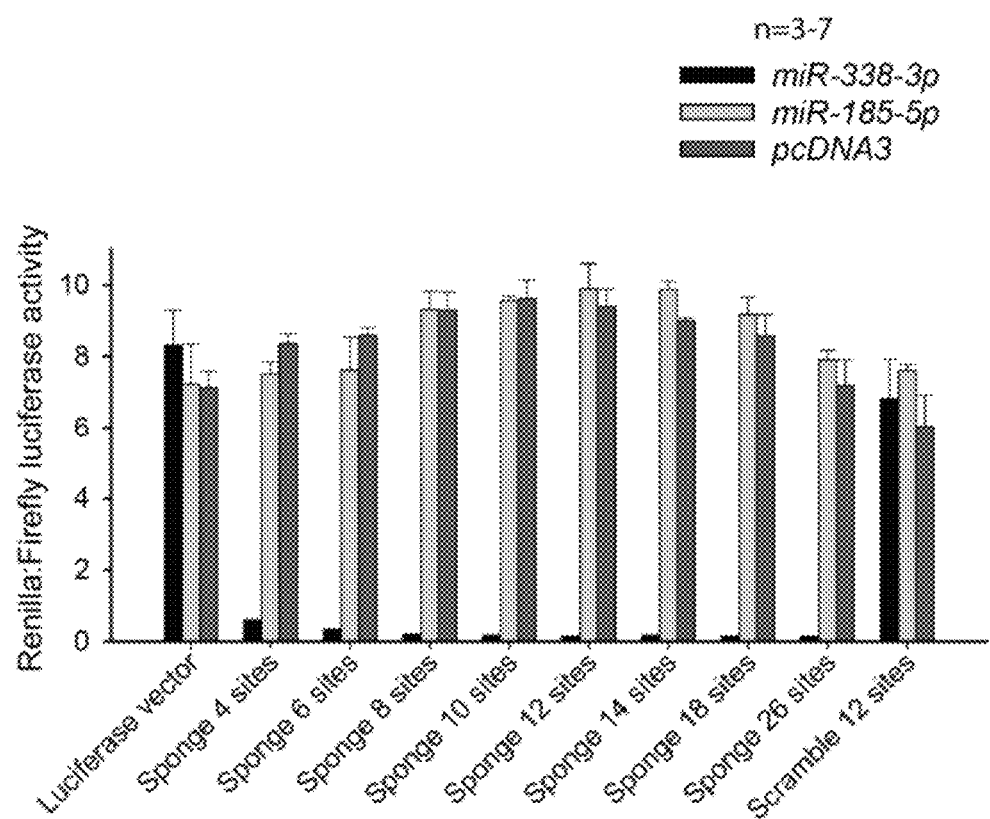
FIG. 9. Validation of the miR-338-3p sponge. Luminescence activity measured with the luciferase reporter vector alone, cloned into the luciferase reporter vector miRNA sponges containing 4 to 26 seed sites, or scrambled sites in the presence of control pcDNA (right dark gray bar), miR-338-3p (left black bar), or miR-185-5p (middle light gray bar). Based on these experiments, the miR-338-3p sponge with 12 seed sites was chosen for in vivo experiments.

Example 4: miR-338-3p Depletion is Sufficient to Trigger Sensitivity of TC Projections to Antipsychotics; miR-338 Depletion in the MGv or miR-338-Knockout Recapitulates the Auditory TC Synaptic Abnormalities of 22q11DS Mice To test whether miR-338-3p depletion is sufficient to trigger sensitivity of TC projections to antipsychotics, two strategies were employed: (i) a miR-338-3p sponge[26] was constructed by using a previously described strategy[78]; and (ii) generation of miR-338-knockout (KO) mice (FIG. 4d). The miR-338-3p sponge efficiency was verified in an in vitro system by using the luciferase assay. The sponge with 12 seed sites was sufficient to almost completely and specifically deplete miR-338-3p levels according to this assay (FIG. 9). On the basis of these data, AAVs were constructed expressing either the miR-338-3p sponge or a scrambled control vector under the control of the CamKIIα promoter (FIG. 4a). The AAV expressing the miR-338-3p sponge that was injected into the MGv of WT mice was sufficient to increase Drd2 mRNA (FIG. 4b) and render the TC projections sensitive to haloperidol (FIG. 4c). The excitatory neurons in the MGv of WT mice were infected with AAVs expressing either the miR-338-3p sponge or a scrambled control vector under the control of the CamKII☐ promoter (FIG. 4a). The miR-338-3p sponge (right gray bar) increased Drd2 mRNA in the auditory thalamus relative to scrambled control (left black bar) (FIG. 4b). The miR-338-3p sponge (gray) also rendered TC projections in WT mice abnormally sensitive to haloperidol, whereas the scrambled control (black) did not (FIG. 4c). These experiments indicate that depletion of miR-338-3p is necessary and sufficient to increase Drd2 expression in the thalamic-relay neurons and render TC projections to the ACx sensitive to antipsychotics.

Figure 4E:
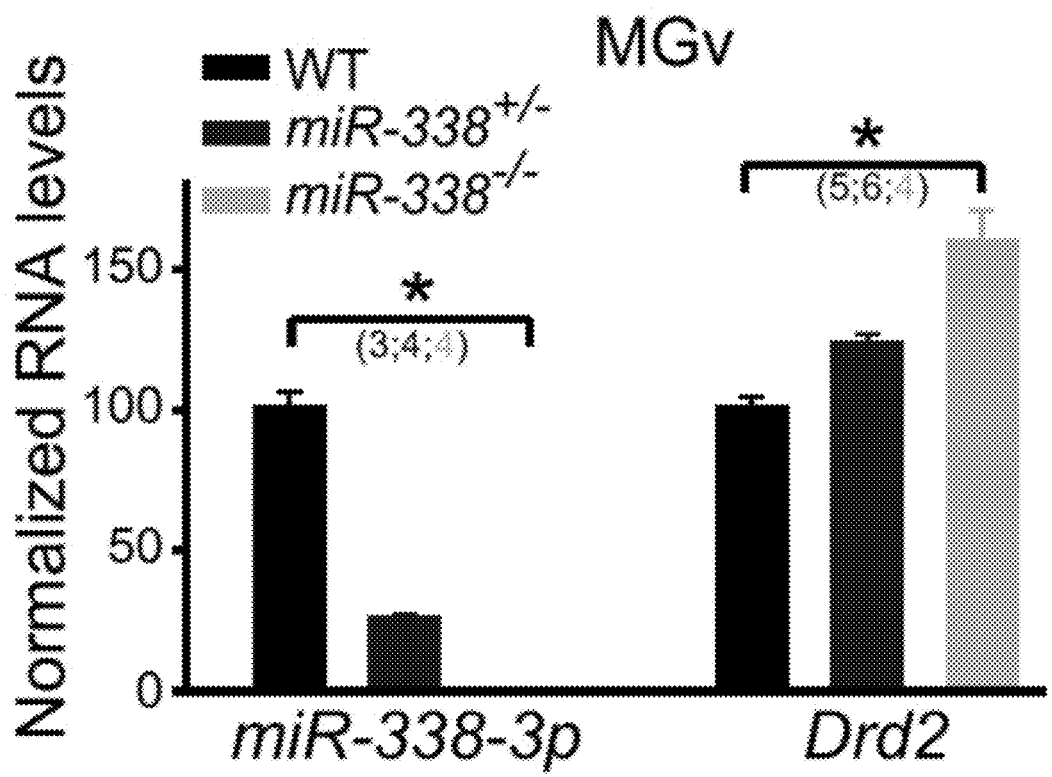
Figure 10D:
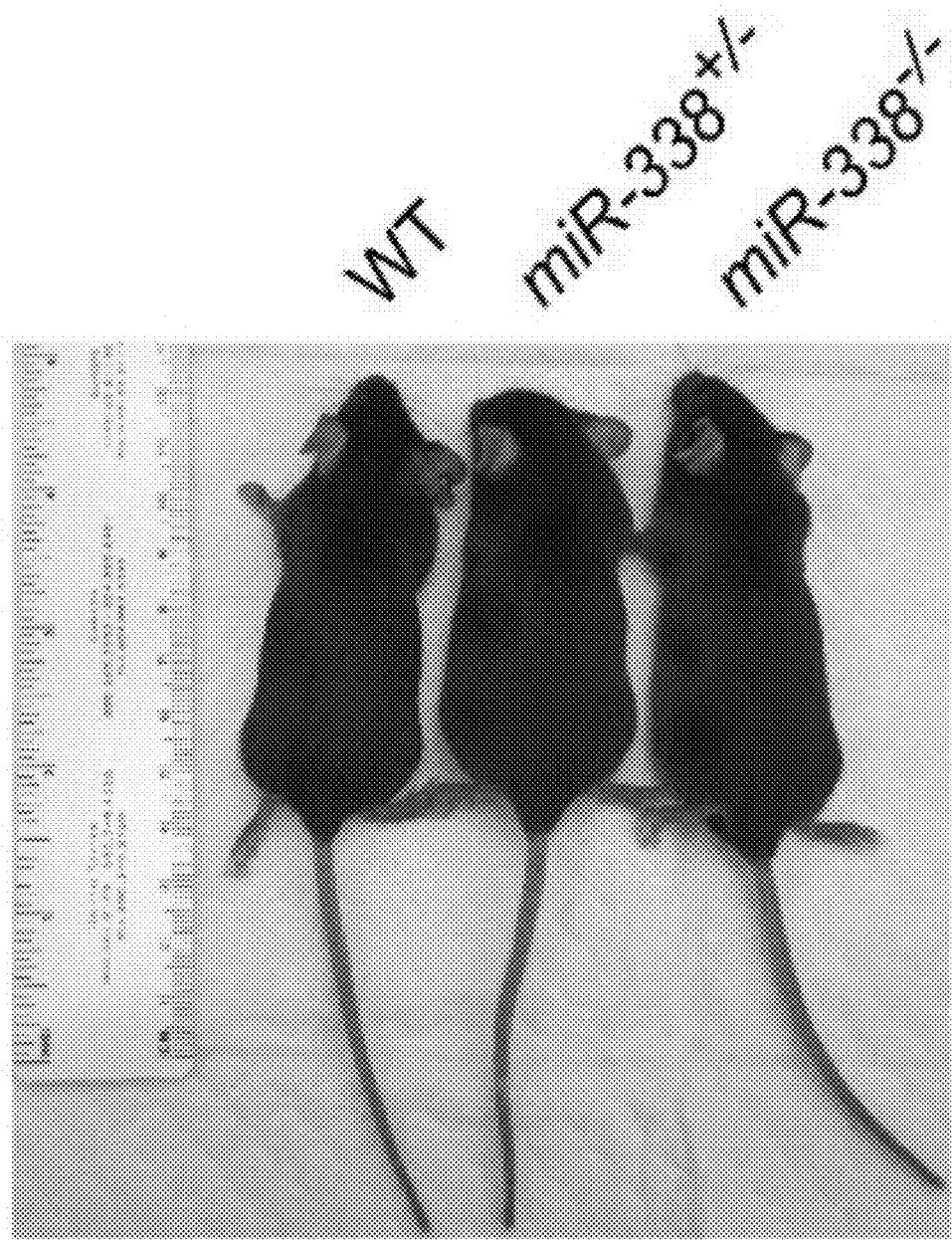
Figure 10E:
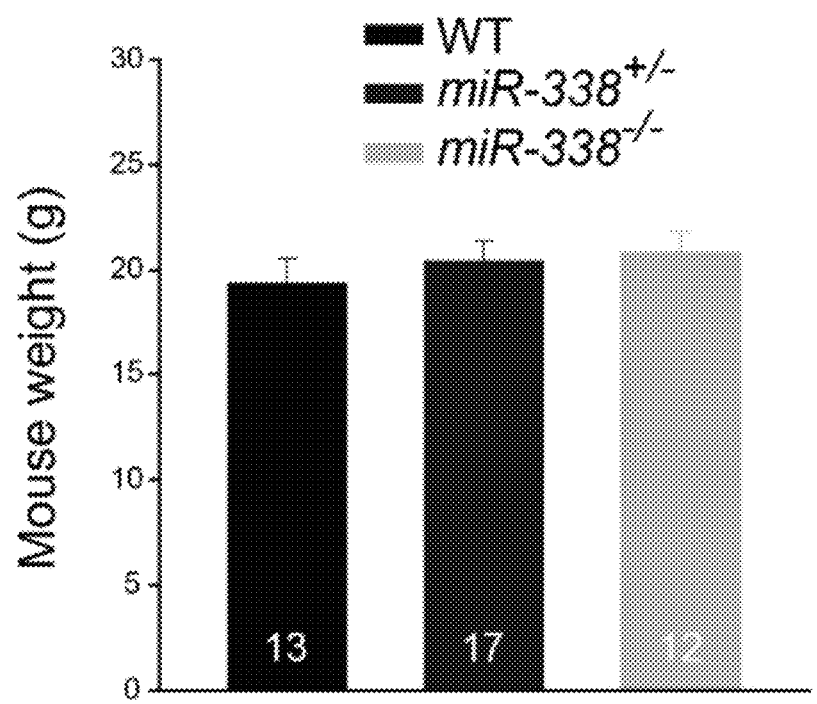

Because miR-338-3p appears to be a major miRNA controlling Drd2 expression in the auditory thalamus, a mutant mouse lacking miR-338 (miR-338 KO mice) was generated (FIG. 4d). The miR-338 is an intragenic miRNA whose genomic locus is inside the seventh intron of the Aatk (apoptosis-associated tyrosine kinase) gene. However, unlike miR-338-3p, Aatk expression in the MGv was not affected by age (FIG. 10a) or miR-338 deletion (FIG. 10b; left black bar corresponding to WT mice, middle dark gray bar corresponding to miR-338$^{+/-}$ mice; right light gray bar corresponding to miR-338$^{-/-}$ mice). The miR-338 KO mice lacked miR-338-3p, miR-338-5p, and miR-3065 (both –3p and –5p species) (FIG. 10c), whose genomic locus overlaps with miR-338. However miR-338-5p, miR-3065-3p, and miR-3065-5p were not Drd2-targeting miRNAs, as predicted by the microRNA target-prediction algorithms, and their expression level in the auditory thalamus were 0% and 2.5% that of miR-338-3p (FIG. 10c; left black bar corresponding to WT mice, middle dark gray bar corresponding to miR-338$^{+/-}$ mice; right light gray bar corresponding to miR-338$^{-/-}$ mice). The miR-338$^{+/-}$ or miR-338 mice developed normally without any gross morphological abnormalities (FIG. 10d,10e; left black bar corresponding to WT mice, middle dark gray bar corresponding to miR-338$^{+/-}$ mice; right light gray bar corresponding to miR-338$^{-/-}$ mice in 10e). Their Drd2 levels were inversely correlated with miR-338-3p levels in the auditory thalamus (FIG. 4e; left black bar corresponding to WT mice, middle dark gray bar corresponding to miR-338$^{+/-}$ mice; right light gray bar corresponding to miR-338$^{-/-}$ mice), further indicating that miR-338-3p is the critical regulator of Drd2 expression in the auditory thalamus.

Figure 4I:
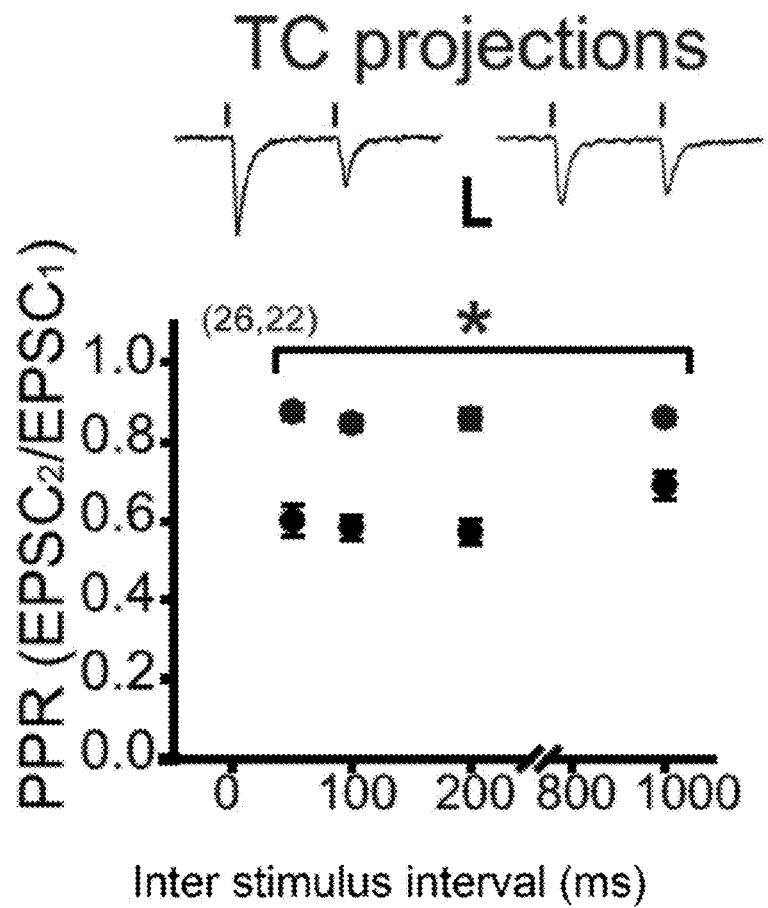
Figure 4J:
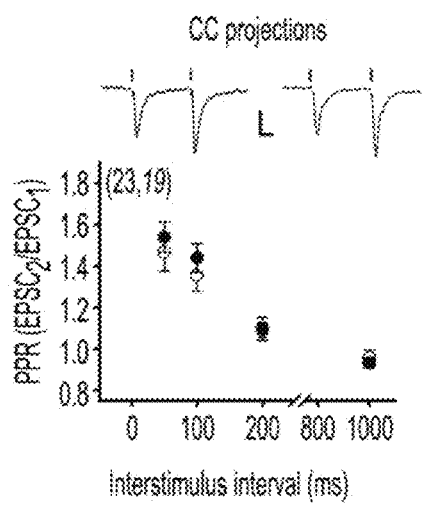
Figure 4K:
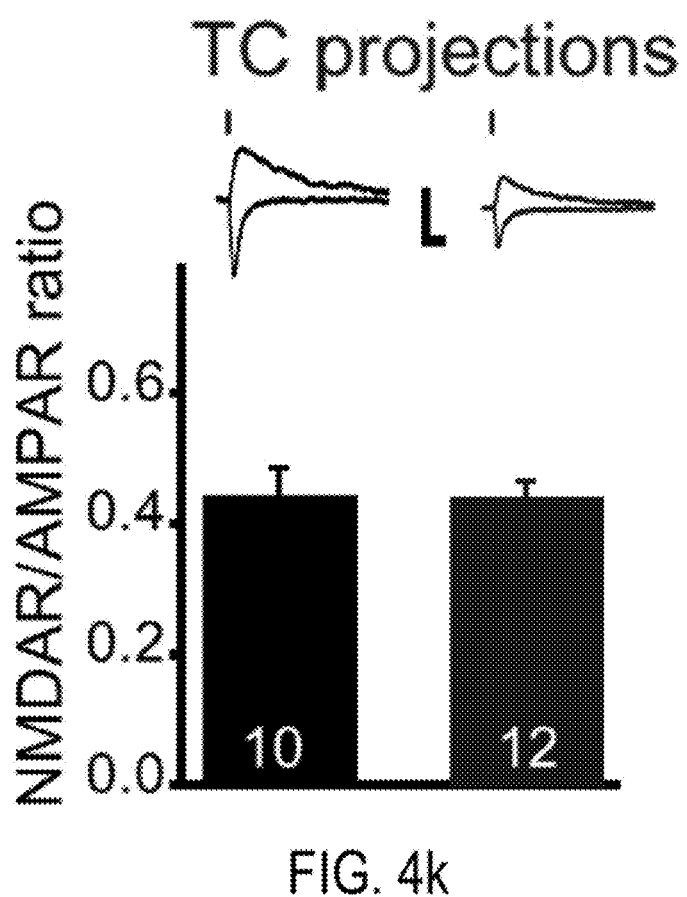
Figure 4L:
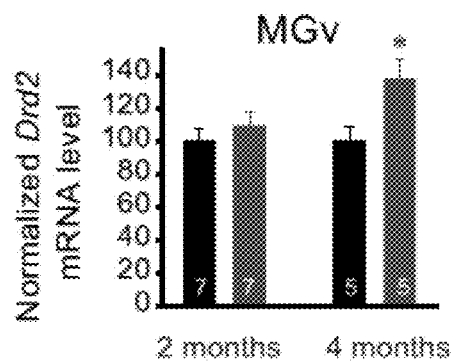
Figure 4M:
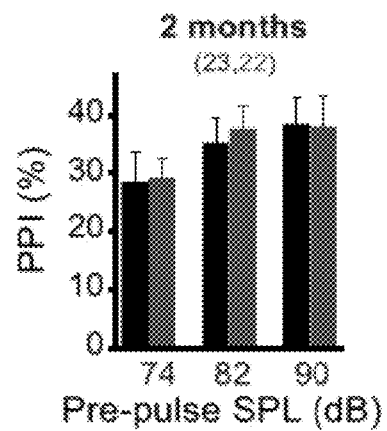
Figure 4N:
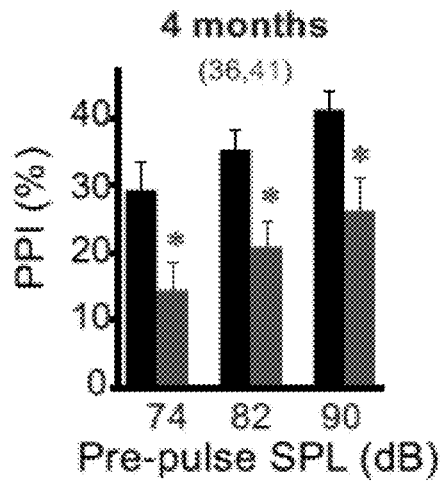
Figure 4O:
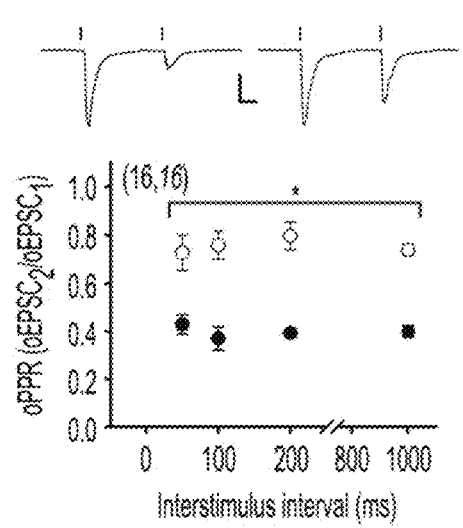
Figure 4P:
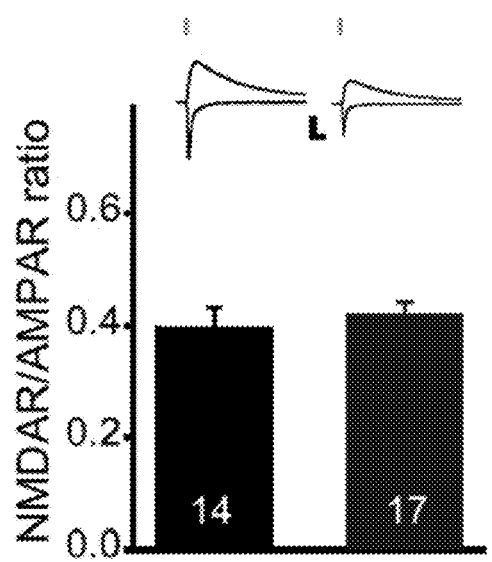

Because miR-338-3p is depleted but not eliminated in Df(16)1/+ mice, TC synaptic properties were tested in 4-month-old miR-338$^{+/-}$ mice. Like that in Df(16)1/+ mice[5], synaptic transmission at TC projections was substantially disrupted in miR-338$^{+/-}$ mice. The input-output function, which were tested by electrical stimulation of TC projections, showed a significant (p<0.01) decrease in TC EPSCs in miR-338$^{+/-}$ mice (gray or white circles) compared to that in WT mice (black circles) (FIG. 4f,4g). This disruption was specific to TC projections. The input-output function tested by electrical stimulation of corticocortical (CC) projections in the same slices did not differ between miR-338$^{+/-}$ (white circles) and WT mice (black circles) (FIG. 4h). The PPR of two consecutive electrically evoked EPSCs was substantially altered in TC but not CC projections of miR-338$^{+/-}$ mice (gray or white circles) compared to that in WT (black circles) controls (FIG. 4i,4j). Specifically, FIG. 4i shows an increase in the PPR of two consecutive electrically evoked EPSCs of the miR-338$^{+/-}$ mice (top gray line, n=22) relative to WT mice (bottom black line, n=26). In contrast, the NMDAR/AMPAR ratio (a measure of the postsynaptic function) was normal in both TC and CC projections of miR-338$^{+/-}$ mice (right gray bars compared to WT, shown in left black bars) (FIG. 4k,4l). Because electrical stimulation of the thalamic radiation may affect circuits other than TC projections[79], TC projections were activated more selectively using the optogenetic approach. To that end, AAVs expressing ChR2 under the control of CamKIIα were injected into the MGv of miR-338$^{+/-}$ and WT littermates. TC projections were then activated by using 473-nm light pulses (FIG. 4m). The input-output relations and PPR (but not the NMDAR/AMPAR ratio of optically evoked EPSCs were substantially decreased in 4-month-old miR-338$^{+/-}$ mice (white circles or gray bars) compared to that in WT littermates (black circles or black bars) (FIG. 4n-4p; data from WT mice shown in left black bar and miR-338$^{+/-}$ mice shown in right gray bar in p), which recapitulated the TC disruption in 22q11DS mouse models.

Figure 5A:
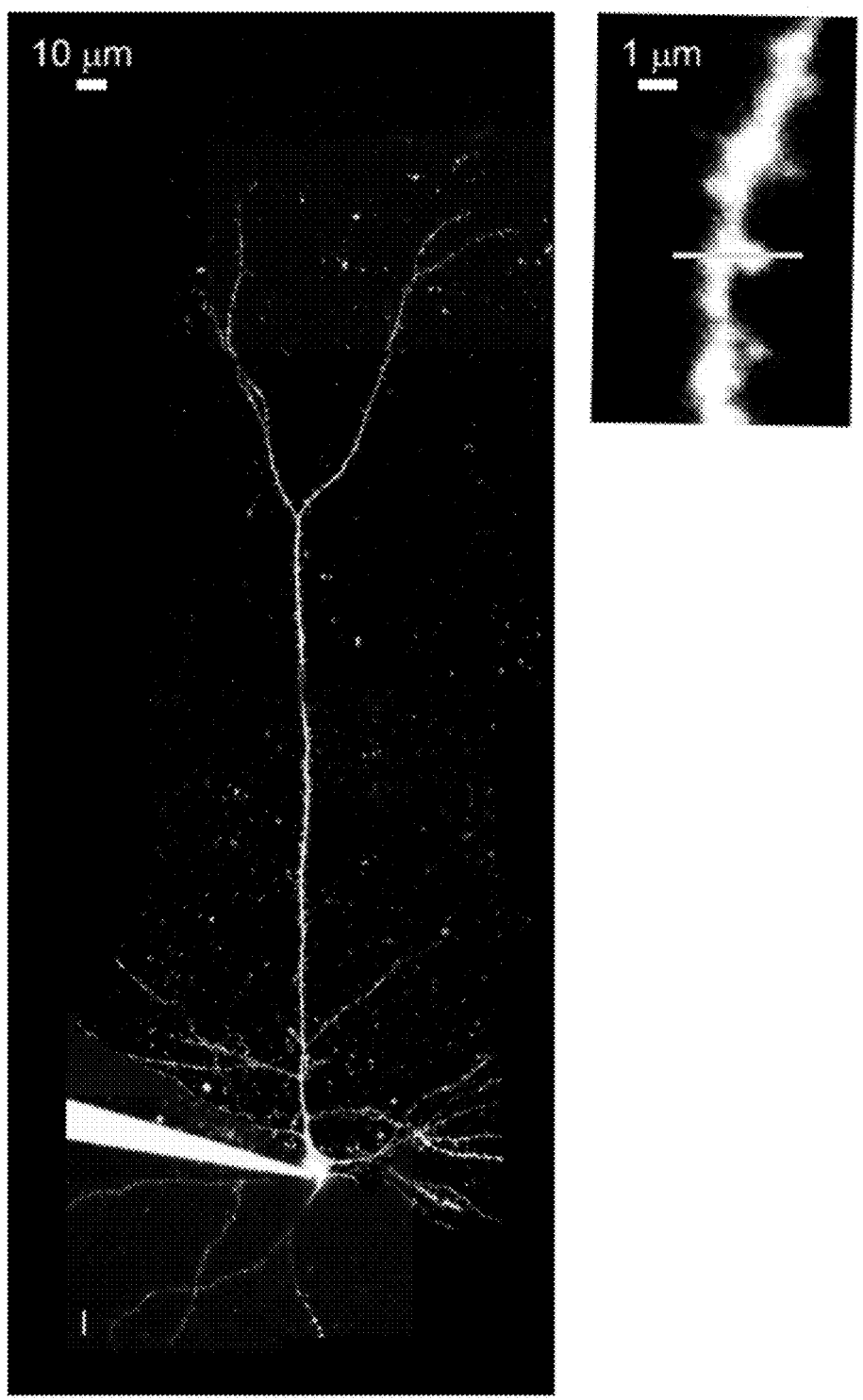
FIG. 5a-5f. Probability of glutamate release is reduced at TC projections of miR-338$^{+/-}$ mice. (a) An L3/4 pyramidal neuron filled with Fluo-5F and Alexa 594 through a patch pipette (left) to visualize synaptically evoked calcium transients inside dendritic spines (right). Gray line represents the line scan. (b) Calcium transients in a dendritic spine in response to a single thalamic stimulation (arrows) repeated 10 times at 0.1 Hz. (c) Location of active TC inputs on dendritic trees of L3/4 pyramidal neurons spines. (0;0), soma coordinates (apical dendrites pointing upwards); black circles represent data from WT mice while white circles represent data from miR-338$^{+/-}$ mice. (d-f) Average distances from soma to active TC inputs (d), calcium transient peak amplitudes (e), and probabilities (f) in response to 10 to 20 single TC stimulations. WT mice are represented by the left black bar and miR-338$^{+/-}$ mice are represented by the right gray bar in d-f. Numbers of spines are shown in parentheses (WT=27 spines, miR-338$^{+/-}$=32 spines). Data are represented as the mean±SEM. *p<0.01.
Figure 5B:
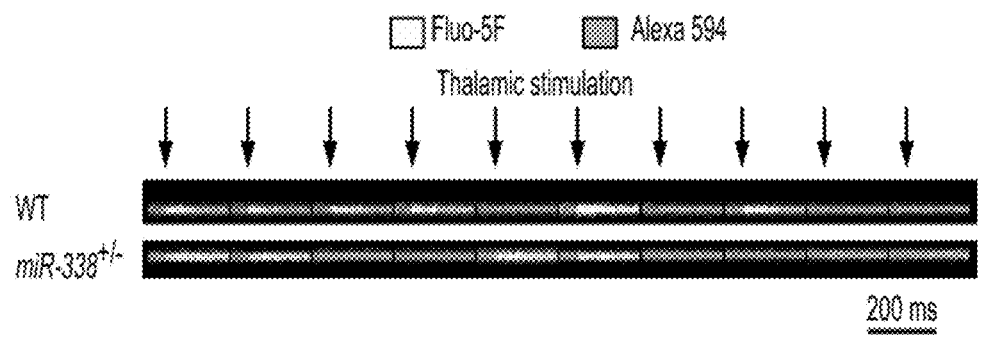
Figure 5C:
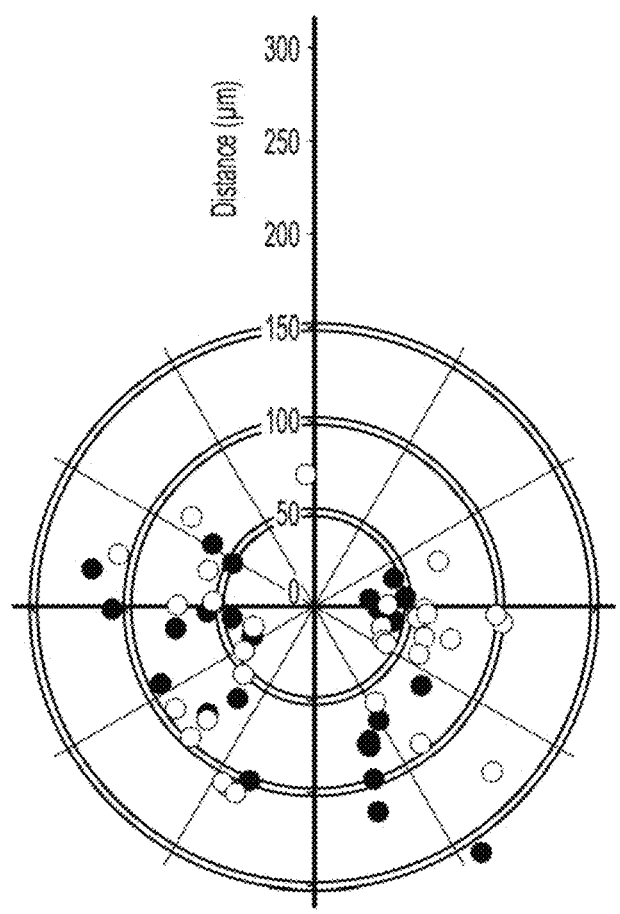
Figure 5D:
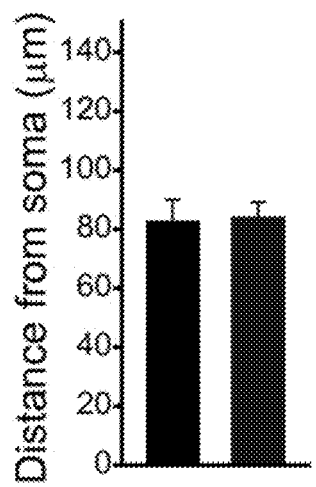
Figure 5E:
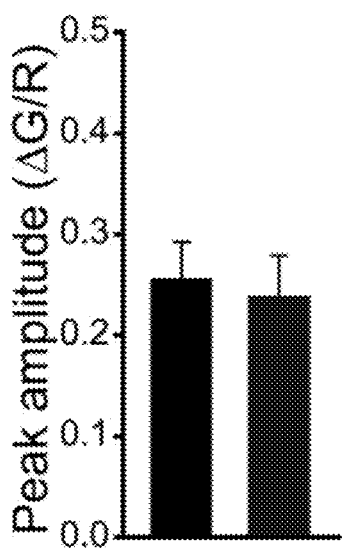
Figure 5F:
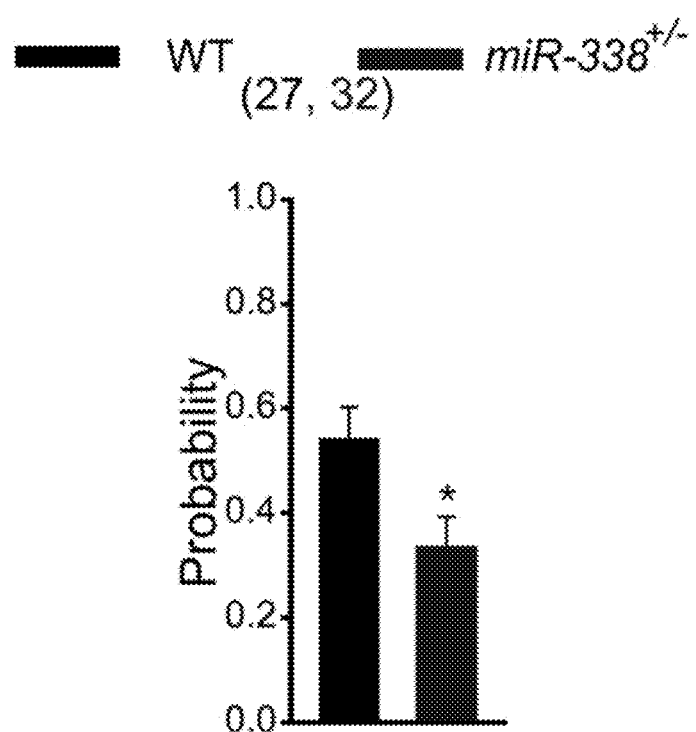

Example 5: miR-338 Haploinsufficiency Disrupts TC Projections by Decreasing the Probability of Glutamate Release from Thalamic Projections The inventors have previously shown that the TC disruption of synaptic plasticity in 22q11DS mouse models was due to defective presynaptic function, which was in turn was caused by reduced probability of glutamate release from thalamic projections[39]. Abnormalities in the input-output relation and PPR at TC projections of miR-338$^{+/-}$ mice also suggested a deficit in presynaptic function at TC glutamatergic synapses. To understand the nature of this deficit, two-photon calcium imaging was performed in dendritic spines, which are the inputs of thalamic projections onto thalamo-recipient neurons in the ACx. L3/4 pyramidal neurons were loaded with the calcium indicator Fluo-5F and cytoplasmic dye Alexa 594 (FIG. 5a) and dendritic spines that responded to electrical stimulation of the thalamic radiation were identified (FIG. 5b). This method enabled measurement of three factors that may contribute to the TC disruption: the distribution of synaptic inputs on dendritic trees of postsynaptic neurons, the amplitudes of calcium transients, and the probability of calcium transients at individual dendritic spines (a proxy for the probability of neurotransmitter release measured at a single synaptic input)[5, 80, 81]. The distribution of active TC inputs on dendritic trees and the peak amplitudes of postsynaptic calcium transients in miR-338$^{+/-}$ mice (gray bars or white circles) were comparable to that in WT mice (black) (FIG. 5c-5e), suggesting that TC development, pathfinding, synaptic targeting of cortical neurons by TC projections, and postsynaptic glutamatergic receptor function were not compromised in miR-338$^{+/-}$ mice. However, the probability of calcium transients in dendritic spines of thalamorecipient neurons in response to a low-frequency (0.1 Hz) train of stimuli was deficient in miR-338$^{+/-}$ mice (FIG. 5f). This result indicates that the depletion of miR-338 decreased the probability of glutamate release at TC projections, which underlies the TC disruption in 22q11DS. Data from 27 WT mice shown in left black bars and data from 32 miR-338$^{+/-}$ mice shown in right gray bars in FIG. 5d-5f.

Figure 6A:
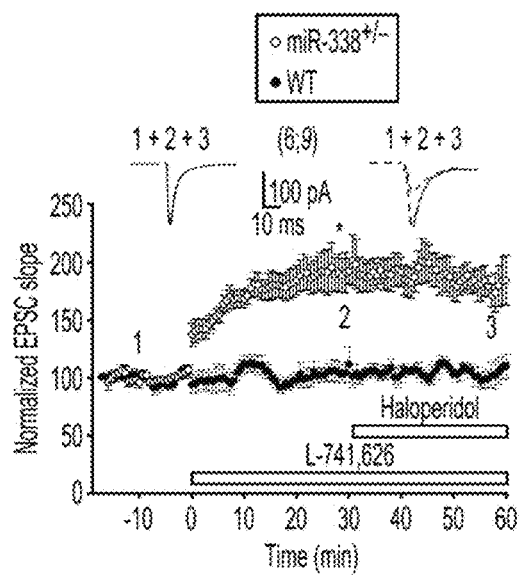
FIG. 6a-6g. Deletion of miR-338 in mice eliminates age dependency for antipsychotics sensitivity and replicates 22q11DS phenotypes. (a) Average TC EPSCs before (1) and during (2-3) application of the Drd2-specific inhibitor L-741,626 and haloperidol in 4-month-old WT (black) and miR-338$^{+/-}$ (white) mice. (b) Haloperidol sensitivity (□H) in WT (black) and miR-338$^{+/-}$ (white) mice between 1.5 and 4 months of age. (c, d) Mean TC EPSCs before (1) and after (2) haloperidol in 2-month-old WT (black) and miR-338$^{+/-}$ (white) mice that received control (c) or Drd2 siRNA injected into their MGv (d). Insets show representative EPSCs. (e-g) Mean PPI of maximal acoustic startle response in 1.5- (e), 2- (f), and 4-month-old (g) WT and miR-338$^{+/-}$ littermates. WT mice are represented by the left black bar and miR-338$^+$ mice are represented by the right gray bar in e-g. Numbers of mice are shown in parentheses (e, WT=22, miR-338$^{+/-}$=21; f, WT=22, miR-338$^{+/-}$=21; g, WT=21, miR-338$^{+/-}$=20). Numbers of neurons or mice are shown inside parentheses, with the number of WT mice/neurons first. Data are represented as the mean±SEM. SPL, sound pressure level. *p<0.05.
Figure 11A:
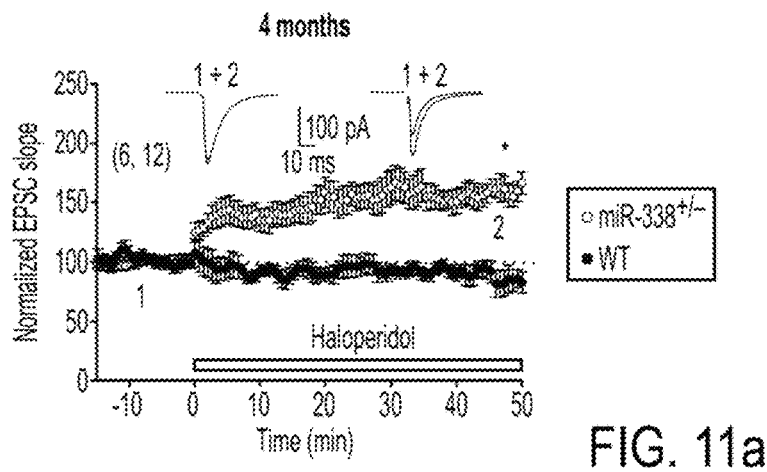
FIG. 11a-11c. Deletion of miR-338 eliminates age dependency for TC sensitivity to antipsychotics. (a-c) Normalized mean TC EPSCs before (1) and after (2) haloperidol application were measured in the MGvs of WT (black) or miR-338$^{+/-}$ (white) mice at 4 months (a), 2 months (b), or 1.5 months (c). Numbers of neurons are shown in parentheses. Insets show representative TC EPSC traces before (1) and after (2) haloperidol application. *p<0.05.
Figure 11B:
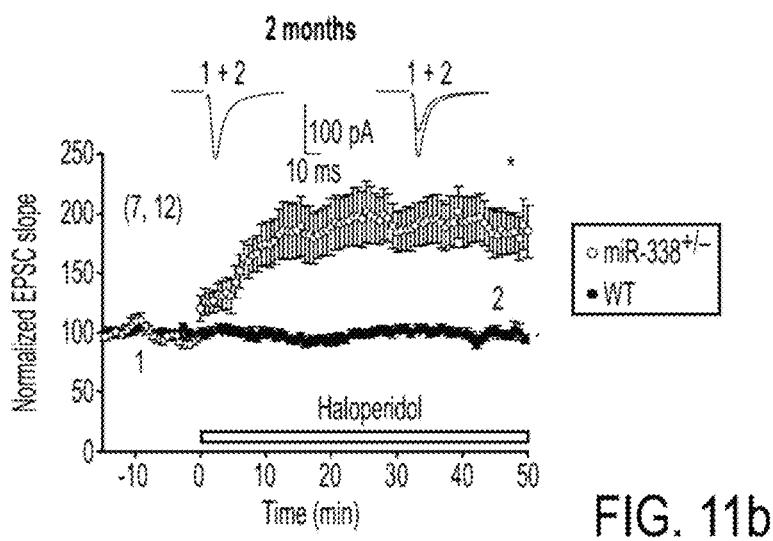
Figure 11C:
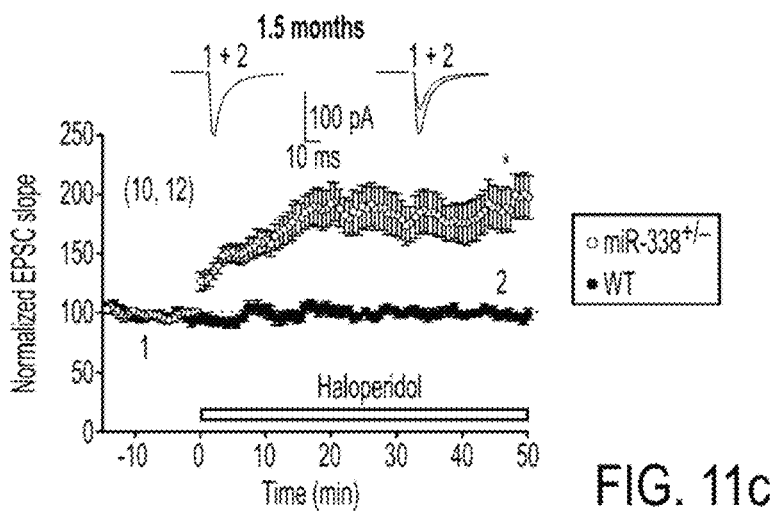
Figure 12A:
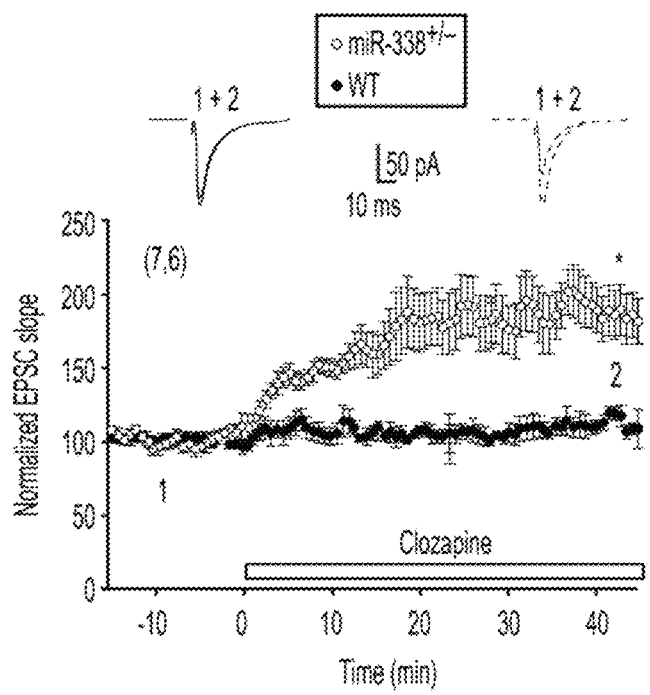
FIG. 12a-12b. Abnormal sensitivity of TC projections in miR-338+/− mice to the antipsychotics clozapine and olanzapine. (a,b) Normalized mean TC EPSCs before (1) and after (2) 40 □M clozapine (a) and 1 □M olanzapine (b) in 3.5-month old WT (black) and miR-338$^{+/-}$ (white) mice. Numbers of neurons are shown in parenthesis, with the number of WT neurons first. Insets show representative TC EPSC traces before and after haloperidol application. *P<0.05.
Figure 12B:
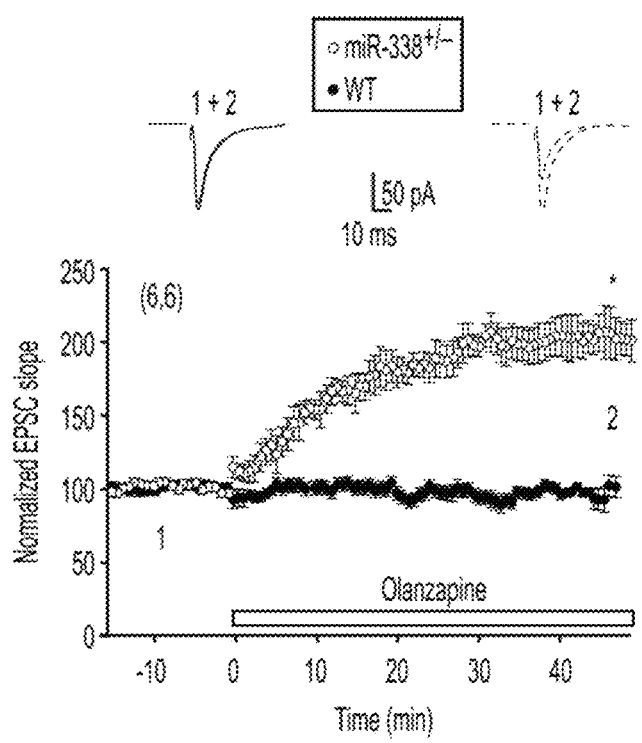

Example 6: miR-338 Depletion Eliminates the Age Dependency of TC Disruption and PPI The deletion of miR-338 was sufficient to upregulate Drd2 in the thalamus, which suggested that depletion of only this miRNA underlies the abnormal sensitivity of TC projections in 22q11DS to antipsychotics. To test this hypothesis, the sensitivity of TC projections in miR-338$^{+/-}$ mice and WT mice was compared. First, it was determined that TC projections of miR-338$^{+/-}$ (white) but not WT (black) mice were sensitive to the Drd2-specific antagonist L-741, 626 (20 nM) (FIG. 6a). In miR-338$^{+/-}$ mice, TC EPSCs substantially increased in response to L-741,626, but that increase was not further elevated by haloperidol. Haloperidol alone increased TC EPSCs in 4-month-old miR-338$^{+/-}$ (white) mice (but not in WT (black) mice) to magnitudes similar to those observed in Df(16)1/+(white) or Dgcr8$^{+/-}$ (gray) mice, suggesting that haloperidol's effect in mutant TC projections was mediated by elevated expression of Drd2 receptors (FIGS. 6b, 11a-11c). Similarly, other antipsychotics (i.e., clozapine and olanzapine) increased TC EPSCs to similar magnitudes in miR-338$^{+/-}$ mice (white) but not WT (black) mice (FIG. 12a-12b).

Figure 13A:
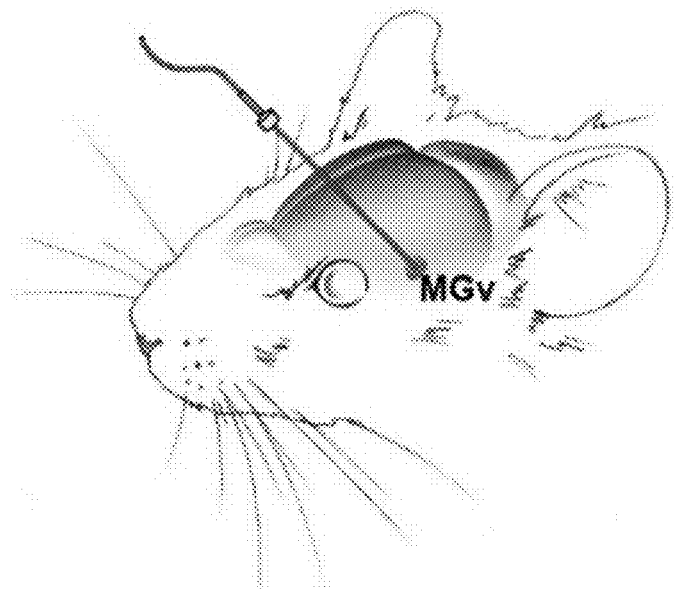
FIG. 13a-13b. Local depletion of miR-338-3p in the MGv renders TC projections to the ACx sensitive to antipsychotics at a younger age. (a) In vivo expression of the miR-338-3p sponge (light gray) or scrambled control (black) after injection into the MGv. (b) Normalized mean TC EPSCs before (1) and after (2) application of haloperidol in 2-month-old WT mice. Numbers of neurons are shown in the parentheses, with the number of WT neurons first. Insets show representative TC EPSC traces before (1) and after (2) haloperidol application. *p<0.05.
Figure 13B:
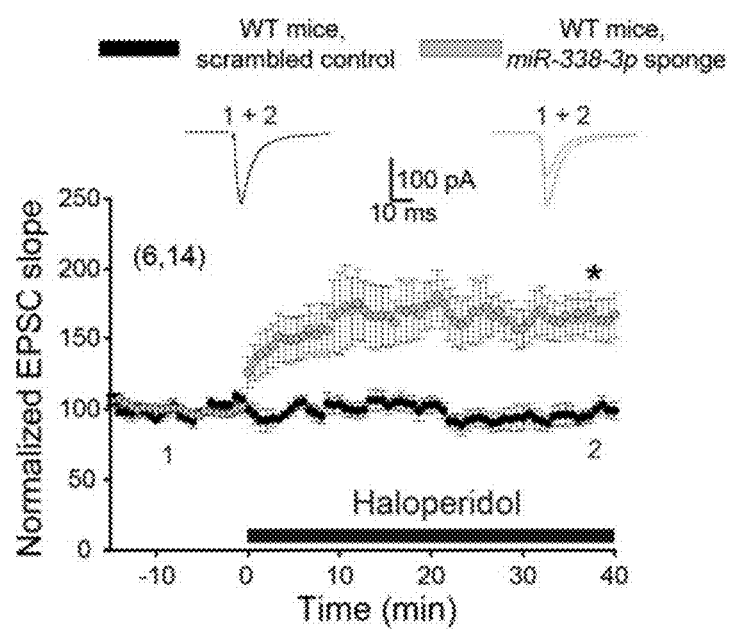
Figure 14A:
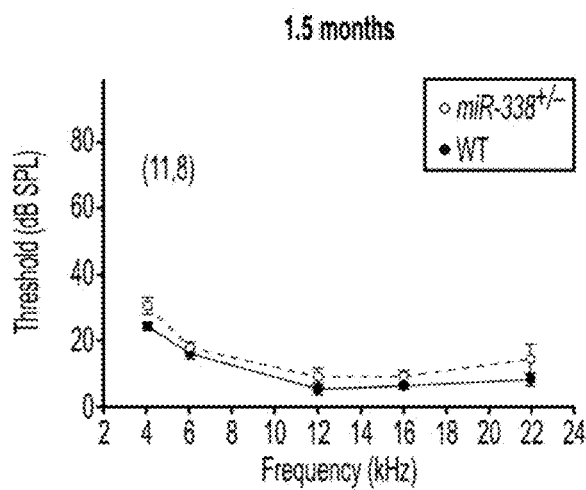
FIG. 14a-14c. Normal hearing in miR-338$^{+/-}$ mice. (a-c) Auditory brainstem responses in WT (black) and miR-338$^{+/-}$ (white) mice at 1.5 months (a), 2 months (b), and 4 months (c). Numbers of mice are shown in parentheses, with the number of WT mice first.
Figure 14B:
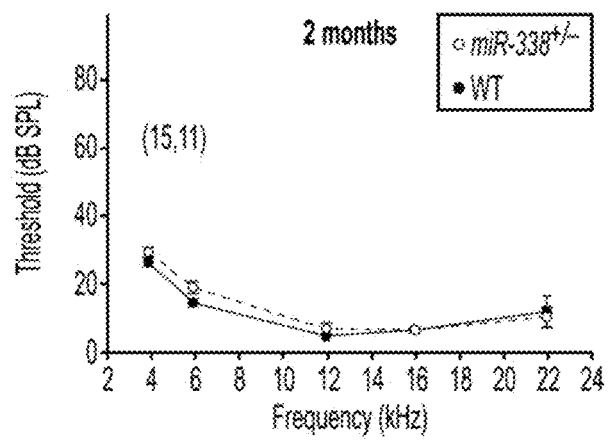
Figure 14C:
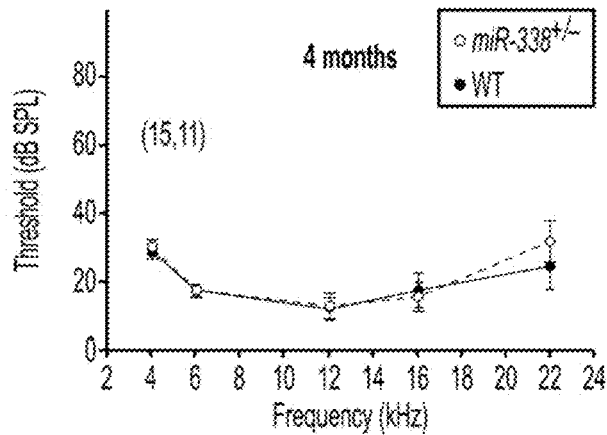
Figure 15A:
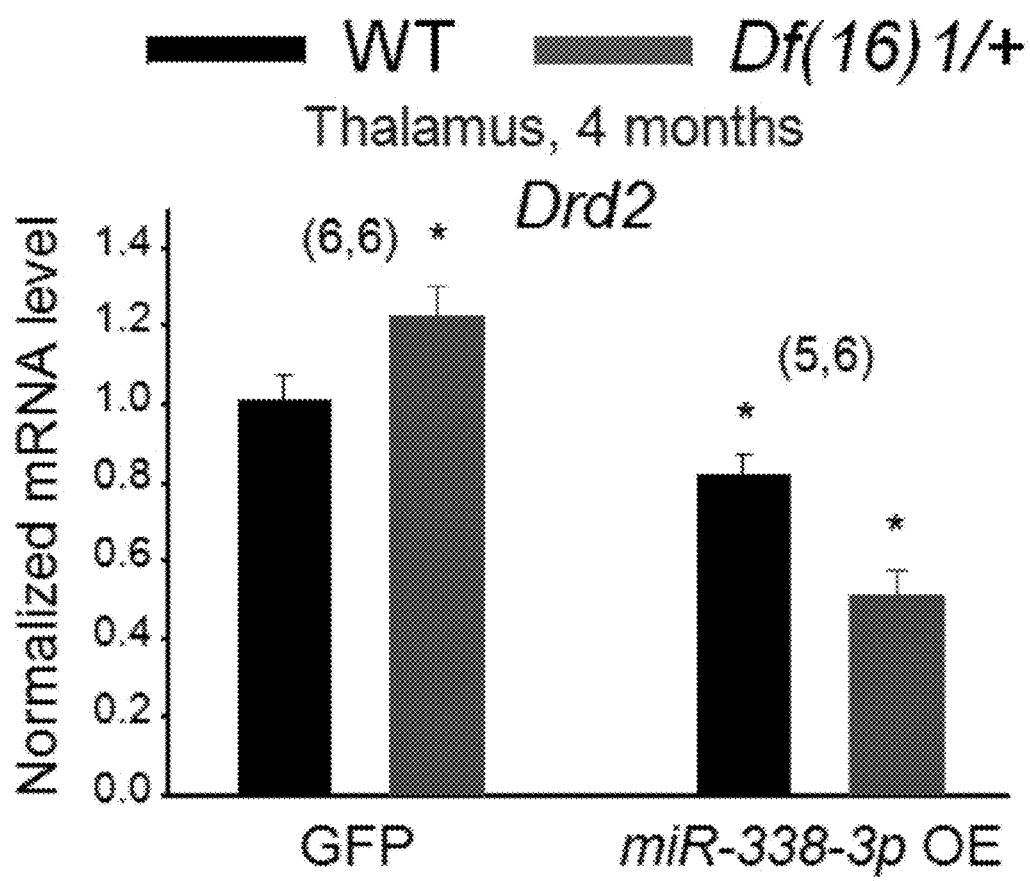
FIG. 15 illustrates that an overexpression of miR-338-3p reduces Drd2 levels in the MGv. Average levels of Drd2 mRNA normalized to U6 in the MGv of 4-month-old WT (left black bar) and Df(16)1/+ (right gray bar) mice injected with AAVs overexpressing a control vector (GFP) or miR-338-3p. *P<0.05.

Unlike Df(16)1/+ or Dgcr8$^{+/-}$ mice, miR-338$^{+/-}$ mice (white) became sensitive to haloperidol in an age-independent manner (FIGS. 6b, 11a-11c). Furthermore, in young (2-month-old) WT mice, TC projections became sensitive to haloperidol when the miR-338-3p sponge (light gray) was expressed in the MGv (FIG. 13a,13b), indicating that depletion of miR-338-3p in the MGv is sufficient for sensitivity to antipsychotics. TC sensitivity to haloperidol in 2-month-old miR-338$^{+/-}$ (white) mice was eliminated by expression of small inhibitory RNA (siRNA) against Drd2 (but not a control siRNA) in the MGv relative to WT (black) mice (FIG. 6c,6d), which further indicated that miR-338-3p is sufficient to regulate Drd2 in the thalamus regardless of age. Similarly, miR-338$^{+/-}$ mice (right gray bars) were deficient in PPI compared to that in WT controls (left black bars), and this deficit was observed at all tested time points (1.5, 2, and 4 months) (FIG. 6e-6g). The defect in PPI was not caused by peripheral hearing defects because the acoustic brainstem-response testing showed no differences between miR-338$^{+/-}$ (white) and WT (black) mice at these ages (FIG. 14a-14c).

Figure 6B:
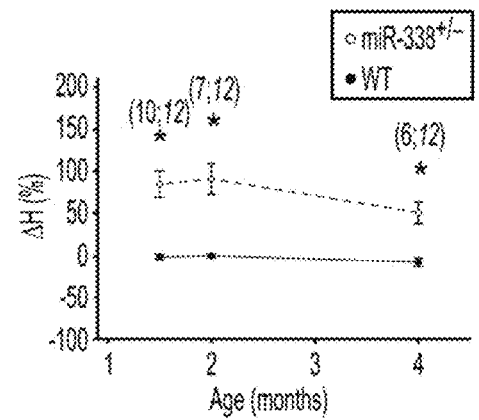
Figure 6C:
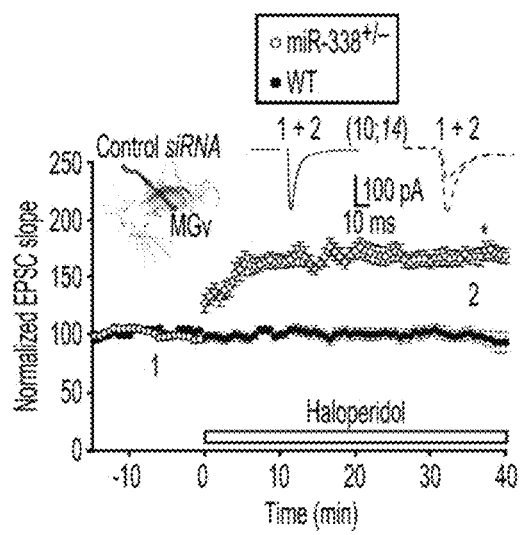
Figure 6D:
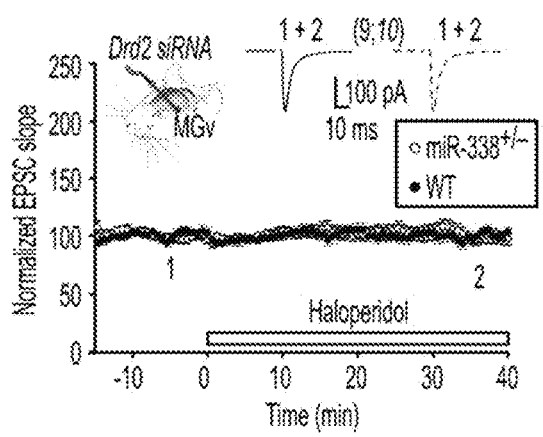
Figure 6E:
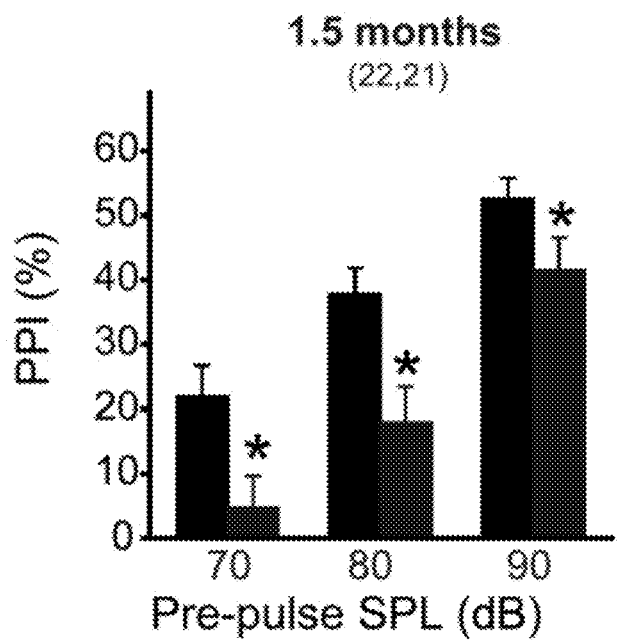
Figure 6F:
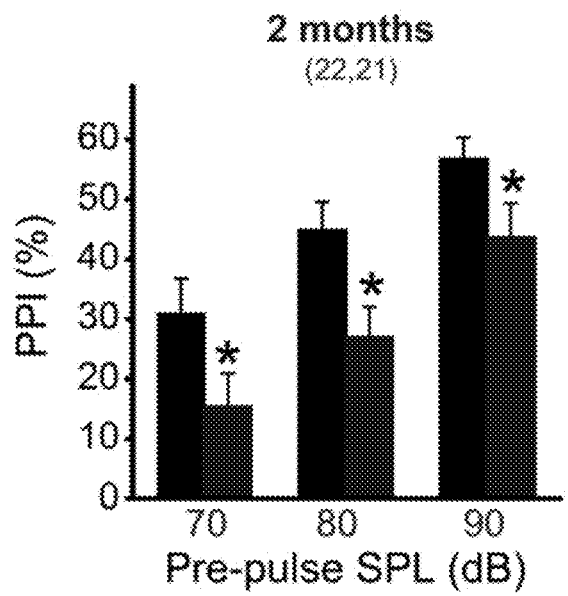
Figure 6G:
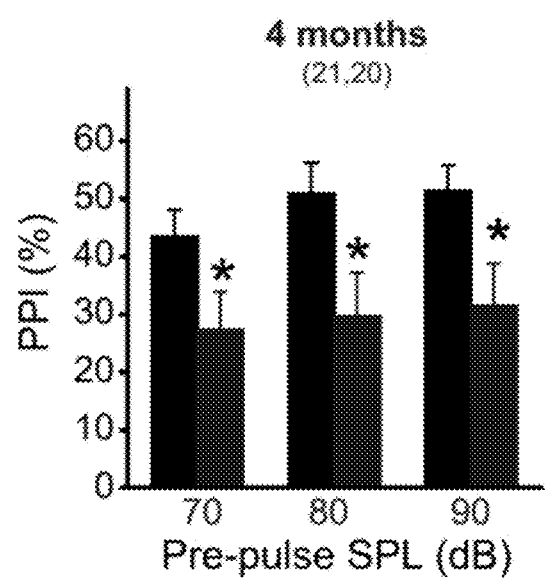

Like the TC projections in Df(16)1/+ mice and Dgcr8$^{+/-}$ mice, those in miR-338$^{+}$ (white) mice showed abnormal sensitivity to haloperidol relative to WT (black) mice (FIG. 6a,6b; FIG. 11), or other antipsychotics (clozapine and olanzapine) (FIG. 12a-12b; data from WT mice shown in black and data from miR-338$^{+/-}$ mice shown in white), and that sensitivity was mediated by Drd2 receptors. Indeed, TC EPSCs were substantially increased in the presence of the specific Drd2 inhibitor L-741,626 (20 nM), and this increase was not further elevated by haloperidol (FIG. 6a). Haloperidol alone also increased TC EPSCs in 4-month-old miR-338$^{+}$ (white) mice relative to WT (black) mice (FIG. 11a) to magnitudes similar to that observed in Df(16)1/+ or Dgcr8$^{+/-}$ mice (p>0.05). However, in contrast to Df(16)1/+ or Dgcr8$^{+/-}$ mice, miR-338$^{+/-}$ mice became sensitive to haloperidol in an age-independent manner (FIG. 6b; FIG. 11a-11c; in these figures, data from WT mice are represented in black while data from miR-338$^{+/-}$ mice are represented in white). Furthermore, TC projections became sensitive to haloperidol in 2-month-old WT mice when the miR-338-3p sponge (light gray) but not the scrambled control (black) was expressed in the MGv (FIG. 13a,13b). TC sensitivity to haloperidol in 2-month-old miR-338$^{+/-}$ (white) mice was eliminated by local MGv expression short hairpin RNA (shRNA) against Drd2 (but not control shRNA) relative to WT (black) mice (FIG. 6c, 6d). Similarly, miR-338$^{+/-}$ mice (right gray bars) were deficient in PPI compared to WT controls (left black bars), and this deficit was observed at early time points (1.5, 2 and 4 months) (FIG. 6e-6h). Acoustic brainstem response (ABR) showed no hearing deficits in miR-338$^{+/-}$ (white) mice at these ages relative to WT (black) mice (FIG. 14).

Example 7: Prepulse Inhibition (PPI) in miR-338 Mice

Mouse Behavioral Tests.
PPI experiments were performed as previously described[6]. Briefly, each day before testing, the mice were allowed a 1 hour habituation period in the testing room, after being transported from the animal-housing room. Before experiments were initiated, the mice were allowed to acclimate to the Plexiglas restraint chamber (6 cm×6 cm×4.8 cm) for 20 min. The mice had a 5-min acclimation period to a 65-dB background white noise, which played throughout the session. For PPI experiments, three acoustic startles (8 kHz, 120 dB, 40 ms) were delivered separated by a 15-s intertrial interval. The testing session consisted of 39 trials of 5 trial types: pulse-alone in which the startle pulse was presented, the combination of a 40-ms prepulse (74 dB, 82 dB, or 90 dB) in WT and Dgcr8$^{+/-}$ littermates and (70 dB, 80 dB, 90 dB) in WT and miR-338$^{+/-}$ littermates and preceding the startle pulse by 100 ms, and no stimuli. Trials were separated by 15 s and presented in a pseudo-random order. PPI was calculated as follows: 100× (pulse-alone response−prepulse+pulse response)/pulse-alone response.

miR-338$^{+/-}$ mice (right gray bars) were deficient in PPI compared to WT controls (left gray bars), and this deficit was observed at early time points (1.5 and 2 months) (FIG. 6e,6f). Acoustic brainstem response (ABR) showed no hearing deficits in miR-338$^{+/-}$ (white) mice at these ages relative to WT (black) mice (FIG. 14a-14c).

Example 8: Nasal Delivery of miR-338-3p Mimic

The miR-338-3p mimic (double-stranded synthetic RNA, 22nt in length) UCCAGCAUCAGUGAUUUUGUUG (SEQ ID NO: 1; the same sequence as the sequence of the mature miR-338-3p) was purchased from GE Dharmacon (Cat# c-310547-07-0020). The mimic was resuspended in nuclease-free water to make a stock solution at 1.41 µg/µl. The working solution was 0.25 µg/µl in PBS (PBS: 137 mM NaCl, 2.7 mM KCl, 4.3 mM $Na_2HPO_4$, 1.47 mM $KH_2PO_4$, pH of 7.4). 10 µl of working solution was intranasally injected to each nostril of a mouse. miR-338-3p levels were then measured at different time points in different brain regions using quantitative RT-PCR (qRT-PCR). It was found that the miR-338-3p mimic accumulates in the thalamus but not hippocampus or cortex or striatum after 10 minutes after delivery.

CONCLUSIONS

These data indicate that miR-338-3p is the miRNA that mediates the Dgcr8-miRNA-Drd2 pathogenic pathway in TC projections to the ACx. Dgcr8 haploinsufficiency in 22q11DS depletes this thalamus-enriched miRNA, which leads to Drd2 upregulation in thalamic-relay neurons. Several studies have indicated that drug-naïve schizophrenic patients have elevated levels of DRD2s in their brains[25, 28]. Drd2 upregulation leads to deficits in TC synaptic transmission and acoustic startle and also renders TC projections sensitive to antipsychotics. Antipsychotics that effectively treat only positive symptoms but not cognitive or negative symptoms of the disease[29], eliminate synaptic deficits at TC projections and acoustic-startle deficiency in 22q11DS mice[6]. Although miR-338-3p is depleted from the auditory thalamus at all ages in 22q11DS mice, it declines even more with age and reaches a low enough level in young adult 22q11DS mice to trigger Drd2 upregulation and TC and acoustic-startle deficiencies. This suggests that miR-338-3p is the key regulator of the late onset of positive symptoms of 22q11DS-associated schizophrenia. Antipsychotics alleviate positive symptoms of schizophrenia through systemic inhibition of DRD2, which is accompanied by multiple and sometimes devastating side effects[2, 30]. The data provided herein suggest that replenishing miR-338-3p in the thalamus of schizophrenic patients could be a promising and more tolerable therapeutic approach to treating schizophrenia-associated psychosis.

The recent identification of disrupted glutamatergic synaptic transmission at thalamic inputs to the ACx in 22q11DS mice[39] suggests that TC disruption could be a pathogenic mechanism that mediates the susceptibility to positive psychotic symptoms in 22q11DS-related schizophrenia for the following reasons: 1) TC disruption in 22q11DS mice is rescued by antipsychotic medications that are Drd2 antagonists and effectively treat predominantly psychotic symptoms but not cognitive or negative symptoms of schizophrenia[82-84]. This disruption was specific to auditory TC projections and was not observed at other glutamatergic projections (i.e., hippocampal, corticocortical, or corticofugal projections) that may be involved in cognitive, social, or motivational tasks. 2) TC disruption in 22q11DS mice is caused by abnormal elevation of Drd2 mRNA and Drd2 protein levels in the TC neurons in the thalamus, a brain region previously linked to psychotic symptoms of schizophrenia[85-88]. The increase in dopamine signaling in the thalamus was also described in schizophrenic patients[89], and studies have indicated that drug-naïve schizophrenic patients have elevated levels of DRD2s in other brain regions[90, 91]. Furthermore, theoretical and empirical studies have proposed that deficient connectivity and abnormal patterns of activity in TC projections contribute to the pathogenesis of the disease[92-101]. Moreover, a local ischemic infarction that disrupts auditory TC projections in a nonpsychotic patient can cause auditory hallucinations[102]. 3) Sensitivity to antipsychotics is observed in the auditory but not the visual or somatosensory TC projections of 22q11DS mice, which is consistent with clinical observations of the substantially higher prevalence of auditory hallucinations, compared with that of hallucinations in other sensory modalities, in schizophrenia[63, 103-105]. Neuroimaging and electrophysiological studies in schizophrenia patients have shown abnormal activation of the auditory thalamus and ACx during auditory hallucinations[35-37, 57, 106-112]; 4) Drd2 elevation only in the auditory thalamus of 22q11DS mice was sufficient to reduce the PPI of the acoustic startle responses, the behavioral endophenotype characteristic of patients with one of several psychiatric diseases, including 22q11DS and schizophrenia[75, 113].

Here it was shown that the disruption of synaptic transmission at auditory TC projections recapitulates another prominent feature of psychotic symptoms. The TC disruption in 22q11DS mice becomes evident only in late juvenile or adult mice, which mirrors clinical manifestations of psychosis in patients with 22q11DS or schizophrenia during late adolescence or early adulthood, typically between the ages of 16 and 30 years[61, 114]. This age-dependent TC decrease in synaptic function is evident in Df(16)1/+ mice, which carry a large microdeletion, and in $Dgcr8^{+/-}$ mice, further strengthening the case that Dgcr8 is the culprit gene, and its haploinsufficiency underlies auditory abnormalities in 22q11DS.

Previous work established that the deletion of one copy of Dgcr8 leads to the elevation of Drd2 in the auditory thalamus[39]. Because Dgcr8 is part of the miRNA-processing machinery, it was hypothesized that a Dgcr8-miRNA-Drd2 mechanism underlies the disruption of TC synaptic transmission. Here miR-338-3p was identified as the mediator of this mechanism. It is also shown herein that miR-338-3p negatively regulated the level of Drd2 in the thalamus. Replenishing miR-338-3p in the thalamus eliminated deficient TC synaptic transmission and abnormal antipsychotic sensitivity of TC projections in 22q11DS mice, and the deletion or auditory thalamus-specific knockdown of miR-338-3p mimicked TC disruption of synaptic transmission and antipsychotic sensitivity in WT mice. Depletion of miR-338-3p is therefore necessary and sufficient to upregulate Drd2, which in turn, reduces glutamate release from thalamic projections, reduces TC synaptic transmission, and renders TC projections sensitive to antipsychotics.

One copy of Dgcr8 is deleted in 22q11DS, in all cells at all ages, so it is unclear why synaptic disruption occurs in projections emanating only from the thalamus and only later in life. The regional specificity most likely arises from the fact that miR-338-3p is substantially enriched in the auditory thalamus compared to other tested brain regions, such as the cortex or hippocampus. Explaining why miR-338-3p is thalamus-enriched will require further investigation. It was also determined that the expression of miR-338-3p is regulated in an age-dependent manner. Although miR-338-3p is depleted in the auditory thalamus in 22q11DS mice at all ages, compared to WT mice, it declines further with age in both 22q11DS and WT mice. Therefore, miR-338-3p expression may be controlled by a combination of Dgcr8- and age-dependent mechanisms. Although it may be possible that Dgcr8 haploinsufficiency reduced the levels of miRNAs, the mechanism of age-dependent miRNA decline is unknown. In the context of Drd2 regulation, a minimal threshold of miR-338-3p expression probably triggers the overexpression of Drd2. In WT mice, miR-338-3p declines during the first few months of life, but it may not reach that threshold. However, in 22q11DS mice, Dgcr8 haploinsufficiency and age-dependent decline in miRNA production drives the miR-338-3p level below this threshold, triggers the elevation of Drd2 in the thalamus, and causes TC synaptic and behavioral deficiencies.

The data provided herein implicate thalamus-enriched miR-338-3p as the key mediator of disruption of synaptic transmission at TC projections and the regulator of the late onset of auditory symptoms of 22q11DS. These data also suggest that replenishment of miR-338-3p in the thalamus could be a more tolerable therapeutic approach for positive symptoms. Current therapy relies upon antipsychotics to alleviate psychosis in schizophrenic patients through systemic inhibition of DRD2, which is accompanied by multiple, and sometimes devastating, side effects[62, 115]. Given that the seed sites of miR-338-3p are conserved between mice and humans and miR-338-3p is depleted in the thalamus of mouse models of 22q11DS and schizophrenic patients, this strategy is potentially applicable to patients. Thus, these results suggest that miR-338-3p is a potential therapeutic target for treating positive symptoms of 22q11DS and related cases of schizophrenia.

TABLE 1

Altered miRNA levels in the auditory thalamus of 2- and 4-month-old Df(16)1/+ and Dgcr8$^{+/-}$ mice compared to respective WT littermates

| | 2 months | | | | 4 months | | | |
|---|---|---|---|---|---|---|---|---|
| miRNA ID* | Df(16)1/+, log$_2$(FC) | Df(16)1/+, −lgP | Dgcr8$^{+/-}$, log$_2$(FC) | Dgcr8$^{+/-}$, −lgP | Df(16)1/+, log$_2$(FC) | Df(16)1/+, −lgP | Dgcr8$^{+/-}$, log$_2$(FC) | Dgcr8$^{+/-}$, −lgP |
| miR-185-5p | −1.64858 | 7.33282 | −0.38928 | 4.36128 | −1.78536 | 13.30000 | −0.50611 | 5.60000 |
| miR-340-5p | −0.45282 | 4.25303 | −0.41144 | 4.74020 | −0.52815 | 7.67000 | −0.43201 | 6.34000 |
| miR-379-5p | −0.52811 | 2.34417 | −0.57980 | 6.79574 | −0.49632 | 5.72000 | −0.56681 | 4.75000 |
| miR-337-5p | −0.43430 | 3.43963 | −0.44315 | 3.97221 | −0.49290 | 4.79000 | −0.38033 | 5.28000 |
| miR-874-3p | −0.22839 | 1.35784 | −0.36327 | 6.04564 | −0.42984 | 3.50689 | −0.32809 | 3.01403 |
| miR-151-5p | −0.29580 | 2.62959 | −0.15935 | 1.22879 | −0.42306 | 5.32000 | −0.42340 | 3.84858 |
| miR-490-5p | −0.29997 | 3.33885 | −0.30096 | 4.76328 | −0.40860 | 2.66448 | −0.28810 | 2.79992 |
| miR-337-3p | −0.72594 | 3.88408 | −0.53059 | 4.67241 | −0.40453 | 3.51575 | −0.56095 | 5.32000 |
| miR-194-5p | −0.09643 | 0.49292 | −0.19463 | 2.31803 | −0.39231 | 4.47000 | −0.14971 | 1.17787 |
| miR-412-3p | −0.26047 | 1.19135 | −0.02458 | 0.15986 | −0.38210 | 2.74342 | −0.49977 | 5.77000 |
| miR-186-5p | −0.30806 | 3.30560 | −0.35820 | 4.20053 | −0.36877 | 4.54000 | −0.29587 | 3.81030 |
| miR-376c-3p | −0.44510 | 2.65559 | −0.37691 | 3.55672 | −0.36565 | 2.38980 | −0.25579 | 3.25004 |
| miR-491-3p | −0.02866 | 0.17304 | −0.02291 | 0.16779 | −0.36420 | 2.31817 | −0.28696 | 3.82584 |
| miR-873a-5p | −0.39810 | 2.22932 | −0.46513 | 2.86648 | −0.35986 | 3.16223 | −0.44403 | 3.82988 |
| miR-378a-3p | −0.02597 | 0.03877 | −0.29050 | 2.03499 | −0.35799 | 1.17895 | −0.12968 | 0.58938 |
| miR-674-3p | −0.40665 | 2.47569 | −0.26268 | 3.18660 | −0.34936 | 3.18669 | −0.38926 | 4.33000 |
| miR-411-5p | −0.52946 | 5.45327 | −0.48809 | 5.03545 | −0.34928 | 2.50056 | −0.51329 | 5.49000 |
| miR-99b-5p | 0.04461 | 0.17949 | −0.16827 | 2.00753 | −0.34897 | 3.38707 | −0.14851 | 1.83458 |
| miR-361-5p | −0.26047 | 2.24137 | −0.18554 | 2.30066 | −0.34870 | 4.91000 | −0.24978 | 3.89852 |
| miR-341-3p | −0.24355 | 1.77885 | −0.24290 | 2.95254 | −0.33562 | 6.25000 | −0.30452 | 4.68000 |
| miR-338-3p | −0.19175 | 1.36799 | −0.10823 | 0.99242 | −0.33405 | 3.04168 | −0.21677 | 2.55006 |
| miR-674-5p | −0.17303 | 1.19746 | −0.17643 | 2.94184 | −0.33270 | 4.40000 | −0.16778 | 3.25601 |
| miR-488-5p | −0.00195 | 0.00805 | −0.02020 | 0.21260 | −0.32913 | 2.05711 | −0.25677 | 2.89363 |
| miR-323-3p | −0.37096 | 1.82575 | −0.37050 | 4.17116 | −0.32876 | 2.97886 | −0.36882 | 3.56822 |
| miR-218-5p | −0.17671 | 0.99892 | −0.11072 | 1.71566 | −0.31911 | 4.28000 | −0.30454 | 2.68477 |
| miR-27b-3p | −0.04949 | 0.17414 | −0.08396 | 0.44242 | −0.30721 | 2.57126 | −0.08052 | 0.23717 |
| miR-539-3p | 0.14778 | 0.70416 | 0.00498 | 0.03638 | −0.29926 | 4.58000 | −0.35779 | 3.54966 |
| miR-25-3p | −0.22723 | 1.88239 | −0.27461 | 2.63331 | −0.29755 | 3.10974 | −0.32216 | 2.98604 |

TABLE 1-continued

Altered miRNA levels in the auditory thalamus of 2- and 4-month-old Df(16)1/+ and Dgcr8$^{+/-}$ mice compared to respective WT littermates

| | 2 months | | | | 4 months | | | |
|---|---|---|---|---|---|---|---|---|
| miRNA ID* | Df(16)1/+, log$_2$(FC) | Df(16)1/+, −lgP | Dgcr8$^{+/-}$, log$_2$(FC) | Dgcr8$^{+/-}$, −lgP | Df(16)1/+, log$_2$(FC) | Df(16)1/+, −lgP | Dgcr8$^{+/-}$, log$_2$(FC) | Dgcr8$^{+/-}$, −lgP |
| miR-329-3p | −0.56459 | 2.21457 | −0.41486 | 3.46643 | −0.27725 | 1.71625 | −0.55649 | 4.08000 |
| miR-148b-3p | −0.34932 | 2.27549 | −0.20795 | 2.63388 | −0.27550 | 1.74510 | −0.33757 | 5.00000 |
| miR-134-5p | −0.09379 | 0.47169 | −0.15267 | 2.72667 | −0.27550 | 3.62664 | −0.11857 | 1.85538 |
| miR-219-5p | −0.24707 | 0.70032 | 0.13979 | 0.47249 | −0.27438 | 2.96830 | −0.03437 | 0.15228 |
| miR-130b-3p | −0.16519 | 1.40819 | −0.29858 | 3.87589 | −0.27129 | 5.18000 | −0.33165 | 6.06000 |
| miR-331-3p | −0.27610 | 2.75741 | −0.25452 | 2.60266 | −0.26460 | 3.51172 | −0.42086 | 6.19000 |
| miR-299b-5p | −0.64210 | 2.95443 | −0.40837 | 3.10344 | −0.26125 | 2.45913 | −0.44087 | 5.20000 |
| miR-409-5p | −0.34006 | 2.92694 | −0.39965 | 2.87777 | −0.25815 | 1.83035 | −0.45668 | 6.03000 |
| miR-374c-5p | −0.40264 | 1.96791 | −0.42464 | 3.88306 | −0.25437 | 1.92815 | −0.41823 | 2.04837 |
| miR-362-3p | −0.40304 | 1.70048 | −0.09342 | 0.44505 | −0.24979 | 3.65603 | −0.22090 | 1.98880 |
| miR-582-5p | −0.30107 | 2.91016 | −0.35764 | 4.56001 | −0.24543 | 2.26635 | −0.28238 | 3.74804 |
| miR-21a-5p | −0.22531 | 1.42508 | 0.00924 | 0.06228 | −0.23955 | 2.13251 | −0.11702 | 1.30260 |
| miR-378a-5p | −0.09892 | 0.28496 | −0.18501 | 2.43253 | −0.23859 | 1.35479 | −0.19665 | 1.25410 |
| miR-410-3p | −0.04583 | 0.26667 | −0.14896 | 0.98136 | −0.23242 | 1.70776 | −0.43218 | 5.01000 |
| miR-382-5p | −0.21794 | 1.92872 | −0.16890 | 1.89499 | −0.23210 | 1.18307 | −0.35547 | 4.17000 |
| miR-342-3p | −0.30374 | 1.52055 | −0.46348 | 4.30075 | −0.22559 | 1.61458 | −0.23434 | 2.68110 |
| miR-532-5p | −0.33157 | 5.00883 | −0.28830 | 2.44847 | −0.22199 | 2.52259 | −0.29624 | 2.28342 |
| miR-98-5p | −0.36761 | 1.74004 | −0.18848 | 2.26707 | −0.21721 | 1.25601 | −0.21391 | 1.76160 |
| miR-3072-3p | −0.21737 | 2.06707 | −0.14584 | 1.67723 | −0.21292 | 2.69576 | −0.19259 | 3.33974 |
| miR-192-5p | −0.32267 | 2.33187 | −0.08968 | 0.89149 | −0.21239 | 2.14488 | −0.24133 | 2.15092 |
| miR-874-5p | −0.18357 | 0.79526 | −0.09993 | 1.07675 | −0.20736 | 2.41490 | −0.17490 | 3.89565 |
| miR-376b-5p | −0.47709 | 2.32419 | −0.32841 | 2.75823 | −0.20095 | 0.91922 | −0.24448 | 2.36934 |
| miR-350-3p | −0.50643 | 2.16582 | −0.17792 | 1.73452 | −0.18231 | 1.24276 | −0.45051 | 3.77820 |
| miR-429-3p | 0.02348 | 0.14990 | −0.20844 | 1.35941 | −0.17600 | 1.71161 | −0.36166 | 4.45000 |
| miR-22-3p | −0.17417 | 0.88726 | −0.29421 | 2.71705 | −0.17220 | 1.29505 | −0.24582 | 1.44913 |
| miR-770-3p | −0.20164 | 0.92219 | −0.30581 | 3.22754 | −0.16802 | 0.62078 | −0.11425 | 0.67675 |
| miR-542-3p | −0.17027 | 0.85234 | −0.04392 | 0.30919 | −0.16405 | 1.21733 | −0.35518 | 4.01000 |
| miR-6540-5p | −0.33039 | 2.00301 | −0.23601 | 4.26359 | −0.16165 | 1.32809 | −0.17128 | 4.92000 |
| miR-340-3p | −0.58892 | 1.61555 | −0.36654 | 3.89266 | −0.15710 | 0.69413 | −0.41571 | 4.87000 |
| miR-377-3p | −0.33963 | 2.23645 | −0.29085 | 1.42202 | −0.14901 | 0.55745 | −0.36775 | 4.75000 |
| miR-540-5p | −0.21736 | 2.59828 | −0.29546 | 4.01680 | −0.14786 | 1.95629 | −0.13382 | 2.68864 |
| miR-325-3p | −0.29095 | 3.39477 | −0.28231 | 3.63211 | −0.13984 | 1.73710 | −0.32907 | 4.37000 |
| miR-598-3p | −0.52025 | 1.88248 | −0.20415 | 1.18458 | −0.13708 | 0.49131 | −0.27125 | 2.69229 |
| miR-30e-5p | −0.19170 | 1.94879 | −0.32848 | 5.22315 | −0.13560 | 0.56633 | −0.18913 | 4.03000 |
| miR-380-3p | −0.51339 | 2.83322 | −0.31588 | 2.22996 | −0.13458 | 0.53658 | −0.33725 | 3.23072 |
| miR-872-5p | −0.30866 | 2.73200 | −0.27909 | 2.60025 | −0.13349 | 0.70013 | −0.28532 | 2.58680 |

TABLE 1-continued

Altered miRNA levels in the auditory thalamus of 2- and 4-month-old Df(16)1/+ and Dgcr8$^{+/-}$ mice compared to respective WT littermates

| | 2 months | | | | 4 months | | | |
|---|---|---|---|---|---|---|---|---|
| miRNA ID* | Df(16)1/+, log$_2$(FC) | Df(16)1/+, -lgP | Dgcr8$^{+/-}$, log$_2$(FC) | Dgcr8$^{+/-}$, -lgP | Df(16)1/+, log$_2$(FC) | Df(16)1/+, -lgP | Dgcr8$^{+/-}$, log$_2$(FC) | Dgcr8$^{+/-}$, -lgP |
| miR-590-3p | 0.15738 | 0.75091 | -0.02917 | 0.18579 | -0.12873 | 2.21882 | -0.25609 | 3.35299 |
| miR-672-5p | -0.20029 | 2.88575 | -0.28012 | 2.12609 | -0.11825 | 1.11673 | -0.22881 | 2.48098 |
| miR-369-3p | -0.39108 | 2.24233 | -0.38498 | 2.84318 | -0.10938 | 0.91829 | -0.15479 | 0.64601 |
| miR-7a-1-3p | -0.32283 | 1.46454 | -0.09042 | 0.60102 | -0.10342 | 0.51267 | -0.19373 | 2.15481 |
| miR-154-3p | -0.49966 | 2.01114 | -0.22055 | 2.21980 | -0.09424 | 0.48481 | -0.19292 | 3.36326 |
| miR-379-3p | -0.21497 | 2.16166 | -0.28879 | 5.91856 | -0.08758 | 0.86134 | -0.21315 | 4.12000 |
| miR-708-5p | -0.13213 | 1.19633 | -0.27051 | 3.62166 | -0.08592 | 1.09677 | -0.09455 | 1.94207 |
| miR-541-5p | -0.38645 | 2.46292 | -0.34754 | 4.12669 | -0.07760 | 0.94494 | -0.08278 | 1.30955 |
| miR-1895 | 0.27858 | 2.18624 | 0.31776 | 1.59982 | -0.07710 | 0.36636 | 0.20538 | 1.38773 |
| miR-22-5p | -0.24476 | 1.30886 | -0.16246 | 1.64132 | -0.07575 | 0.45060 | -0.17362 | 2.12231 |
| miR-134-3p | -0.23693 | 0.78101 | -0.08546 | 0.57698 | -0.06132 | 0.65616 | -0.14752 | 2.10755 |
| miR-382-3p | -0.44909 | 2.08070 | -0.15171 | 1.11672 | -0.05920 | 0.18686 | -0.31600 | 3.42649 |
| miR-425-5p | -0.30094 | 3.25247 | -0.27174 | 3.46697 | -0.05856 | 0.97021 | -0.09711 | 1.62695 |
| miR-411-3p | -0.49774 | 3.28048 | -0.53228 | 7.26456 | -0.05174 | 0.98963 | -0.12142 | 1.79691 |
| miR-346-5p | -0.23181 | 3.15968 | -0.19143 | 2.68474 | -0.04945 | 0.49158 | -0.19230 | 2.64636 |
| miR-153-5p | -0.15874 | 1.94310 | -0.30419 | 3.44445 | -0.04745 | 0.27636 | -0.15579 | 3.03991 |
| miR-190a-5p | -0.29029 | 2.33972 | -0.31362 | 2.85912 | -0.04481 | 0.26848 | -0.16720 | 1.34855 |
| miR-544-5p | -0.22132 | 2.62262 | -0.21683 | 2.93229 | -0.03407 | 0.34004 | 0.06247 | 1.25639 |
| miR-3471 | 0.24013 | 2.35467 | 0.17376 | 0.93282 | -0.02954 | 0.19798 | 0.04906 | 0.25493 |
| miR-149-3p | 0.09333 | 1.02888 | 0.24249 | 2.60388 | -0.02659 | 0.10003 | 0.15764 | 2.03132 |
| miR-34a-5p | -0.07092 | 0.19498 | 0.50004 | 2.28343 | -0.02252 | 0.07289 | 0.09950 | 0.28604 |
| miR-496a-3p | -0.34340 | 1.91396 | -0.24799 | 3.73538 | -0.02130 | 0.16834 | 0.03649 | 0.39580 |
| miR-409-3p | -0.34725 | 2.58636 | -0.49010 | 4.49122 | -0.01837 | 0.14513 | -0.00318 | 0.02532 |
| miR-335-3p | -0.29798 | 2.75084 | -0.20560 | 3.02902 | -0.01683 | 0.12972 | -0.13894 | 1.12976 |
| miR-490-3p | -0.30625 | 2.73738 | -0.28681 | 2.82531 | -0.01141 | 0.06426 | 0.01475 | 0.22898 |
| miR-383-3p | -0.21411 | 2.19625 | -0.10800 | 0.90341 | -0.00413 | 0.03477 | -0.06633 | 0.58312 |
| miR-30d-5p | 0.33931 | 2.55178 | 0.17116 | 2.38771 | -0.00367 | 0.02251 | 0.11727 | 1.93914 |
| miR-488-3p | -0.20675 | 2.30971 | -0.33473 | 2.45405 | -0.00313 | 0.02364 | 0.03016 | 0.18918 |
| miR-5130 | 0.20246 | 2.67639 | -0.00745 | 0.02773 | 0.00103 | 0.00609 | 0.03125 | 0.37387 |
| miR-30a-5p | 0.21787 | 1.36947 | 0.13590 | 3.77359 | 0.00838 | 0.03681 | 0.14345 | 2.58741 |
| miR-532-3p | -0.20336 | 1.72588 | -0.18918 | 2.24134 | 0.01114 | 0.07689 | -0.04412 | 0.37793 |
| miR-484 | 0.25507 | 1.73495 | 0.20172 | 2.80090 | 0.01339 | 0.06238 | 0.20716 | 1.28962 |
| miR-320-3p | 0.18748 | 1.13071 | 0.20191 | 2.59032 | 0.03484 | 0.34162 | 0.13569 | 2.03130 |
| miR-1949 | 0.13067 | 0.60288 | 0.24027 | 3.36284 | 0.03821 | 0.30417 | 0.20394 | 1.98905 |
| miR-125a-3p | 0.29640 | 1.90275 | 0.10266 | 0.68995 | 0.03930 | 0.29418 | 0.28082 | 2.05517 |
| miR-5119 | 0.17465 | 1.32435 | 0.26507 | 2.11748 | 0.04429 | 0.50059 | 0.07877 | 1.09644 |

TABLE 1-continued

Altered miRNA levels in the auditory thalamus of 2- and 4-month-old Df(16)1/+ and Dgcr8$^{+/-}$ mice compared to respective WT littermates

| | 2 months | | | | 4 months | | | |
|---|---|---|---|---|---|---|---|---|
| miRNA ID* | Df(16)1/+, log$_2$(FC) | Df(16)1/+, -lgP | Dgcr8$^{+/-}$, log$_2$(FC) | Dgcr8$^{+/-}$, -lgP | Df(16)1/+, log$_2$(FC) | Df(16)1/+, -lgP | Dgcr8$^{+/-}$, log$_2$(FC) | Dgcr8$^{+/-}$, -lgP |
| miR-30b-3p | 0.20526 | 2.30825 | -0.00929 | 0.07818 | 0.04585 | 0.55115 | 0.02587 | 0.22431 |
| miR-384-3p | -0.21385 | 2.65583 | -0.14759 | 1.48268 | 0.05088 | 0.38527 | -0.03325 | 0.25394 |
| miR-466h-3p | 0.37225 | 2.17701 | 0.18741 | 0.69264 | 0.05243 | 0.21414 | 0.23517 | 1.46279 |
| miR-30a-3p | 0.20022 | 1.36951 | 0.14473 | 2.40011 | 0.05288 | 0.47115 | 0.09631 | 1.42419 |
| miR-291b-3p | 0.21574 | 0.85559 | 0.01851 | 0.09757 | 0.05999 | 0.51289 | 0.11816 | 2.21480 |
| miR-1186b | 0.24201 | 1.26108 | 0.24245 | 1.18070 | 0.07062 | 0.50990 | 0.24937 | 2.36667 |
| miR-669n | -0.03443 | 0.19165 | 0.00754 | 0.03275 | 0.07976 | 0.67927 | 0.24220 | 2.14081 |
| miR-3082-5p | 0.13470 | 0.25902 | 0.12509 | 0.30716 | 0.08752 | 0.56557 | 0.28766 | 2.68193 |
| miR-582-3p | -0.36581 | 3.16016 | -0.28702 | 2.84446 | 0.09241 | 0.34283 | 0.31655 | 1.92822 |
| miR-127-3p | 0.31162 | 0.92037 | 0.22463 | 1.39840 | 0.12760 | 0.45312 | 0.24279 | 2.46742 |
| miR-712-5p | 0.19497 | 0.80946 | 0.27763 | 2.87037 | 0.13836 | 0.97133 | 0.13884 | 1.10864 |
| miR-200a-3p | 0.10958 | 0.54329 | -0.20610 | 2.17228 | 0.14003 | 0.80942 | -0.04499 | 0.47935 |
| miR-5117-5p | -0.03307 | 0.09115 | -0.00820 | 0.04658 | 0.15792 | 2.05862 | 0.20996 | 1.07294 |
| miR-664-3p | 0.19179 | 1.06561 | 0.20097 | 3.46731 | 0.16058 | 1.14929 | 0.23420 | 2.64985 |
| miR-138-1-3p | 0.25216 | 3.41325 | 0.26724 | 2.10524 | 0.16076 | 1.43355 | 0.16703 | 1.60822 |
| miR-705 | 0.26694 | 1.80529 | 0.34896 | 2.29776 | 0.17633 | 1.54490 | 0.18320 | 1.05974 |
| miR-1843a-5p | 0.10436 | 0.49439 | 0.11951 | 0.86070 | 0.17902 | 1.43543 | 0.28283 | 3.79383 |
| miR-3095-3p | 0.74549 | 2.33919 | 0.41334 | 1.36465 | 0.18069 | 1.12351 | 0.30474 | 1.03585 |
| miR-3096b-3p | 0.24325 | 3.51385 | 0.19245 | 4.17219 | 0.18643 | 3.05684 | 0.17585 | 2.29537 |
| miR-5113 | 0.76604 | 3.36870 | 0.38103 | 1.67553 | 0.20310 | 1.45130 | 0.20785 | 2.30914 |
| miR-677-3p | 0.21203 | 1.05257 | 0.21105 | 2.54872 | 0.21137 | 2.38834 | 0.29067 | 2.97121 |
| miR-335-5p | -0.42834 | 3.19848 | -0.18503 | 0.86468 | 0.22218 | 1.04593 | -0.22129 | 2.07806 |
| miR-1839-3p | 0.12067 | 1.97001 | 0.18008 | 2.61633 | 0.22866 | 2.69554 | 0.12984 | 1.39494 |
| miR-6402 | -0.02151 | 0.04380 | 0.24261 | 0.49376 | 0.25885 | 1.56379 | 0.25769 | 2.72355 |
| miR-6412 | -0.15807 | 0.24032 | 0.02169 | 0.02769 | 0.30325 | 2.25994 | 0.02768 | 0.14334 |
| miR-1839-5p | 0.18314 | 1.23480 | 0.20845 | 3.05761 | 0.30469 | 3.45981 | 0.16534 | 3.75248 |
| miR-3102-3p | 0.16636 | 1.08130 | 0.35127 | 4.01560 | 0.31541 | 2.93383 | 0.28527 | 4.06000 |
| miR-344b-3p | 0.06893 | 0.36837 | 0.16621 | 1.33117 | 0.43851 | 2.15959 | 0.26669 | 4.20000 |
| miR-135a-5p | -0.17353 | 0.30923 | -0.00480 | 0.01079 | 0.56360 | 2.62229 | 0.30957 | 1.09472 |
| miR-135a-2-3p | 0.04867 | 0.22692 | 0.10553 | 0.51050 | 0.57250 | 2.50032 | 0.09612 | 0.81124 |
| miR-7b-5p | 0.12388 | 0.43545 | 0.05651 | 0.12626 | 0.64985 | 2.30313 | 0.15830 | 0.78228 |

*Only miRNAs with p < 0.01 and log$_2$(FC) > ±0.2 for either 2 or 4 months in Df(16)1/+ or Dgcr8$^{+/-}$ mutants are shown.
FC, fold change in mutant vs. WT mice.
Bold, miRNAs predicted to target Drd2 transcripts.
The data discussed in this publication have been deposited in NCBI's Gene Expression Omnibus and are accessible through GEO Series accession number GSE73981 http://www.ncbi.nlm.nih.gov/geo/query/acc.cgi?token=cpwxugcwdzsdhax&acc=GSE73981.

REFERENCES

1. Mueser, K. T. and McGurk, S. R. "Schizophrenia," *Lancet* 363, 2063 (2004).
2. Lewis, D. A. and Lieberman, J. A. "Catching up on schizophrenia: natural history and neurobiology," *Neuron* 28, 325 (2000).
3. Insel, T. R. "Rethinking schizophrenia," *Nature* 468, 187 (2010).
4. Snyder, S. H. "Drugs for a new millennium," *Philos Trans R Soc Lond B Biol Sci* 354, 1985 (1999).
5. Carlsson, A. "The current status of the dopamine hypothesis of schizophrenia," *Neuropsychopharmacology* 1, 179 (1988).
6. Chun, S., et al. "Specific disruption of thalamic inputs to the auditory cortex in schizophrenia models," *Science* 344, 1178 (2014).
7. Lindsay, E. A., et al. "Congenital heart disease in mice deficient for the DiGeorge syndrome region," *Nature* 401, 379 (1999).
8. Karayiorgou, M., Simon, T. J., and Gogos, J. A. "22q11.2 microdeletions: linking DNA structural variation to brain dysfunction and schizophrenia," *Nat Rev Neurosci* 11, 402 (2010).
9. Pulver, A. E. "Search for schizophrenia susceptibility genes," *Biol Psychiatry* 47, 221 (2000).
10. Chow, E. W., Watson, M., Young, D. A., and Bassett, A. S. "Neurocognitive profile in 22q11 deletion syndrome and schizophrenia," *Schizophr Res* 87, 270 (2006).
11. Scambler, P. J., et al. "Velo-cardio-facial syndrome associated with chromosome 22 deletions encompassing the DiGeorge locus," *Lancet* 339, 1138 (1992).
12. Earls, L. R., et al. "Age-dependent microRNA control of synaptic plasticity in 22q11 deletion syndrome and schizophrenia," *J Neurosci* 32, 14132 (2012).
13. Stark, K. L., et al. "Altered brain microRNA biogenesis contributes to phenotypic deficits in a 22q11-deletion mouse model," *Nat Genet* 40, 751 (2008).
14. Ambros, V. "The functions of animal microRNAs," *Nature* 431, 350 (2004).
15. Lindsay, E. A., et al. "Tbx1 haploinsufficieny in the DiGeorge syndrome region causes aortic arch defects in mice," *Nature* 410, 97 (2001).
16. Pulver, A. E., et al. "Psychotic illness in patients diagnosed with velo-cardio-facial syndrome and their relatives," *J Nerv Ment Dis* 182, 476 (1994).
17. Dierks, T., et al. "Activation of Heschl's gyms during auditory hallucinations," *Neuron* 22, 615 (1999).
18. Silbersweig, D. A., et al. "A functional neuroanatomy of hallucinations in schizophrenia," *Nature* 378, 176 (1995).
19. Horga, G., Schatz, K. C., Abi-Dargham, A., and Peterson, B. S. "Deficits in predictive coding underlie hallucinations in schizophrenia," *J Neurosci* 34, 8072 (2014).
20. Smith, P. H. and Populin, L. C. "Fundamental differences between the thalamocortical recipient layers of the cat auditory and visual cortices," *J Comp Neurol* 436, 508 (2001).
21. Swerdlow, N. R., Weber, M., Qu, Y., Light, G. A., and Braff, D. L. "Realistic expectations of prepulse inhibition in translational models for schizophrenia research," *Psychopharmacology (Berl)* 199, 331 (2008).
22. Braff, D. L., Geyer, M. A., and Swerdlow, N. R. "Human studies of prepulse inhibition of startle: normal subjects, patient groups, and pharmacological studies," *Psychopharmacology (Berl)* 156, 234 (2001).
23. Srikantan, S., Marasa, B. S., Becker, K. G., Gorospe, M., and Abdelmohsen, K. "Paradoxical microRNAs: individual gene repressors, global translation enhancers," *Cell Cycle* 10, 751 (2011).
24. Dweep, H., Sticht, C., Pandey, P., and Gretz, N. "miRWalk—database: prediction of possible miRNA binding sites by "walking" the genes of three genomes," *J Biomed Inform* 44, 839 (2011).
25. Denzler, R., Agarwal, V., Stefano, J., Bartel, D. P., and Stoffel, M. "Assessing the ceRNA hypothesis with quantitative measurements of miRNA and target abundance," *Mol Cell* 54, 766 (2014).
26. Small, E. M. and Olson, E. N. "Pervasive roles of microRNAs in cardiovascular biology," *Nature* 469, 336 (2011).
27. Wong, D. F., et al. "Positron emission tomography reveals elevated D2 dopamine receptors in drug-naive schizophrenics," *Science* 234, 1558 (1986).
28. Abi-Dargham, A., et al. "Increased baseline occupancy of D2 receptors by dopamine in schizophrenia," *Proc Natl Acad Sci USA* 97, 8104 (2000).
29. Miyamoto, S., Miyake, N., Jarskog, L. F., Fleischhacker, W. W., and Lieberman, J. A. "Pharmacological treatment of schizophrenia: a critical review of the pharmacology and clinical effects of current and future therapeutic agents," *Mol Psychiatry* 17, 1206 (2012).
30. Thaker, G. K. and Carpenter, W. T., Jr. "Advances in schizophrenia," *Nat Med* 7, 667 (2001).
31. Christensen, M., Larsen, L. A., Kauppinen, S., and Schratt, G. "Recombinant Adeno-Associated Virus-Mediated microRNA Delivery into the Postnatal Mouse Brain Reveals a Role for miR-134 in Dendritogenesis in Vivo," *Front Neural Circuits* 3, 16 (2010).
32. Kluiver, J., et al. "Generation of miRNA sponge constructs," *Methods* 58, 113 (2012).
33. Kluiver, J., et al. "Rapid generation of microRNA sponges for microRNA inhibition," *PLoS One* 7, e29275 (2012).
34. Mellado Lagarde, M. M., et al. "Spontaneous regeneration of cochlear supporting cells after neonatal ablation ensures hearing in the adult mouse," *Proc Natl Acad Sci USA* 111, 16919 (2014).
35. Dierks, T. et al. Activation of Heschl's gyms during auditory hallucinations. *Neuron.* 22, 615-621 (1999).
36. Silbersweig, D. A. et al. A functional neuroanatomy of hallucinations in schizophrenia. *Nature.* 378, 176-179 (1995).
37. Horga, G., Schatz, K. C., Abi-Dargham, A., & Peterson, B. S. Deficits in predictive coding underlie hallucinations in schizophrenia. *J. Neurosci.* 34, 8072-8082 (2014).
38. Javitt, D. C. & Sweet, R. A. Auditory dysfunction in schizophrenia: integrating clinical and basic features. *Nat. Rev. Neurosci.* 16, 535-550 (2015).
39. Chun, S. et al. Specific disruption of thalamic inputs to the auditory cortex in schizophrenia models. *Science.* 344, 1178-1182 (2014).
40. Lindsay, E. A. et al. Congenital heart disease in mice deficient for the DiGeorge syndrome region. *Nature.* 401, 379-383 (1999).
41. Bassett, A. S. et al. Practical guidelines for managing patients with 22q11.2 deletion syndrome. *J. Pediatr.* 159, 332-339 (2011).
42. Costain, G., McDonald-McGinn, D. M., & Bassett, A. S. Prenatal genetic testing with chromosomal microarray analysis identifies major risk variants for schizophrenia and other later-onset disorders. *Am. J. Psychiatry* 170, 1498 (2013).

43. Kaminsky, E. B. et al. An evidence-based approach to establish the functional and clinical significance of copy number variants in intellectual and developmental disabilities. Genet. Med. 13, 777-784 (2011).
44. McDonald-McGinn, D. M. & Sullivan, K. E. Chromosome 22q11.2 deletion syndrome (DiGeorge syndrome/velocardiofacial syndrome). Medicine (Baltimore) 90, 1-18 (2011).
45. Scambler, P. J. et al. Velo-cardio-facial syndrome associated with chromosome 22 deletions encompassing the DiGeorge locus. Lancet 339, 1138-1139 (1992).
46. Karayiorgou, M., Simon, T. J., & Gogos, J. A. 22q11.2 microdeletions: linking DNA structural variation to brain dysfunction and schizophrenia. Nat. Rev. Neurosci 11, 402-416 (2010).
47. Pulver, A. E. Search for schizophrenia susceptibility genes. Biol. Psychiatry 47, 221-230 (2000).
48. Chow, E. W., Watson, M., Young, D. A., & Bassett, A. S. Neurocognitive profile in 22q11 deletion syndrome and schizophrenia. Schizophr. Res. 87, 270-278 (2006).
49. Fung, W. L. et al. Elevated prevalence of generalized anxiety disorder in adults with 22q11.2 deletion syndrome. Am. J. Psychiatry 167, 998 (2010).
50. Gothelf, D. et al. Clinical characteristics of schizophrenia associated with velo-cardio-facial syndrome. Schizophr. Res. 35, 105-112 (1999).
51. Green, T. et al. Psychiatric disorders and intellectual functioning throughout development in velocardiofacial (22q11.2 deletion) syndrome. J. Am. Acad. Child Adolesc. Psychiatry 48, 1060-1068 (2009).
52. Murphy, K. C., Jones, L. A., & Owen, M. J. High rates of schizophrenia in adults with velo-cardio-facial syndrome. Arch. Gen. Psychiatry 56, 940-945 (1999).
53. Pulver, A. E. et al. Psychotic illness in patients diagnosed with velo-cardio-facial syndrome and their relatives. J. Nerv. Ment. Dis. 182, 476-478 (1994).
54. Shprintzen, R. J., Goldberg, R., Golding-Kushner, K. J., & Marion, R. W. Late-onset psychosis in the velo-cardio-facial syndrome. Am. J. Med. Genet. 42, 141-142 (1992).
55. Bassett, A. S., Chow, E. W., & Weksberg, R. Chromosomal abnormalities and schizophrenia. Am. J. Med. Genet. 97, 45-51 (2000).
56. Murphy, K. C. Schizophrenia and velo-cardio-facial syndrome. Lancet 359, 426-430 (2002).
57. Feinstein, C., Eliez, S., Blasey, C., & Reiss, A. L. Psychiatric disorders and behavioral problems in children with velocardiofacial syndrome: usefulness as phenotypic indicators of schizophrenia risk. Biol. Psychiatry 51, 312-318 (2002).
58. Bassett, A. S. et al. Clinical features of 78 adults with 22q11 Deletion Syndrome. Am. J Med. Genet. A 138, 307-313 (2005).
59. Vorstman, J. A., Breetvelt, E. J., Thode, K. I., Chow, E. W., & Bassett, A. S. Expression of autism spectrum and schizophrenia in patients with a 22q11.2 deletion. Schizophr. Res. 143, 55-59 (2013).
60. Schneider, M. et al. Psychiatric disorders from childhood to adulthood in 22q11.2 deletion syndrome: results from the International Consortium on Brain and Behavior in 22q11.2 Deletion Syndrome. Am. J. Psychiatry 171, 627-639 (2014).
61. Mueser, K. T. & McGurk, S. R. Schizophrenia. Lancet 363, 2063-2072 (2004).
62. Lewis, D. A. & Lieberman, J. A. Catching up on schizophrenia: natural history and neurobiology. Neuron. 28, 325-334 (2000).
63. Bauer, S. M. et al. Culture and the prevalence of hallucinations in schizophrenia. Compr. Psychiatry 52, 319-325 (2011).
64. Insel, T. R. Rethinking schizophrenia. Nature. 468, 187-193 (2010).
65. Snyder, S. H. Drugs for a new millennium. Philos. Trans. R. Soc. Lond B Biol. Sci. 354, 1985-1994 (1999).
66. Carlsson, A. The current status of the dopamine hypothesis of schizophrenia. Neuropsychopharmacology. 1, 179-186 (1988).
67. Seeman, P. & Lee, T. Antipsychotic drugs: direct correlation between clinical potency and presynaptic action on dopamine neurons. Science 188, 1217-1219 (1975).
68. Earls, L. R. et al. Age-dependent microRNA control of synaptic plasticity in 22q11 deletion syndrome and schizophrenia. J. Neurosci. 32, 14132-14144 (2012).
69. Fenelon, K. et al. The pattern of cortical dysfunction in a mouse model of a schizophrenia-related microdeletion. J. Neurosci. 33, 14825-14839 (2013).
70. Stark, K. L. et al. Altered brain microRNA biogenesis contributes to phenotypic deficits in a 22q11-deletion mouse model. Nat. Genet 40, 751-760 (2008).
71. Ambros, V. The functions of animal microRNAs. Nature. 431, 350-355 (2004).
72. Earls, L. R. & Zakharenko, S. S. A Synaptic Function Approach to Investigating Complex Psychiatric Diseases. Neuroscientist. 20, 257-271 (2013).
73. Smith, P. H. & Populin, L. C. Fundamental differences between the thalamocortical recipient layers of the cat auditory and visual cortices. J Comp Neurol. 436, 508-519 (2001).
74. Swerdlow, N. R., Weber, M., Qu, Y., Light, G. A., & Braff, D. L. Realistic expectations of prepulse inhibition in translational models for schizophrenia research. Psychopharmacology (Berl) 199, 331-388 (2008).
75. Braff, D. L., Geyer, M. A., & Swerdlow, N. R. Human studies of prepulse inhibition of startle: normal subjects, patient groups, and pharmacological studies. Psychopharmacology (Berl) 156, 234-258 (2001).
76. Dweep, H., Sticht, C., Pandey, P., & Gretz, N. miR-Walk—database: prediction of possible miRNA binding sites by "walking" the genes of three genomes. J. Biomed. Inform. 44, 839-847 (2011).
77. Denzler, R., Agarwal, V., Stefano, J., Bartel, D. P., & Stoffel, M. Assessing the ceRNA hypothesis with quantitative measurements of miRNA and target abundance. Mol. Cell 54, 766-776 (2014).
78. Small, E. M. & Olson, E. N. Pervasive roles of microRNAs in cardiovascular biology. Nature. 469, 336-342 (2011).
79. Chun, S., Bayazitov, I. T., Blundon, J. A., & Zakharenko, S. S. Thalamocortical long-term potentiation becomes gated after the early critical period in the auditory cortex. J. Neurosci. 33, 7345-7357 (2013).
80. Emptage, N. J., Reid, C. A., Fine, A., & Bliss, T. V. Optical quantal analysis reveals a presynaptic component of LTP at hippocampal Schaffer-associational synapses. Neuron 38, 797-804 (2003).
81. Richardson, R. J., Blundon, J. A., Bayazitov, I. T., & Zakharenko, S. S. Connectivity patterns revealed by mapping of active inputs on dendrites of thalamorecipient neurons in the auditory cortex. J Neurosci. 29, 6406-6417 (2009).
82. Conn, P. J., Tamminga, C., Schoepp, D. D., & Lindsley, C. Schizophrenia: moving beyond monoamine antagonists. Mol. Interv. 8, 99-107 (2008).

83. Leucht, S. et al. Second-generation versus first-generation antipsychotic drugs for schizophrenia: a meta-analysis. Lancet 373, 31-41 (2009).
84. Miyamoto, S Miyake, N., Jarskog, L. F., Fleischhacker, W. W., & Lieberman, J. A. Pharmacological treatment of schizophrenia: a critical review of the pharmacology and clinical effects of current and future therapeutic agents. Mol. Psychiatry 17, 1206-1227 (2012).
85. Clinton, S. M. & Meador-Woodruff, J. H. Thalamic dysfunction in schizophrenia: neurochemical, neuropathological, and in vivo imaging abnormalities. Schizophr. Res. 69, 237-253 (2004).
86. Cronenwett, W. J. & Csernansky, J. Thalamic pathology in schizophrenia. Curr. Top. Behav. Neurosci 4, 509-528 (2010).
87. Ettinger, U. et al. Magnetic resonance imaging of the thalamus and adhesio interthalamica in twins with schizophrenia. Arch. Gen. Psychiatry 64, 401-409 (2007).
88. Parnaudeau, S. et al. Inhibition of mediodorsal thalamus disrupts thalamofrontal connectivity and cognition. Neuron. 77, 1151-1162 (2013).
89. Oke, A. F., Adams, R. N., Winblad, B., & von, K. L. Elevated dopamine/norepinephrine ratios in thalami of schizophrenic brains. Biol. Psychiatry 24, 79-82 (1988).
90. Wong, D. F. et al. Positron emission tomography reveals elevated D2 dopamine receptors in drug-naive schizophrenics. Science. 234, 1558-1563 (1986).
91. Abi-Dargham, A. et al. Increased baseline occupancy of D2 receptors by dopamine in schizophrenia. Proc. Natl. Acad. Sci. U. S. A 97, 8104-8109 (2000).
92. Andreasen, N. C. et al. Schizophrenia and cognitive dysmetria: a positron-emission tomography study of dysfunctional prefrontal-thalamic-cerebellar circuitry. Proc. Natl. Acad. Sci. U. S. A 93, 9985-9990 (1996).
93. Behrendt, R. P. Hallucinations: synchronisation of thalamocortical gamma oscillations underconstrained by sensory input. Conscious. Cogn 12, 413-451 (2003).
94. Lisman, J. E., Pi, H. J., Zhang, Y., & Otmakhova, N. A. A thalamo-hippocampal-ventral tegmental area loop may produce the positive feedback that underlies the psychotic break in schizophrenia. Biol. Psychiatry 68, 17-24 (2010).
95. Llinas, R. & Ribary, U. Coherent 40-Hz oscillation characterizes dream state in humans. Proc. Natl. Acad. Sci. U. S. A 90, 2078-2081 (1993).
96. Llinas, R. R. & Pare, D. Of dreaming and wakefulness. Neuroscience 44, 521-535 (1991).
97. Marenco, S. et al. Investigation of anatomical thalamocortical connectivity and FMRI activation in schizophrenia. Neuropsychopharmacology 37, 499-507 (2012).
98. Welsh, R. C., Chen, A. C., & Taylor, S. F. Low-frequency BOLD fluctuations demonstrate altered thalamocortical connectivity in schizophrenia. Schizophr. Bull. 36, 713-722 (2010).
99. Woodward, N. D., Karbasforoushan, H., & Heckers, S. Thalamocortical dysconnectivity in schizophrenia. Am. J Psychiatry 169, 1092-1099 (2012).
100. Schulman, C. A., Richlin, M., & Weinstein, S. Hallucinations and disturbances of affect, cognition, and physical state as a function of sensory deprivation. Percept. Mot. Skills 25, 1001-1024 (1967).
101. Cheng, W. et al. Voxel-based, brain-wide association study of aberrant functional connectivity in schizophrenia implicates thalamocortical circuitry. Schizophrenia. 1, (2015).
102. Woo, P. Y., Leung, L. N., Cheng, S. T., & Chan, K. Y. Monoaural musical hallucinations caused by a thalamocortical auditory radiation infarct: a case report. J. Med. Case. Rep. 8, 400 (2014).
103. Mueser, K. T., Bellack, A. S., & Brady, E. U. Hallucinations in schizophrenia. Acta Psychiatr. Scand. 82, 26-29 (1990).
104. Ndetei, D. M. & Vadher, A. A comparative cross-cultural study of the frequencies of hallucination in schizophrenia. Acta Psychiatr. Scand. 70, 545-549 (1984).
105. Small, I. F., Small, J. G., & Andersen, J. M. Clinical characteristics of hallucinations of schizophrenia. Dis. Nerv. Syst. 27, 349-353 (1966).
106. Hoffman, R. E., Pittman, B., Constable, R. T., Bhagwagar, Z., & Hampson, M. Time course of regional brain activity accompanying auditory verbal hallucinations in schizophrenia. Br. J. Psychiatry 198, 277-283 (2011).
107. Lennox, B. R., Park, S. B., Medley, I., Morris, P. G., & Jones, P. B. The functional anatomy of auditory hallucinations in schizophrenia. Psychiatry Res. 100, 13-20 (2000).
108. Sommer, I. E. et al. Auditory verbal hallucinations predominantly activate the right inferior frontal area. Brain 131, 3169-3177 (2008).
109. Woodruff, P. et al. Auditory hallucinations and perception of external speech. Lancet 346, 1035 (1995).
110. Hubl, D., Koenig, T., Strik, W. K., Garcia, L. M., & Dierks, T. Competition for neuronal resources: how hallucinations make themselves heard. Br. J. Psychiatry 190, 57-62 (2007).
111. Ford, J. M. et al. Tuning in to the voices: a multisite FMRI study of auditory hallucinations. Schizophr. Bull. 35, 58-66 (2009).
112. Kompus, K., Westerhausen, R., & Hugdahl, K. The "paradoxical" engagement of the primary auditory cortex in patients with auditory verbal hallucinations: a meta-analysis of functional neuroimaging studies. Neuropsychologia 49, 3361-3369 (2011).
113. Sobin, C., Kiley-Brabeck, K., & Karayiorgou, M. Associations between prepulse inhibition and executive visual attention in children with the 22q11 deletion syndrome. Mol. Psychiatry 10, 553-562 (2005).
114. Almeida, O. P., Howard, R. J., Levy, R., & David, A. S. Psychotic states arising in late life (late paraphrenia) psychopathology and nosology. Br. J. Psychiatry 166, 205-214 (1995).
115. Thaker, G. K. & Carpenter, W. T., Jr. Advances in schizophrenia. Nat. Med. 7, 667-671 (2001).
116. Boyden, E. S., Zhang, F., Bamberg, E., Nagel, G., & Deisseroth, K. Millisecond-timescale, genetically targeted optical control of neural activity. Nat. Neurosci. 8, 1263-1268 (2005).
117. Christensen, M., Larsen, L. A., Kauppinen, S., & Schratt, G. Recombinant Adeno-Associated Virus-Mediated microRNA Delivery into the Postnatal Mouse Brain Reveals a Role for miR-134 in Dendritogenesis in Vivo. Front Neural Circuits. 3, 16 (2010).
118. Kluiver, J. et al. Rapid generation of microRNA sponges for microRNA inhibition. PLoS. One. 7, e29275 (2012).
119. Kluiver, J. et al. Generation of miRNA sponge constructs. Methods. 58, 113-117 (2012).
120. Mellado Lagarde, M. M. et al. Spontaneous regeneration of cochlear supporting cells after neonatal ablation ensures hearing in the adult mouse. Proc. Natl. Acad. Sci. U. S. A 111, 16919-16924 (2014).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

LIST OF SEQUENCES

| SEQ ID NO: | Type | Source | Sequence | Description |
|---|---|---|---|---|
| 1 | DNA | *Homo sapiens* | UCCAGCAUCAGUGAUUUUGUUG | mature miR-338-3p |
| 2 | DNA | Synthetic | TCCAGCATCAGTGATTTTGTTG | forward primer for mmu-miR-338-3p analysis |
| 3 | DNA | Synthetic | TTTTTCATTATTGCTCCTGACC | forward primer for mmu-miR-335-3p analysis |
| 4 | DNA | Synthetic | TCAAGA GCAATAACGAAAAATGT | forward primer for mmu-miR-335-5p analysis |
| 5 | DNA | Synthetic | TCAGCTCCTATATGATG CCTTT | forward primer for mmu-miR-337-3p analysis |
| 6 | DNA | Synthetic | CGGCGTCATGCAGGAGTTGATT | forward primer for mmu-miR-337-5p analysis |
| 7 | DNA | Synthetic | TCAACAAAATCACTGATGCTGG | forward primer for mmu-miR-3065-5p analysis |
| 8 | DNA | Synthetic | TCAGCACCAGGATATTGTTGGGm | forward primer for mmu-miR-3065-3p analysis |
| 9 | DNA | Synthetic | GGATGTCATGATGTGCACAGC | Drd2 forward primer for mRNA analysis |
| 10 | DNA | Synthetic | CGCTTGCGGAGAACGATG | Drd2 reverse primer for mRNA analysis |
| 11 | DNA | Synthetic | ATGCTGGCCTGCCTGTGTTGT | Aatk forward primer |
| 12 | DNA | Synthetic | AGGGGCAGGACATACACATCGG | Aatk reverse primer |
| 13 | DNA | Synthetic | CGCTTCGGCAGCACATATAC | U6 snRNA forward primer |
| 14 | DNA | Synthetic | TTCACGAATTTGCGTGTCAT | U6 snRNA reverse primer |
| 15 | DNA | Synthetic | CTTTTGAACCCTTTTCCATCTG | SnoRNA202 primer |
| 16 | DNA | Synthetic | TTAACAAAAATTCGTCACTACCA | SnoRNA234 primer |
| 17 | DNA | Synthetic | GTACAGCTGTTGACAGTGAGCGACTCCAGCATCAGT GATTTTGTTGTGTGAA | miR-338-3p-1 primer |
| 18 | DNA | Synthetic | CCATCTGTGGCTTCACACAACAAAATCACTGATGCT GGAGTCGCTCACTGTCAACAGCT | miR-338-3p-2 primer |
| 19 | DNA | Synthetic | GCCACAGATGGCAACAAAATCTGATGCTGGAGCTGC CTACTGCCTCGGAA | miR-338-3p-3 primer |
| 20 | DNA | Synthetic | AGCTTTCCGAGGCAGTAGGCAGCTCCAGCATCAGAT TTTGTTG | miR-338-3p-4 primer |
| 21 | DNA | Synthetic | GTACAGCTGTTGACAGTGAGCGACTCAGCTCCTATA TGATGCCTTTTGTGAA | miR-337-3p-1 primer |
| 22 | DNA | Synthetic | CCATCTGTGGCTTCACAAAAGGCATCATATAGGAGC TGAGTCGCTCACTGTCAACAGCT | miR-337-3p-2 primer |
| 23 | DNA | Synthetic | GCCACAGATGGAAAGGCATCATAGGAGCTGAGCTGC CTACTGCCTCGGAA | miR-337-3p-3 primer |
| 24 | DNA | Synthetic | AGCTTTCCGAGGCAGTAGGCAGCTCAGCTCCTATGA TGCCTTT | miR-337-3p-4 primer |
| 25 | DNA | Synthetic | GTACAGCTGTTGACAGTGAGCGACCGGCGTCATGCA GGAGTTGATTTGTGAA | miR-337-5p-1 primer |

-continued

| SEQ ID NO: | Type | Source | Sequence | Description |
|---|---|---|---|---|
| 26 | DNA | Synthetic | CCATCTGTGGCTTCACAAATCAACTCCTGCATGACG CCGGTCGCTCACTGTCAACAGCT | miR-337-5p-2 primer |
| 27 | DNA | Synthetic | GCCACAGATGGAATCAACTCGCATGACGCCGGCTGC CTACTGCCTCGGAA | miR-337-5p-3 primer |
| 28 | DNA | Synthetic | AGCTTTCCGAGGCAGTAGGCAGCCGGCGTCATGCGA GTTGATT (SEQ ID NO: 28) | miR-337-5p-4 primer |
| 29 | DNA | Synthetic | GTACAGCTGTTGACAGTGAGCGACTTTTTCATTATT GCTCCTGACCTGTGAA | miR-335-3p-1 primer |
| 30 | DNA | Synthetic | CCATCTGTGGCTTCACAGGTCAGGAGCAATAATGAA AAAGTCGCTCACTGTCAACAGCT | miR-335-3p-2 primer |
| 31 | DNA | Synthetic | GCCACAGATGGGGTCAGGAGATAATGAAAAAGCTGC CTACTGCCTCGGAA | miR-335-3p-3 primer |
| 32 | DNA | Synthetic | AGCTTTCCGAGGCAGTAGGCAGCTTTTTCATTATCT CCTGACC (SEQ ID NO: 32) | miR-335-3p-4 primer |
| 33 | DNA | Synthetic | GTACAGCTGTTGACAGTGAGCGACTCAAGAGCAATA ACGAAAAATGTTGTAA | miR-335-5p-1 primer |
| 34 | DNA | Synthetic | CCATCTGTGGCTTCACAACATTTTTCGTTATTGCTC TTGAGTCGCTCACTGTCAACAGCT | miR-335-5p-2 primer |
| 35 | DNA | Synthetic | GCCACAGATGGACATTTTTCGATTGCTCTTGAGCTG CCTACTGCCTCGGAA | miR-335-5p-3 primer |
| 36 | DNA | Synthetic | AGCTTTCCGAGGCAGTAGGCAGCTCAAGAGCAATCG AAAAATGT | miR-335-5p-4 primer |
| 37 | DNA | Synthetic | CAACAAATGCGGATGCTGGA | miR-338-3p sponge |
| 38 | DNA | Synthetic | GACACTGTGAGCGAAGACATA | scrambled control |
| 39 | DNA | Synthetic | ATAGCATACATTATACGAAGTTATCACTGG | 5' common reverse primer |
| 40 | DNA | Synthetic | CTTCACTACACTCTCCCTAGTACAGTCTC | 5' gene-specific primer |
| 41 | DNA | Synthetic | TCTAGAAAGTATAGGAACTTCCATGGTC | 3' common forward primer |
| 42 | DNA | Synthetic | AGGAGACTCATAGTTCTCTGTATCATAGC | 3' gene-specific primer |
| 43 | DNA | Mus musculus | ACGGCTGCCGGAGGGGCGGCCGTGCGTGGATGCGGC GGGAGCTGGAAGCCTCGAGCAGCCGGCGCCTTCTCT GGCCCCGGGCGCCCTATGGCTTGAAGAGCCGTGCCA CCCAGTGGCCCCACTGCCCCAATGGATCCACTGAAC CTGTCCTGGTACGATGATGATCTGGAGAGGCAGAAC TGGAGCCGGCCCTTCAATGGGTCCGAAGGGAAGGCA GACAGGCCCCACTACAACTACTATGCCATGCTGCTC ACCCTCCTCATCTTTATCATCGTCTTTGGCAATGTG CTGGTGTGCATGGCTGTATCACGAGAGAAGGCTTTG CAGACCACCACCAACTACCTGATAGTCAGCCTCGCT GTGGCCGATCTTCTGGTGGCCACACTGGTTATGCCC TGGGTCGTCTATCTGGAGGTGGTGGGTGAGTGGAAA TTCAGCAGGATTCACTGTGACATCTTTGTCACTCTG GATGTCATGATGTGCACAGCAAGCATCTTGAACCTG TGTGCCATCAGCATCGACAGGTACACAGCTGTGGCC ATGCCTATGTTGTATAACACACGCTACAGCTCCAAG CGCCGAGTTACTGTCATGATCGCCATTGTCTGGGTC CTGTCCTTCACCATCTCTTGCCCACTGCTCTTTGGA CTCAACAACACAGACCAGAATGAGTGTATCATTGCC AACCCTGCCTTCGTGGTCTACTCCTCCATCGTCTCG TTCTACGTGCCCTTCATCGTCACCCTGCTGGTCTAT ATCAAAATCTACATCGTTCTCCGCAAGCGTCGGAAG CGGGTCAACACCAAGCGTAGCAGCCGAGCTTTCAGA GCCAACCTGAAGACACCACTCAAGGGCAACTGTACC CACCCTGAGGACATGAAACTCTGCACCGTTATCATG AAGTCTAATGGGAGTTTCCCAGTGAACAGGCGGAGA ATGGATGCTGCCCGCCGAGCTCAGGAGCTGGAAATG GAGATGCTGTCAAGCACCAGCCCCCCAGAGAGGACC CGGTATAGCCCCATCCCTCCCAGTCACCACCAGCTC | mouse Drd2 3'UTR (XM_006509996.2) |

| | | | |
|---|---|---|---|
| | | ACTCTCCCCGATCCATCCCACCACGGTCTACATAGC | |
| | | AACCCTGACAGTCCTGCCAAACCAGAAAAGAATGGG | |
| | | CATGCCAAGATTGTCAATCCCAGGATTGCCAAGTTC | |
| | | TTTGAGATCCAGACCATGCCCAATGGCAAAACCCGG | |
| | | ACCTCCCTTAAGACGATGAGCCGCAGGAAGCTCTCC | |
| | | CAGCAGAAGGAGAAGAAAGCCACTCAGATGCTTGCC | |
| | | ATTGTTCTTGGTGTGTTCATCATCTGCTGGCTGCCC | |
| | | TTCTTCATCACGCACATCCTGAATATACACTGTGAC | |
| | | TGCAACATCCCACCAGTCCTCTACAGCGCCTTCACA | |
| | | TGGCTGGGCTATGTCAACAGTGCCGTGAACCCCATC | |
| | | ATCTATACCACCTTCAACATTGAGTTCCGCAAGGCC | |
| | | TTCATGAAGATCCTGCACTGCTGAGTCTGCCCCTTG | |
| | | CCTGCACAGCAGCTGCTTGCCGCCTCCCTGCCTAGG | |
| | | CAGGCCAGACCTCATCCCTGCAAGCTGTGGGCAGAA | |
| | | AGGCCCAGATGGACTCGGCCTTCTCTTGACCCTGCA | |
| | | GGCTCTGCAGTGTTAGCTTGGCTCGGTGCCCCTCTC | |
| | | TGCCCACACACCCTTATCCTGCCAGGGTAGGGCCAG | |
| | | GGAGACTGGTATCTTACCAGCTCTGGGGTTGGATCC | |
| | | ATGGCTCAGAGCAGCTCACAGAGTGCCCCTTTCACA | |
| | | TGCAGATCCTGTCTCCTTGGCACCAAAGAAGCAGCA | |
| | | GCCTTCCTTGACCTTCCTCTCAGGCACGGAAGCTAG | |
| | | CTCAGTAGCGGAGCACACCTTGATTGTTGGCTTGGC | |
| | | CTGGCCCTTGCTTGCCTATGTTGGATCAGGTGGTAG | |
| | | AAGAGAAGGACAGTTCTTACTTTACAGGGACCACAT | |
| | | AGGAAAGCAGGGAACATGCCAAGGCCTCCAGGTGAC | |
| | | GTTAGTGTCGGGAGACACATAAACACCAGGTAGCTC | |
| | | CACGGACCCCAGAGAAACTGAGGCTGAAAATCTGTT | |
| | | TTCCACCCCAACTCTAGTGTGAATCCCTACTTTCCA | |
| | | TAGCAGTGGGTATTGCTATGTTCTCCACTGTTATAG | |
| | | AATCCCATGGGTTTCTGTACCTTCGGGGGAAAATA | |
| | | ACTCTAATCCTCAAGGGCCCCAAGAGAGACTGTAAA | |
| | | GAGAAAAATAGCTGATTTCCCTCTACCCTCCAATCC | |
| | | ACTCCGCCACTTCTTGACATACATTGGACATAGCCA | |
| | | TTCCCCACAGCAGATGCTGGACAGCCTGGGAAGTTG | |
| | | AGCCTTGGACCAGTGTTGGAGCTGAAGTTGGAGGTG | |
| | | GTAACTTGGGGCTCTTGGGCGGGGGTGTTGATATC | |
| | | TTCCCTCTTCCAAGTCTCTTCTCTGCCAGTGCCTCT | |
| | | GCCTTAGAGGAGGCTGTGGATGGGGCTGCTGGGGCT | |
| | | GCTGATACCATTGGGTCTGGCCCTGAGTGAGGGTGG | |
| | | GGAAGCTGCAGCTTGGAGGGGTCTGGGCTCCAACTC | |
| | | TGTAACATCACCATACATGCACCAAACCAATAAAAC | |
| | | CTTGACAAGAGTCATTCCCACGG | |
| 44 | DNA Synthetic | TCCAGCATCAGTGATTTTGTTG | hsa-miR-338-3p primer |

What is claimed is:

1. A method for treatment of schizophrenia or 22q11 deletion syndrome in a subject in need thereof, the method comprising administering to the subject a therapeutically effective amount of (i) miR-338-3p or a mimic or a functional derivative thereof, or (ii) a vector expressing said miR-338-3p or mimic or functional derivative thereof, or (iii) an agent capable of increasing the level or activity of miR-338-3p, wherein the miR-338-3p or mimic or derivative thereof comprises the sequence UCCAGCAUCAGUGAUUUUGUUG (SEQ ID NO: 1).

2. The method of claim 1, wherein the treatment of schizophrenia results in treatment of a positive symptom of schizophrenia in the subject, wherein the positive symptom of schizophrenia is selected from the group consisting of hallucinations, delusions, disorganized thought, and psychosis.

3. The method of claim 1, wherein the miR-338-3p or mimic or derivative thereof consists of the sequence UCCAGCAUCAGUGAUUUUGUUG (SEQ ID NO: 1).

4. The method of claim 1, wherein the administration is systemic, intranasal or targeted to the thalamus.

5. The method of claim 1, wherein the administration results in an increase in the level of miR-338-3p in thalamic neurons of the subject to the level found in healthy subjects.

6. The method of claim 1, wherein the administration results in a decrease in sensitivity of thalamic neurons of the subject to an antipsychotic agent.

7. The method of claim 1, wherein the subject has a decreased level of miR-338-3p in thalamic neurons as compared to a control, wherein the control is a predetermined standard, or the level of miR-338-3p in thalamic neurons of a healthy age- and gender-matched subject or an average value for several such subjects.

8. The method of claim 1, further comprising determining the level of miR-338-3p in thalamic neurons or a bodily fluid sample obtained from the subject.

9. The method of claim 8, wherein the bodily fluid is selected from the group consisting of blood, urine, saliva, and cerebrospinal fluid (CSF).

10. The method of claim 8, wherein the level of miR-338-3p is determined prior to the administration of the treatment.

11. The method of claim 8, wherein the level of miR-338-3p is determined both prior and after the administration of the treatment.

* * * * *